US012637660B2

(12) United States Patent
Milbank et al.

(10) Patent No.: US 12,637,660 B2
(45) Date of Patent: May 26, 2026

(54) SMALL EXTRACELLULAR VESICLES EXPRESSING A DOMINANT NEGATIVE AMPK ALPHA 1 MUTANT FOR USE IN THE TREATMENT OF OBESITY

(71) Applicants: UNIVERSIDADE DE SANTIAGO DE COMPOSTELA, Santiago de Compostela (ES); CENTRE NATIONAL DE LA RECHERCHE SCIENTIFIQUE (CNRS), Paris (FR); INSTITUT NATIONAL DE LA SANTÉ ET DE LA RECHERCHE MÉDICALE (INSERM), Paris (FR); UNIVERSITÉ D'ANGERS, Angers (FR)

(72) Inventors: Edward Milbank, Santiago de Compostela (ES); Miguel Antonio López Pérez, Santiago de Compostela (ES); Maria Del Carmen Martinez Martinez, Paris (FR); Ramaroson Andriantsitohaina, Paris (FR)

(73) Assignees: UNIVERSIDADE DE SANTIAGO DE COMPOSTELA, Santiago de Compostela (ES); CENTRE NATIONAL DE LA RECHERCHE SCIENTIFIQUE (CNRS), Paris (FR); INSTITUT NATIONAL DE LA SANTÉ ET DE LA RECHERCHE MÉDICALE (INSERM), Paris (FR); UNIVERSITÉ D'ANGERS, Angers (FR)

( * ) Notice: Subject to any disclaimer, the term of this patent is extended or adjusted under 35 U.S.C. 154(b) by 234 days.

(21) Appl. No.: 18/681,466

(22) PCT Filed: Jul. 29, 2022

(86) PCT No.: PCT/EP2022/071463

§ 371 (c)(1),
(2) Date: Feb. 5, 2024

(87) PCT Pub. No.: WO2023/012076

PCT Pub. Date: Feb. 9, 2023

(65) Prior Publication Data

US 2025/0127864 A1 Apr. 24, 2025

(30) Foreign Application Priority Data

Aug. 6, 2021 (EP) .................................... 21382749
Aug. 17, 2021 (EP) .................................... 21382763

(51) Int. Cl.

| | |
|---|---|
| ***C12N 5/0784*** | (2010.01) |
| ***A61K 9/50*** | (2006.01) |
| ***A61K 35/15*** | (2015.01) |
| ***A61K 38/16*** | (2006.01) |
| ***A61K 38/45*** | (2006.01) |
| ***A61P 3/04*** | (2006.01) |

(52) U.S. Cl.
CPC .......... *C12N 5/0639* (2013.01); *A61K 9/5068* (2013.01); *A61K 35/15* (2013.01); *A61K 38/162* (2013.01); *A61K 38/45* (2013.01); *A61P 3/04* (2018.01)

(58) Field of Classification Search
CPC .... C12N 5/0639; C12N 9/12; C12N 2509/00; A61K 9/5068; A61K 35/15; A61K 38/162; A61K 38/45; A61K 48/0041; A61P 3/04; A01K 2217/075; A01K 2227/105; C12Y 207/11026
See application file for complete search history.

(56) References Cited

U.S. PATENT DOCUMENTS

2008/0119548 A1 5/2008 Ronnett et al.

OTHER PUBLICATIONS

Alvarez-Crespo et al., "Essential role of UCP1 modulating the central effects of thyroid hormones on energy balance," *Molecular Metabolism* 5:271-282, Feb. 10, 2016. (12 pages).
Alvarez-Erviti et al., "Delivery of siRNA to the mouse brain by systemic injection of targeted exosomes," *Nature Biotechnology 29*(4):341-345, Apr. 2011 [Published online Mar. 20, 2011]. (7 pages).
Beall et al., "Mouse hypothalamic GT1-7 cells demonstrate AMPK-dependent intrinsic glucose-sensing behaviour," *Diabetologia 55*:2432-2444, Jul. 4, 2012. (13 pages).
Buzas et al., "Emerging role of extracellular vesicles in inflammatory diseases," *Nature Reviews Rheumatology*, Advance Online Publication, Feb. 18, 2014. (9 pages).

(Continued)

*Primary Examiner* — Jessica Worsham
(74) *Attorney, Agent, or Firm* — Seed Intellectual Property Law Group LLP

(57) ABSTRACT

The present invention relates to a population of small extracellular vesicles (sEVs) for use in the treatment of obesity in a subject in need thereof, wherein the sEVs comprise at least one polynucleotide encoding a D168A dominant negative AMP-activated protein kinase alpha 1 (AMPKa1-DN) mutant protein operably linked and under the control of a steroidogenic factor 1 (SF1) promoter, wherein the sEVs are engineered to transiently express in their outer membrane at least one fusion protein comprising the neurotrophic rabies virus (RVG) peptide fused to lysosome-associated membrane protein 2b. Said population is highly safe and effective, as the sEVs, when administered systematically, are capable of exerting their effect in the SF1 expressing neurons located in the ventromedial nucleus of the hypothalamus.

20 Claims, 33 Drawing Sheets

Specification includes a Sequence Listing.

(56) References Cited

OTHER PUBLICATIONS

Campderrós et al., "Brown Adipocytes Secrete GDF15 in Response to Thermogenic Activation," *Obesity 27*(10):1606-1616, Aug. 14, 2019. (11 pages).
Cannon et al., "Brown Adipose Tissue: Function and Physiological Significance," *Physiological Reviews 84*:277-359, Jan. 2004. (83 pages).
Carling, "AMPK signalling in health and disease," *Current Opinion in Cell Biology 45*:31-37, Apr. 2017 [Published online Feb. 21, 2017]. (14 pages).
Choi et al., "Revisiting the ventral medial nucleus of the hypothalamus: the roles of SF-1 neurons in energy homeostasis," *Frontiers in Neuroscience 7*:71, May 7, 2013. (9 pages).
Claret et al., "AMPK is essential for energy homeostasis regulation and glucose sensing by POMC and AgRP neurons," *The Journal of Clinical Investigation 117*(8):2325-2336, Aug. 2007. (13 pages).
Clemmensen et al., "Current and Emerging Treatment Options in Diabetes Care," *Handbook of Experimental Pharmacology*, vol. 233, pp. 437-459, 2015. (23 pages).
Colombo et al., "Biogenesis, secretion, and intercellular interactions of exosomes and other extracellular vesicles," *Annual Review of Cell and Developmental Biology 30*:255-289, Aug. 21, 2014. (35 pages).
Contreras et al., "Ceramide sensing in the hippocampus: The lipostatic theory and *Ockham's razor," Molecular Metabolism 3*:90-91, 2014 [Published online Dec. 27, 2013]. (2 pages).
Contreras et al., "The brain and brown fat," *Annals of Medicine 47*:150-168, Jun. 10, 2014. (19 pages).
Corley et al., "Potential regulation of GnRH gene by a steroidogenic factor-1-like protein," *Molecular Human Reproduction 6*(8):671-676, Aug. 2000. (6 pages).
Coyral-Castel et al., "The Effect of AMP-Activated Kinase Activation on Gonadotrophin-Releasing Hormone Secretion in GT1-7 Cells and its Potential Role in Hypothalamic Regulation of the Oestrous Cyclicity in Rats," *Journal of Neuroendocrinology 20*:335-346, Jan. 11, 2008. (12 pages).
Cui et al., "The cellular and molecular bases of leptin and ghrelin resistance in obesity," *Nature Reviews Endocrinology 13*:338-351, Jun. 2017 [Published online Feb. 24, 2017]. (14 pages).
Dalli et al., "Microparticle alpha-2-macroglobulin enhances pro-resolving responses and promotes survival in sepsis," *EMBO Molecular Medicine 6*(1):27-42, 2014 [Published online Dec. 12, 2013]. (17 pages).
Domingos et al., "Characterizing Manufactured Nanoparticles in the Environment: Multimethod Determination of Particle Sizes," *Environmental Science & Technology 43*(19):7277-7284, Apr. 30, 2009. (8 pages).
Dragano et al., "Recent Updates on Obesity Treatments: Available Drugs and Future Directions," *Neuroscience Review 437*:215-239, Apr. 29, 2020. (25 pages).
Foretz et al., "Metformin: From Mechanisms of Action to Therapies," *Cell Metabolism 20*:953-966, Dec. 2, 2014. (14 pages).
Foretz et al., "Therapy: Metformin takes a new route to clinical efficacy," *Nature Reviews Endocrinology 11*(7):390-392, Jun. 2, 2015. (6 pages).
Gao et al., "Two Regions Within the Proximal Steroidogenic Factor 1 Promoter Drive Somatic Cell-Specific Activity in Developing Gonads of the Female Mouse," *Biology of Reproduction 84*:422-434, 2011 [Published online Oct. 20, 2010]. (14 pages).
González-García et al., "Estradiol Regulates Energy Balance by Ameliorating Hypothalamic Ceramide-Induced ER Stress," *Cell Reports 25*:413-423, Oct. 9, 2018. (17 pages).
Hardie et al., "AMPK: An Energy-Sensing Pathway with Multiple Inputs and Outputs," *Trends in Cell Biology*, Article in Press, Nov. 23, 2015. (12 pages).
Heras et al., "Central Ceramide Signaling Mediates Obesity-Induced Precocious Puberty," *Cell Metabolism 32*:951-966, Dec. 1, 2020. (25 pages).
Hong et al., "Fat Quantification in the Abdomen," *Topics in Magnetic Resonance Imaging 26*(6):221-227, Dec. 2017 (HHS Public Access Author Manuscript, available in PMC Dec. 1, 2018). (19 pages).
Hu et al., "Segmentation and quantification of adipose tissue by magnetic resonance imaging," *MAGMA 29*(2):259-276, Apr. 2016 (HHS Public Access Author Manuscript, available in PMC Apr. 1, 2017). (30 pages).
Johann et al., "Thyroid-Hormone-Induced Browning of White Adipose Tissue Does Not Contribute to Thermogenesis and Glucose Consumption," *Cell Reports 27*:3385-3400, Jun. 11, 2019. (20 pages).
Johnson et al., "Reproducible MRI Measurement of Adipose Tissue Volumes in Genetic and Dietary Rodent Obesity Models," *Journal of Magnetic Resonance Imaging 28*:915-927, Oct. 2008. (13 pages).
Kahn et al., "AMP-activated protein kinase: Ancient energy Review gauge provides clues to modern understanding of metabolism," *Cell Metabolism 1*:15-25, Jan. 2005. (11 pages).
Kamerkar et al., "Exosomes Facilitate Therapeutic Targeting of Oncogenic KRAS in Pancreatic Cancer," *Nature 546*(7659):498-503, Jun. 22, 2017 (HHS Public Access Author Manuscript, available in PMC Dec. 7, 2017). (41 pages).
Kumar et al., "Transvascular delivery of small interfering RNA to the central nervous system," *Nature 448*:39-43, Jul. 5, 2007. (7 pages).
López et al., "Hypothalamic AMPK and fatty acid metabolism mediate thyroid regulation of energy balance," *Nature Medicine 16*(9):1001-1009, Sep. 2010 [Published online Aug. 29, 2010]. (9 pages).
López et al., "Hypothalamic AMPK: a canonical regulator of whole-body energy balance," *Nature Reviews Endocrinology 12*:421-432, Jul. 2016 [Published online May 20, 2016]. (12 pages).
López et al., "Hypothalamic Fatty Acid Metabolism Mediates the Orexigenic Action of Ghrelin," *Cell Metabolism 7*:389-399, May 2008. (11 pages).
López, "AMPK Wars: the VMH Strikes Back, Return of the PVH," *Trends in Endocrinology & Metabolism 29*(3):135-137, Mar. 2018. (3 pages).
Malloci et al., "Extracellular Vesicles: Mechanisms in Human Health and Disease," *Antioxidants and Redox Signaling*, pre-print version, Apr. 30, 2018. (125 pages).
Martins et al., "A Functional Link between AMPK and Orexin Mediates the Effect of BMP8B on Energy Balance," *Cell Reports 16*:2231-2242, Aug. 23, 2016. (13 pages).
Martínez de Morentin et al., "Estradiol Regulates Brown Adipose Tissue Thermogenesis via Hypothalamic AMPK," *Cell Metabolism 20*:41-53, Jul. 1, 2014. (13 pages).
Martínez de Morentin et al., "Nicotine Induces Negative Energy Balance Through Hypothalamic AMP-Activated Protein Kinase," *Diabetes 61*(4):807-817, Apr. 2012 [Published online Mar. 14, 2012]. (19 pages).
Martínez et al., "Extracellular Vesicles in Metabolic Syndrome," *Circulation Research 120*:1674-1686, May 12, 2017. (13 pages).
Martínez-Sánchez et al.,"Hypothalamic AMPK-ER Stress-JNK1 Axis Mediates the Central Actions of Thyroid Hormones on Energy Balance," *Cell Metabolism 26*:212-229, Jul. 5, 2017. (45 pages).
Mellon et al., "Immortalization of Hypothalamic GnRH Neurons by Genetically Targeted Tumorigenesis," *Neuron 5*:1-10, Jul. 1990. (10 pages).
Milbank et al., "Extracellular vesicles: Pharmacological modulators of the peripheral and central signals governing obesity," *Pharmacology & Therapeutics 157*:65-83, 2016 [Published online Nov. 23, 2015]. (20 pages).
Milbank et al., "Small extracellular vesicle-mediated targeting of hypothalamic AMPKα1 corrects obesity through BAT activation," *Nature Metabolism 3*:1415-1431, Oct. 21, 2021. (29 pages).
Milbank, "Extracellular vesicles as a therapeutic strategy to prevent or reverse obesity and its metabolic complications in the field of nanomedicine," Doctoral Thesis, Université d'Angers, May 19, 2020. (136 pages).
Morrison et al., "Central Neural Regulation of Brown Adipose Tissue Thermogenesis and Energy Expenditure," *Cell Metabolism 19*:741-756, May 6, 2014. (16 pages).

(56) References Cited

OTHER PUBLICATIONS

Müller et al., "Anti-Obesity Therapy: from Rainbow Pills to Polyagonists," *Pharmacological Reviews 70*:712-746, Oct. 2018. (35 pages).
Parker et al., "Steroidogenic Factor 1: A Key Determinant of Endocrine Development and Function," *Endocrine Reviews 18*(3):361-377, Jun. 1997. (17 pages).
Quah et al., "The immunogenicity of dendritic cell-derived exosomes," *Blood Cells, Molecules, and Diseases 35*:94-110, Jun. 21, 2005. (17 pages).
Sanchez-Garrido et al., "Intergenerational Influence of Paternal Obesity on Metabolic and Reproductive Health Parameters of the Offspring: Male-Preferential Impact and Involvement of Kiss1-Mediated Pathways," *Endocrinology 159*(2):1005-1018, Feb. 2018 [Published online Dec. 22, 2017]. (14 pages).
Schimmer et al., "Minireview: Steroidogenic Factor 1: Its Roles in Differentiation, Development, and Disease," *Molecular Endocrinology 24*:1322-1337, Mar. 4, 2010. (16 pages).
Schneeberger et al., "Recent insights into the role of hypothalamic AMPK signaling cascade upon metabolic control," *Frontiers in Neuroscience 6*:185, Dec. 20, 2012. (6 pages).
Seoane-Collazo et al., "Central nicotine induces browning through hypothalamic κ opioid receptor," *Nature Communications 10*:4037, Sep. 6, 2019. (12 pages).
Seoane-Collazo et al., "SF1-Specific AMPKα1 Deletion Protects Against Diet-Induced Obesity," *Diabetes 67*:2213-2226, Nov. 2018. (14 pages).
Tang et al., "Delivery of chemotherapeutic drugs in tumour cell-derived microparticles," *Nature Communications 3*:1282, Dec. 18, 2012. (11 pages).
Tang et al., "Identification of Aneuploidy-Selective Antiproliferation Compounds," *Cell 144*:499-512, Feb. 18, 2011. (14 pages).
Tschöp et al., "Unimolecular Polypharmacy for Treatment of Diabetes and Obesity," *Cell Metabolism 24*:51-62, Jul. 12, 2016. (12 pages).
Vazquez et al., "SIRTI mediates obesity- and nutrient-dependent perturbation of pubertal timing by epigenetically controlling Kiss1 expression," *Nature Communications 9*:4194, Oct. 10, 2018. (15 pages).
Warner et al., "Inappropriate heat dissipation ignites brown fat thermogenesis in mice with a mutant thyroid hormone receptor α1," *PNAS 110*(40):16241-16246, Oct. 1, 2013. (6 pages).
Whittle et al., "BMP8B Increases Brown Adipose Tissue Thermogenesis through Both Central and Peripheral Actions," *Cell 149*:871-885, May 11, 2012. (15 pages).
Woods et al., "Characterization of the Role of AMP-Activated Protein Kinase in the Regulation of Glucose-Activated Gene Expression Using Constitutively Active and Dominant Negative Forms of the Kinase," *Molecular and Cellular Biology 20*(18):6704-6711, Sep. 2000. (8 pages).
Yang et al., "AMPK/α-Ketoglutarate Axis Dynamically Mediates DNA Demethylation in the Prdm16 Promoter and Brown Adipogenesis," *Cell Metabolism 24*:542-554, Oct. 11, 2016 [Published online Sep. 15, 2016]. (14 pages).
Zadra et al., "A novel direct activator of AMPK inhibits prostate cancer growth by blocking lipogenesis," *EMBO Molecular Medicine 6*(4):519-538, 2013. (20 pages).

f g j
Heart rate (bpm)
400
300
200
100
0
Control
SF1-AMPKα1-DN
k
Systolic arterial pressure (mmHg)
150
100
50
0
Control
SF1-AMPKα1-DN
l
Diastolic arterial pressure (mmHg)
150
100
50
0
Control
SF1-AMPKα1-DN
m
Mean arterial pressure (mmHg)
150
100
50
0
Control
SF1-AMPKα1-DN

SEQUENCE LISTING

```
Sequence total quantity: 41
SEQ ID NO: 1            moltype = AA  length = 560
FEATURE                 Location/Qualifiers
REGION                  1..560
                        note = AMPK1-DN mutant protein amino acid sequence
source                  1..560
                        mol_type = protein
                        organism = synthetic construct
SEQUENCE: 1
MEQKLISEED LGGGEKQKHD GRVKIGHYIL GDTLGVGTFG KVKVGKHELT GHKVAVKILN  60
RQKIRSLDVV GKIRREIQNL KLFRHPHIIK LYQVISTPSD IFMVMEYVSG GELFDYICKN  120
GRLDEKESRR LFQQILSGVD YCHRHMVVHR DLKPENVLLD AHMNAKIAAF GLSNMMSDGE  180
FLRTSCGSPN YAAPEVISGR LYAGPEVDIW SSGVILYALL CGTLPFDDDH VPTLFKKICD  240
GIFYTPQYLN PSVISLLKHM LQVDPMKRAT IKDIREHEWF KQDLPKYLFP EDPSYSSTMI  300
DDEALKEVCE KFECSEEEVL SCLYNRNHQD PLAVAYHLII DNRRIMNEAK DFYLATSPPD  360
SFLDDHHLTR PHPERVPFLV AETPRARHTL DELNPQKSKH QGVRKAKWHL GIRSQSRPND  420
IMAEVCRAIK QLDYEWKVVN PYYLRVRRKN PVTSTFSKMS LQLYQVDSRT YLLDFRSIDD  480
EITEAKSGTA TPQRSGSISN YRSCQRSDSD AEAQGKPSEV SLTSSVTSLD SSPVDVAPRP  540
GSHTIEFFEM CANLIKILAQ                                             560

SEQ ID NO: 2            moltype = DNA  length = 1683
FEATURE                 Location/Qualifiers
misc_feature            1..1683
                        note = Polynucleotide sequence encoding for the dominant
                         negativeAMP-activated protein kinase alpha 1 (AMPK1)
                         mutant protein.
source                  1..1683
                        mol_type = other DNA
                        organism = synthetic construct
SEQUENCE: 2
atggagcaga agcttatctc cgaggaggac ctcggtggcg gcgagaagca gaagcacgac  60
gggcgggtga agatcggcca ctacatcctg ggggacacgc tgggcgtcgg caccttcggg  120
aaagtgaagg tgggcaagca cgagttgact ggacataaag ttgctgtgaa gatactcaac  180
cggcagaaga ttcgaagcct ggacgtggtc gggaaaatcc gcagagagat ccagaacctg  240
aagcttttca ggcaccctca tataatcaaa ctgtaccagg tcatcagtac accgtctgat  300
attttcatgg tcatggaata tgtctcagga ggagagctat ttgattatat ctgtaaaaat  360
ggaaggttgg acgaaaagga gagtcgacgt ctgttccagc agatcctttc tggtgtggac  420
tattgtcaca ggcatatggt ggtccacaga gatttgaaac ctgaaaacgt cctgcttgat  480
gcacacatga atgcaaagat agccgccttc ggtctttcaa acatgatgtc agatggtgaa  540
tttttaagaa cgagctgtgg ctcgcccaat tatgctgcac cagaagtaat ttcaggaaga  600
ttgtacgcag gccctgaagt agacatctgg agcagcgggg tcattctcta tgctttgctg  660
tgtggaactc tccctttga tgatgaccac gtgccaactc tttttaagaa gatatgtgac  720
gggatatttt ataccctca gtatttgaat ccctctgtaa taagcctttt gaagcatatg  780
ctgcaggtag atcctatgaa gagggccaca ataaaagata tcagggaaca tgaatggttt  840
aagcaggacc ttccaaaata tctctttcct gaagacccgt cttatagttc aaccatgatt  900
gatgatgaag ccttaaaaga agtgtgtgag aagttcgagt gctcagagga ggaggtcctc  960
```

-continued

```
agctgcctgt acaacagaaa ccaccaggac ccactggcag ttgcctacca cctcataata  1020
gacaacagga gaataatgaa cgaagccaaa gatttctact tggcaacaag cccacccgat  1080
tctttcctcg atgatcacca tttaactcgg cctcaccctg agagagtacc attcttggtt  1140
gccgaaacac caagggcccg acacacccta gatgaattaa acccacagaa atccaaacac  1200
caaggcgtac ggaaggcaaa gtggcatttg ggattcgaa gtcaaagccg acccaatgac  1260
atcatggcag aagtgtgtag agcaatcaag cagttggact atgaatggaa ggttgtaaac  1320
ccctattatt tgcgtgtgcg aaggaagaac cctgtgacaa gcacattttc caaaatgagt  1380
ctacagctat accaagtgga tagtaggact tacttattgg atttccgaag tattgatgat  1440
gagattacag aagccaaatc agggactgct actccacaga gatcgggatc catcagcaac  1500
tatcgatctt gccaaaggag cgactccgac gccgaggctc aaggaaagcc ctcagaagtc  1560
tctcttacct catccgtgac ctccctcgac tcctctcctg ttgacgtagc tccaagacca  1620
ggaagtcaca cgatagaatt ttttgaaatg tgtgcaaatc taattaaaat tcttgcacag  1680
taa                                                                1683
```

```
SEQ ID NO: 3           moltype = DNA  length = 741
FEATURE                Location/Qualifiers
misc_feature           1..741
                       note = Steroidogenic factor 1 (SF1) polynucleotide sequence.
source                 1..741
                       mol_type = other DNA
                       organism = synthetic construct
SEQUENCE: 3
aaaacaaaac aaaacaaaac aaaacaaaac aaaacaaaca aacaaacaaa caaacaaaaa  60
cccttctttc ctacctggtc ctagtaccca catagtccta cctgaagtcc ctgaagccac  120
acccttagcc cagcagtctt ggcacaacct cagtttcccc agctaccaat ggaccatatc  180
tgcagctccc agagaagcca ccaaaaaggc cacacaaacc ccacctgatg ggttccacca  240
tgccatttct ccacactagc cattctgact cctcactcag atctgggaca agctggacca  300
cgcagcccag gcaaggaccc agggaggaag ccattcaagg ggagaaactc ccagcctggt  360
aagggagcag gccataaatc aggtcccact cccacccagt cgctaacaag ccgctgccta  420
tctgcctaca tggggtccct gcctcaggct ccctcatcag cctggacagc cagctggcca  480
aggtctctcc agtgccttgg cctctgcccc cacccagggc ccccataaag atagggatat  540
tttttttct tttagaagag tgaaaaaaga tatagaccca aatgaagaga aacaccaaca  600
aaggaggaga aaggcctgca gagtcacgtg ggggcagaga ccaattgggc ctccggtggc  660
ccccccaccc acgaggggag gaggaaagga cgatcggaca gggccagttt ccagtccgcc  720
gctgcccgcc cgctgctggg t                                            741
```

```
SEQ ID NO: 4           moltype = DNA  length = 2476
FEATURE                Location/Qualifiers
misc_feature           1..2476
                       note = Polyucleotide sequence encoding a AMPK1-DN mutant
                        proteinoperably linked and under the control of the SF1
                        promoter.
source                 1..2476
                       mol_type = other DNA
                       organism = synthetic construct
SEQUENCE: 4
aaaacaaaac aaaacaaaac aaaacaaaac aaaacaaaca aacaaacaaa caaacaaaaa  60
cccttctttc ctacctggtc ctagtaccca catagtccta cctgaagtcc ctgaagccac  120
acccttagcc cagcagtctt ggcacaacct cagtttcccc agctaccaat ggaccatatc  180
tgcagctccc agagaagcca ccaaaaaggc cacacaaacc ccacctgatg ggttccacca  240
tgccatttct ccacactagc cattctgact cctcactcag atctgggaca agctggacca  300
cgcagcccag gcaaggaccc agggaggaag ccattcaagg ggagaaactc ccagcctggt  360
aagggagcag gccataaatc aggtcccact cccacccagt cgctaacaag ccgctgccta  420
tctgcctaca tggggtccct gcctcaggct ccctcatcag cctggacagc cagctggcca  480
aggtctctcc agtgccttgg cctctgcccc cacccagggc ccccataaag atagggatat  540
tttttttct tttagaagag tgaaaaaaga tatagaccca aatgaagaga aacaccaaca  600
aaggaggaga aaggcctgca gagtcacgtg ggggcagaga ccaattgggc ctccggtggc  660
ccccccaccc acgaggggag gaggaaagga cgatcggaca gggccagttt ccagtccgcc  720
gctgcccgcc cgctgctggg taccgtttaa actcgaggtc gacggtatcg ataagcttga  780
tatcgaattc gccatggagc agaagcttat ctccgaggag gacctcggtg gcggcgagaa  840
gcagaagcac gacgggcggg tgaagatcgg ccactacatc ctgggggaca cgctgggcgt  900
cggcaccttc gggaaagtga aggtgggcaa gcacgagttg actggacata aagttgctgt  960
gaagatactc aaccggcaga agattcgaag cctggacgtg gtcgggaaaa tccgcagaga  1020
gatccagaac ctgaagcttt tcaggcaccc tcatataatc aaactgtacc aggtcatcag  1080
tacaccgtct gatattttca tggtcatgga atatgtctca ggaggagagc tatttgatta  1140
tatctgtaaa aatggaaggt tggacgaaaa ggagagtcga cgtctgttcc agcagatcct  1200
ttctggtgtg gactattgtc acaggcatat ggtggtccac agagatttga aacctgaaaa  1260
cgtcctgctt gatgcacaca tgaatgcaaa gatagccgcc ttcggtcttt caaacatgat  1320
gtcagatggt gaatttttaa gaacgagctg tggctcgccc aattatgctg caccagaagt  1380
aatttcagga agattgtacg caggccctga agtagacatc tggagcagcg gggtcattct  1440
ctatgctttg ctgtgtggaa ctctcccttt tgatgatgac cacgtgccaa ctctttttaa  1500
gaagatatgt gacgggatat tttatacccc tcagtatttg aatccctctg taataagcct  1560
tttgaagcat atgctgcagg tagatcctat gaagagggcc acaataaaag atatcaggga  1620
acatgaatgg tttaagcagg accttccaaa atatctcttt cctgaagacc cgtcttatag  1680
ttcaaccatg attgatgatg aagccttaaa agaagtgtgt gagaagttcg agtgctcaga  1740
ggaggaggtc ctcagctgcc tgtacaacag aaaccaccag gacccactgg cagttgccta  1800
ccacctcata atagacaaca ggagaataat gaacgaagcc aaagatttct acttggcaac  1860
aagcccaccc gattctttcc tcgatgatca ccatttaact cggcctcacc ctgagagagt  1920
accattcttg gttgccgaaa caccaagggc ccgacacacc ctagatgaat taaacccaca  1980
```

-continued

```
gaaatccaaa caccaaggcg tacggaaggc aaagtggcat ttggggattc gaagtcaaag  2040
ccgacccaat gacatcatgg cagaagtgtg tagagcaatc aagcagttgg actatgaatg  2100
gaaggttgta aacccctatt atttgcgtgt gcgaaggaag aaccctgtga caagcacatt  2160
ttccaaaatg agtctacagc tataccaagt ggatagtagg acttacttat tggatttccg  2220
aagtattgat gatgagatta cagaagccaa atcagggact gctactccac agagatcggg  2280
atccatcagc aactatcgat cttgccaaag gagcgactcc gacgccgagg ctcaaggaaa  2340
gccctcagaa gtctctctta cctcatccgt gacctccctc gactcctctc ctgttgacgt  2400
agctccaaga ccaggaagtc acacgataga attttttgaa atgtgtgcaa atctaattaa  2460
aattcttgca cagtaa                                                  2476

SEQ ID NO: 5            moltype = AA  length = 449
FEATURE                 Location/Qualifiers
REGION                  1..449
                        note = Fusion protein: Neurotrophic rabies virus (RVG)
                         peptide fused tolysosome-associated membrane protein 2b
                         (Lamp2b).
source                  1..449
                        mol_type = protein
                        organism = synthetic construct
SEQUENCE: 5
MCLSPVKGAK LILIFLFLGA VQSNALIVNL TDSKGTCLYA RYTIWMPENP RPGTPCDIFT  60
NSRGKRASNG SGGAEWEMNF TITYETTNQT NKTITIAVPD KATHDGSSCG DDRNSAKIMI  120
QFGFAVSWAV NFTKEASHYS IHDIVLSYNT SDSTVFPGAV AKGVHTVKNP ENFKVPLDVI  180
FKCNSVLTYN LTPVVQKYWG IHLQAFVQNG TVSKNEQVCE EDQTPTTVAP IIHTTAPSTT  240
TTLTPTSTPT PTPTPTPTVG NYSIRNGNTT CLLATMGLQL NITEEKVPFI FNINPATTNF  300
TGSCQPQSAQ LRLNNSQIKY LDFIFAVKNE KRFYLKEVNV YMYLANGSAF NISNKNLSFW  360
DAPLGSSYMC NKEQVLSVSR AFQINTFNLK VQPFNVTKGQ YSTAQECSLD DDTILIPIIV  420
GAGLSGLIIV IVIAYLIGRR KTYAGYQTL                                    449

SEQ ID NO: 6            moltype = DNA  length = 92
FEATURE                 Location/Qualifiers
misc_feature            1..92
                        note = RVG primers -F
source                  1..92
                        mol_type = other DNA
                        organism = synthetic construct
SEQUENCE: 6
tcgatacacc atttggatgc ccgagaatcc gagaccaggg acaccttgtg acatttttac  60
caatagcaga gggaagagag catccaacgg gt                                92

SEQ ID NO: 7            moltype = DNA  length = 92
FEATURE                 Location/Qualifiers
misc_feature            1..92
                        note = RVG primer - R
source                  1..92
                        mol_type = other DNA
                        organism = synthetic construct
SEQUENCE: 7
ccggacccgt tggatgctct cttccctctg ctattggtaa aaatgtcaca aggtgtccct  60
ggtctcggat tctcgggcat ccaaatggtg ta                                92

SEQ ID NO: 8            moltype = DNA  length = 21
FEATURE                 Location/Qualifiers
misc_feature            1..21
                        note = AMPK primer- F
source                  1..21
                        mol_type = other DNA
                        organism = synthetic construct
SEQUENCE: 8
acggccgaga agcagaagca c                                            21

SEQ ID NO: 9            moltype = DNA  length = 20
FEATURE                 Location/Qualifiers
misc_feature            1..20
                        note = AMPK primer -R
source                  1..20
                        mol_type = other DNA
                        organism = synthetic construct
SEQUENCE: 9
tcgtgcttgc ccaccttcac                                              20

SEQ ID NO: 10           moltype = DNA  length = 19
FEATURE                 Location/Qualifiers
misc_feature            1..19
                        note = GAPDH Primer-F
source                  1..19
                        mol_type = other DNA
                        organism = synthetic construct
SEQUENCE: 10
```

-continued

```
agtatgtcgt ggagtctac                                              19

SEQ ID NO: 11          moltype = DNA  length = 19
FEATURE                Location/Qualifiers
misc_feature           1..19
                       note = GAPDH Primer-R
source                 1..19
                       mol_type = other DNA
                       organism = synthetic construct
SEQUENCE: 11
catacttggc aggtttctc                                              19

SEQ ID NO: 12          moltype = DNA  length = 21
FEATURE                Location/Qualifiers
misc_feature           1..21
                       note = STAR primer F
source                 1..21
                       mol_type = other DNA
                       organism = synthetic construct
SEQUENCE: 12
agttcgacgt cggagctctc t                                           21

SEQ ID NO: 13          moltype = DNA  length = 20
FEATURE                Location/Qualifiers
misc_feature           1..20
                       note = STAR primer R
source                 1..20
                       mol_type = other DNA
                       organism = synthetic construct
SEQUENCE: 13
tacttagcac ttcgtccccg                                             20

SEQ ID NO: 14          moltype = DNA  length = 20
FEATURE                Location/Qualifiers
misc_feature           1..20
                       note = P450scc primer F
source                 1..20
                       mol_type = other DNA
                       organism = synthetic construct
SEQUENCE: 14
gattgcggag ctggagatga                                             20

SEQ ID NO: 15          moltype = DNA  length = 20
FEATURE                Location/Qualifiers
misc_feature           1..20
                       note = P450scc primer R
source                 1..20
                       mol_type = other DNA
                       organism = synthetic construct
SEQUENCE: 15
tcttttctgg tcacggctgg                                             20

SEQ ID NO: 16          moltype = DNA  length = 20
FEATURE                Location/Qualifiers
misc_feature           1..20
                       note = 17-HSD3 primer F
source                 1..20
                       mol_type = other DNA
                       organism = synthetic construct
SEQUENCE: 16
ctgagcactt ccggtgagag                                             20

SEQ ID NO: 17          moltype = DNA  length = 20
FEATURE                Location/Qualifiers
misc_feature           1..20
                       note = 17-HSD3 primer R
source                 1..20
                       mol_type = other DNA
                       organism = synthetic construct
SEQUENCE: 17
ggcctttcct ccttgactcc                                             20

SEQ ID NO: 18          moltype = DNA  length = 20
FEATURE                Location/Qualifiers
misc_feature           1..20
                       note = LH  primer F
source                 1..20
                       mol_type = other DNA
                       organism = synthetic construct
```

-continued

```
SEQUENCE: 18
gagttctgcc cagtctgcat                                               20

SEQ ID NO: 19          moltype = DNA  length = 22
FEATURE                Location/Qualifiers
misc_feature           1..22
                       note = LH  primer R
source                 1..22
                       mol_type = other DNA
                       organism = synthetic construct
SEQUENCE: 19
aggaaaggag actatggggt ct                                            22

SEQ ID NO: 20          moltype = DNA  length = 22
FEATURE                Location/Qualifiers
misc_feature           1..22
                       note = S11 primer F
source                 1..22
                       mol_type = other DNA
                       organism = synthetic construct
SEQUENCE: 20
cattcagacg gagcgtgctt ac                                            22

SEQ ID NO: 21          moltype = DNA  length = 20
FEATURE                Location/Qualifiers
misc_feature           1..20
                       note = S11 primer R
source                 1..20
                       mol_type = other DNA
                       organism = synthetic construct
SEQUENCE: 21
tgcatcttca tcttcgtcac                                               20

SEQ ID NO: 22          moltype = DNA  length = 20
FEATURE                Location/Qualifiers
misc_feature           1..20
                       note = Atp2a2 primer F
source                 1..20
                       mol_type = other DNA
                       organism = synthetic construct
SEQUENCE: 22
tccgctacct catctcatcc                                               20

SEQ ID NO: 23          moltype = DNA  length = 19
FEATURE                Location/Qualifiers
misc_feature           1..19
                       note = Atp2a2 primer R
source                 1..19
                       mol_type = other DNA
                       organism = synthetic construct
SEQUENCE: 23
caggtctgga ggattgaac                                                19

SEQ ID NO: 24          moltype = DNA  length = 21
FEATURE                Location/Qualifiers
misc_feature           1..21
                       note = Gdp2 primer F
source                 1..21
                       mol_type = other DNA
                       organism = synthetic construct
SEQUENCE: 24
gaaggggact attcttgtgg g                                             21

SEQ ID NO: 25          moltype = DNA  length = 21
FEATURE                Location/Qualifiers
misc_feature           1..21
                       note = Gdp2 primer R
source                 1..21
                       mol_type = other DNA
                       organism = synthetic construct
SEQUENCE: 25
ggatgtcaaa ttcgggtgtg t                                             21

SEQ ID NO: 26          moltype = DNA  length = 20
FEATURE                Location/Qualifiers
misc_feature           1..20
                       note = Ppar primer F
source                 1..20
                       mol_type = other DNA
```

-continued

```
                         organism = synthetic construct
SEQUENCE: 26
tcgctgatgc actgcctatg                                              20

SEQ ID NO: 27            moltype = DNA  length = 21
FEATURE                  Location/Qualifiers
misc_feature             1..21
                         note = Ppar primer R
source                   1..21
                         mol_type = other DNA
                         organism = synthetic construct
SEQUENCE: 27
gagaggtcca cagagctgat t                                            21

SEQ ID NO: 28            moltype = DNA  length = 21
FEATURE                  Location/Qualifiers
misc_feature             1..21
                         note = Ryr1 primer F
source                   1..21
                         mol_type = other DNA
                         organism = synthetic construct
SEQUENCE: 28
cagtttttgc ggacggatga t                                            21

SEQ ID NO: 29            moltype = DNA  length = 20
FEATURE                  Location/Qualifiers
misc_feature             1..20
                         note = Ryr1 primer R
source                   1..20
                         mol_type = other DNA
                         organism = synthetic construct
SEQUENCE: 29
caccggcctc cacagtattg                                              20

SEQ ID NO: 30            moltype = DNA  length = 25
FEATURE                  Location/Qualifiers
misc_feature             1..25
                         note = Sln primer F
source                   1..25
                         mol_type = other DNA
                         organism = synthetic construct
SEQUENCE: 30
gaggtggaga gactgaggtc cttgg                                        25

SEQ ID NO: 31            moltype = DNA  length = 21
FEATURE                  Location/Qualifiers
misc_feature             1..21
                         note = Sln primer R
source                   1..21
                         mol_type = other DNA
                         organism = synthetic construct
SEQUENCE: 31
gaagctcggg gcacacagca g                                            21

SEQ ID NO: 32            moltype = DNA  length = 22
FEATURE                  Location/Qualifiers
misc_feature             1..22
                         note = Ucp3 primer F
source                   1..22
                         mol_type = other DNA
                         organism = synthetic construct
SEQUENCE: 32
gagatggtga cctacgacat ca                                           22

SEQ ID NO: 33            moltype = DNA  length = 22
FEATURE                  Location/Qualifiers
misc_feature             1..22
                         note = Ucp3 primer R
source                   1..22
                         mol_type = other DNA
                         organism = synthetic construct
SEQUENCE: 33
gcgttcatgt atcgggtctt ta                                           22

SEQ ID NO: 34            moltype = DNA  length = 20
FEATURE                  Location/Qualifiers
misc_feature             1..20
                         note = SF1-AMPK1-DN primer F
source                   1..20
```

-continued

```
                        mol_type = other DNA
                        organism = synthetic construct
SEQUENCE: 34
aaacaccaag gcgtacggaa                                            20

SEQ ID NO: 35           moltype = DNA  length = 20
FEATURE                 Location/Qualifiers
misc_feature            1..20
                        note = SF1-AMPK1-DN primer R
source                  1..20
                        mol_type = other DNA
                        organism = synthetic construct
SEQUENCE: 35
tggcggccgc tctagattac                                            20

SEQ ID NO: 36           moltype = DNA  length = 20
FEATURE                 Location/Qualifiers
misc_feature            1..20
                        note = HPRT primer F
source                  1..20
                        mol_type = other DNA
                        organism = synthetic construct
SEQUENCE: 36
ggttaagcag tacagcccca                                            20

SEQ ID NO: 37           moltype = DNA  length = 20
FEATURE                 Location/Qualifiers
misc_feature            1..20
                        note = HPRT primer R
source                  1..20
                        mol_type = other DNA
                        organism = synthetic construct
SEQUENCE: 37
tccaacactt cgagaggtcc                                            20

SEQ ID NO: 38           moltype = DNA  length = 1378
FEATURE                 Location/Qualifiers
misc_feature            1..1378
                        note = Nucleotide sequence of the fusion protein made of
                         theNeurotrophic rabies virus (RVG) peptide fused
                         tolysosome-associated membrane protein 2b (Lamp2b).
source                  1..1378
                        mol_type = other DNA
                        organism = synthetic construct
SEQUENCE: 38
gctagcggtc gccaccatgt gcctctctcc ggttaaaggc gcaaagctca tcctgatctt  60
tctgttccta ggagccgttc agtccaatgc attgatagtt aatttgacag attcaaaggg  120
tacttgcctt tatgctcgat acaccatttg gatgcccgag aatccgagac cagggacacc  180
ttgtgacatt tttaccaata gcagagggaa gagagcatcc aacgggtccg gaggtgcaga  240
atgggagatg aatttcacaa taacatatga aactacaaac caaaccaata aaactataac  300
cattgcagta cctgacaagg cgacacacga tggaagcagt tgtggggatg accggaatag  360
tgccaaaata atgatacaat ttggattcgc tgtctcttgg gctgtgaatt ttaccaagga  420
agcatctcat tattcaattc atgacatcgt gctttcctac aacactagtg atagcacagt  480
atttcctggt gctgtagcta aaggagttca tactgttaaa aatcctgaga atttcaaagt  540
tccattggat gtcatcttta agtgcaatag tgttttaact tacaacctga ctcctgtcgt  600
tcagaaatat tggggtattc acctgcaagc ttttgtccaa aatggtacag tgagtaaaaa  660
tgaacaagtg tgtgaagaag accaaactcc caccactgtg gcacccatca ttcacaccac  720
tgccccgtcg actacaacta cactcactcc aacttcaaca cccactccaa ctccaactcc  780
aactccaacc gttggaaact acagcattag aaatggcaat actacctgtc tgctggctac  840
catggggctg cagctgaaca tcactgagga gaaggtgcct ttcattttta acatcaaccc  900
tgccacaacc aacttcaccg gcagctgtca acctcaaagt gctcaactta ggctgaacaa  960
cagccaaatt aagtatcttg actttatctt tgctgtgaaa aatgaaaaac ggttctatct  1020
gaaggaagtg aatgtctaca tgtatttggc taatggctca gctttcaaca tttccaacaa  1080
gaaccttagc ttctgggatg cccctctggg aagttcttat atgtgcaaca aagagcaggt  1140
gctttctgtg tctagagcgt ttcagatcaa cacctttaac ctaaaggtgc aaccttttaa  1200
tgtgacaaaa ggacagtatt ctacagccca ggagtgttcg ctggatgatg acaccattct  1260
aataccaatt atagttggtg ctggtctttc aggcttgatt atcgttatag tgattgctta  1320
cctaattggc agaagaaaga cctatgctgg atatcagact ctgtaacact aaggatcc    1378

SEQ ID NO: 39           moltype = AA  length = 547
FEATURE                 Location/Qualifiers
REGION                  1..547
                        note = AMPK1-DN mutant protein amino acid sequence(without
                         the Myc-Tag peptide and the G-linker)
source                  1..547
                        mol_type = protein
                        organism = synthetic construct
SEQUENCE: 39
MEKQKHDGRV KIGHYILGDT LGVGTFGKVK VGKHELTGHK VAVKILNRQK IRSLDVVGKI  60
```

-continued

```
RREIQNLKLF RHPHIIKLYQ VISTPSDIFM VMEYVSGGEL FDYICKNGRL DEKESRRLFQ  120
QILSGVDYCH RHMVVHRDLK PENVLLDAHM NAKIAAFGLS NMMSDGEFLR TSCGSPNYAA  180
PEVISGRLYA GPEVDIWSSG VILYALLCGT LPFDDDHVPT LFKKICDGIF YTPQYLNPSV  240
ISLLKHMLQV DPMKRATIKD IREHEWFKQD LPKYLFPEDP SYSSTMIDDE ALKEVCEKFE  300
CSEEEVLSCL YNRNHQDPLA VAYHLIIDNR RIMNEAKDFY LATSPPDSFL DDHHLTRPHP  360
ERVPFLVAET PRARHTLDEL NPQKSKHQGV RKAKWHLGIR SQSRPNDIMA EVCRAIKQLD  420
YEWKVVNPYY LRVRRKNPVT STFSKMSLQL YQVDSRTYLL DFRSIDDEIT EAKSGTATPQ  480
RSGSISNYRS CQRSDSDAEA QGKPSEVSLT SSVTSLDSSP VDVAPRPGSH TIEFFEMCAN  540
LIKILAQ                                                            547

SEQ ID NO: 40           moltype = AA  length = 559
FEATURE                 Location/Qualifiers
source                  1..559
                        mol_type = protein
                        organism = Rattus norvegicus
SEQUENCE: 40
MRRLSSWRKM ATAEKQKHDG RVKIGHYILG DTLGVGTFGK VKVGKHELTG HKVAVKILNR  60
QKIRSLDVVG KIRREIQNLK LFRHPHIIKL YQVISTPSDI FMVMEYVSGG ELFDYICKNG  120
RLDEKESRRL FQQILSGVDY CHRHMVVHRD LKPENVLLDA HMNAKIADFG LSNMMSDGEF  180
LRTSCGSPNY AAPEVISGRL YAGPEVDIWS SGVILYALLC GTLPFDDDHV PTLFKKICDG  240
IFYTPQYLNP SVISLLKHML QVDPMKRATI KDIREHEWFK QDLPKYLFPE DPSYSSTMID  300
DEALKEVCEK FECSEEEVLS CLYNRNHQDP LAVAYHLIID NRRIMNEAKD FYLATSPPDS  360
FLDDHHLTRP HPERVPFLVA ETPRARHTLD ELNPQKSKHQ GVRKAKWHLG IRSQSRPNDI  420
MAEVCRAIKQ LDYEWKVVNP YYLRVRRKNP VTSTFSKMSL QLYQVDSRTY LLDFRSIDDE  480
ITEAKSGTAT PQRSGSISNY RSCQRSDSDA EAQGKPSEVS LTSSVTSLDS SPVDVAPRPG  540
SHTIEFFEMC ANLIKILAQ                                               559

SEQ ID NO: 41           moltype = AA  length = 559
FEATURE                 Location/Qualifiers
source                  1..559
                        mol_type = protein
                        organism = synthetic construct
SEQUENCE: 41
MRRLSSWRKM ATAEKQKHDG RVKIGHYILG DTLGVGTFGK VKVGKHELTG HKVAVKILNR  60
QKIRSLDVVG KIRREIQNLK LFRHPHIIKL YQVISTPSDI FMVMEYVSGG ELFDYICKNG  120
RLDEKESRRL FQQILSGVDY CHRHMVVHRD LKPENVLLDA HMNAKIAAFG LSNMMSDGEF  180
LRTSCGSPNY AAPEVISGRL YAGPEVDIWS SGVILYALLC GTLPFDDDHV PTLFKKICDG  240
IFYTPQYLNP SVISLLKHML QVDPMKRATI KDIREHEWFK QDLPKYLFPE DPSYSSTMID  300
DEALKEVCEK FECSEEEVLS CLYNRNHQDP LAVAYHLIID NRRIMNEAKD FYLATSPPDS  360
FLDDHHLTRP HPERVPFLVA ETPRARHTLD ELNPQKSKHQ GVRKAKWHLG IRSQSRPNDI  420
MAEVCRAIKQ LDYEWKVVNP YYLRVRRKNP VTSTFSKMSL QLYQVDSRTY LLDFRSIDDE  480
ITEAKSGTAT PQRSGSISNY RSCQRSDSDA EAQGKPSEVS LTSSVTSLDS SPVDVAPRPG  540
SHTIEFFEMC ANLIKILAQ                                               559
```

SMALL EXTRACELLULAR VESICLES EXPRESSING A DOMINANT NEGATIVE AMPK ALPHA 1 MUTANT FOR USE IN THE TREATMENT OF OBESITY

REFERENCE TO AN ELECTRONIC SEQUENCE LISTING

The contents of the electronic sequence listing (eolf-seql.xml; Size: 61,204 bytes; and Date of Creation: Feb. 5, 2024) is herein incorporated by reference in its entirety.

TECHNICAL FIELD OF THE INVENTION

The present invention relates to the field of nanobiomedicine. Particularly, the present invention relates to the use of small extracellular vesicles administered via the systemic route for the treatment of obesity.

BACKGROUND OF THE INVENTION

Obesity causes thousands of deaths per year worldwide. This is due to the many direct and indirect comorbidities associated with this condition including cancer, cardiovascular diseases and type 2 diabetes (T2D) and yet it is the most preventable epidemic[1-6]. The most effective treatment of obesity is bariatric surgery, which not only decreases body weight but also improves T2D. However, the majority of obese subjects do not qualify for bariatric surgery. In addition, given the harmful and risky side effects of bariatric surgery, growing efforts are made to develop innovative anti-obesity drugs[1,2,5]. However, even if some current pharmacological-driven strategies exhibit some beneficial outcomes in decreasing body weight, most of them display undesired side effects, mainly due to lack of specificity.

Moreover, most of the current strategies are designed to target the food intake component of energy balance, while not many of them trigger energy expenditure (EE). Indeed, as the regulation of body weight is complex and interconnected to multiple organism functions, increasing the specificity of the treatments by the identification of new molecular targets, appears as crucial [1,2,5]. AMPK is a cellular gauge that is activated in conditions of low energy, promoting counterregulatory responses[3,7-11]. Recent evidence has demonstrated that modulation of AMPK in the hypothalamus is a canonical mechanism regulating energy balance. In particular, hormonal, pharmacological or genetic inhibition of AMPKα1 in the ventromedial nucleus of the hypothalamus (VMH) leads to an increase in sympathetic nervous system (SNS) activity which stimulates brown adipose tissue (BAT) thermogenesis, elevating EE and subsequently leading to feeding-independent weight loss[12-18]. At a cellular level, this action occurs in steroidogenic factor 1 (SF1) neurons of the VMH, in which the specific deletion of AMPKα1 promotes resistance to diet-induced obesity (DIO) and metabolic improvement in mice[17,18].

One of the keys of efficiency of anti-obesity drugs development is their specificity of action. In this regard, the therapeutic potential of gene therapy is limited due to (i) its low stability within body fluids such as blood, inducing their rapid degradation following systemic injections, (ii) its limited tissue-specificity actions. To counter these undesired consequences following non-specific delivery, last decades provide some stimulating breakthrough through the expansion of nanomedicine strategies. Adenovirus or synthetic nanoparticles delivery strategies are developed in regenerative medicine or against several pathologies. However, several issues limited their uses, including their repeated injections that induce inflammation-undesired responses. It is thus desirable to develop new bio-inspired nanovesicles, able to target the tissue of interest and specifically delivering the therapeutic gene, but without inducing an immune response nor affecting other biological processes.

Extracellular vesicles (EVs) are heterogeneous populations of naturally occurring nano to micro-sized membrane vesicles released by essentially all cell types. It has been shown that that EVs possess therapeutic potential through reprogramming of target cells, affording modulation of cellular processes and secretomes—the molecules secreted by cells—and eventually favoring tissue repair after reprogramming of target cells.

The present invention provides the use of extracellular vesicles as therapeutic vectors that are administered systemically to deliver a plasmid encoding for a dominant negative isoform of AMPKα1 for use in the treatment or prevention of obesity.

Data expressed as mean±SEM. ***P<0.001 vs. Control. Statistical significance was assessed by two-sided Student's t-test.

Figure 10:
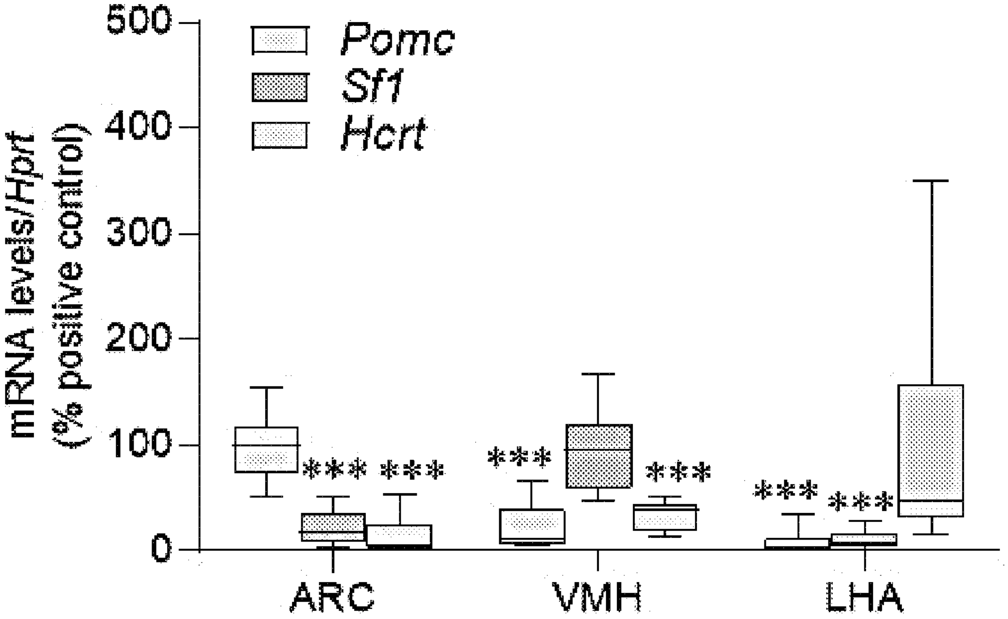

FIG. 10. Control of hypothalamic nuclei dissections. Quantification of Pomc, Sf1 and Hcrt/orexin mRNA levels in ARC, VMH and LHA dissections [n=19-20 mice/group; box plot indicate median (middle line), 25th, 75th percentile (box) and $10^{th}$-$90^{th}$ percentiles (whiskers; minima and maxima, respectively)]. Data expressed as mean±SEM. ***P<0.001 vs. Pomc ARC, Sf1 VMH and Hcrt LHA. Statistical significance was assessed by two-sided Student's t-test.

Figure 11:
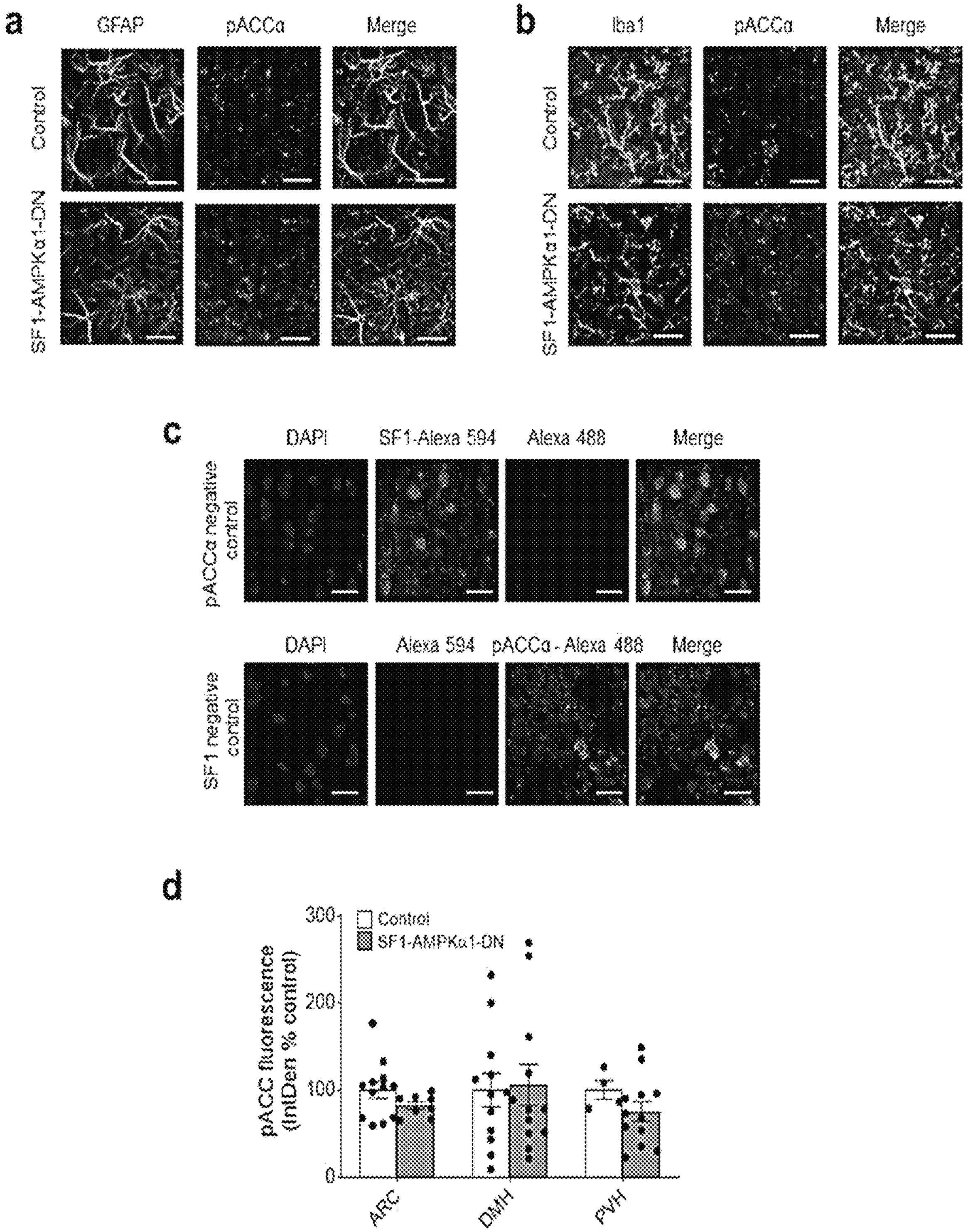

FIG. 11. Effect of systemic treatment with SF1-AMPKα1-DN loaded sEVs on hypothalamic AMPK activity. (a) Representative confocal images depicting GFAP (green), pACCα (magenta) and merged reactivity in brain sections after 24 h of intravenous injection with control (non-loaded) or SF1-AMPKα1-DN loaded sEVs. Scale bars represent 20 μm. (b) Representative confocal images depicting Iba1 (green), pACCα (magenta) and merged reactivity in brain sections after 24 h of intravenous injection with control (non-loaded) or SF1-AMPKα1-DN loaded sEVs. Scale bars represent 20 μm. (c) Negative controls for pACCα and SF1 double immunofluorescence. Representative confocal images depicting DAPI (blue), Alexa594, with or without SF1 (red), Alexa 488 with or without pACCα (green) and merged reactivity in brain sections. Scale bars represent 20 μm. (d) Quantification of pACCα fluorescence in ARC, DMH and PVH (quantification per field; 4-12 fields) after 24 h of intravenous injection with control (non-loaded) or SF1-AMPKα1-DN loaded sEVs. Data expressed as mean±SEM. Statistical significance was assessed by two-sided Student's t-test.

Figure 12:
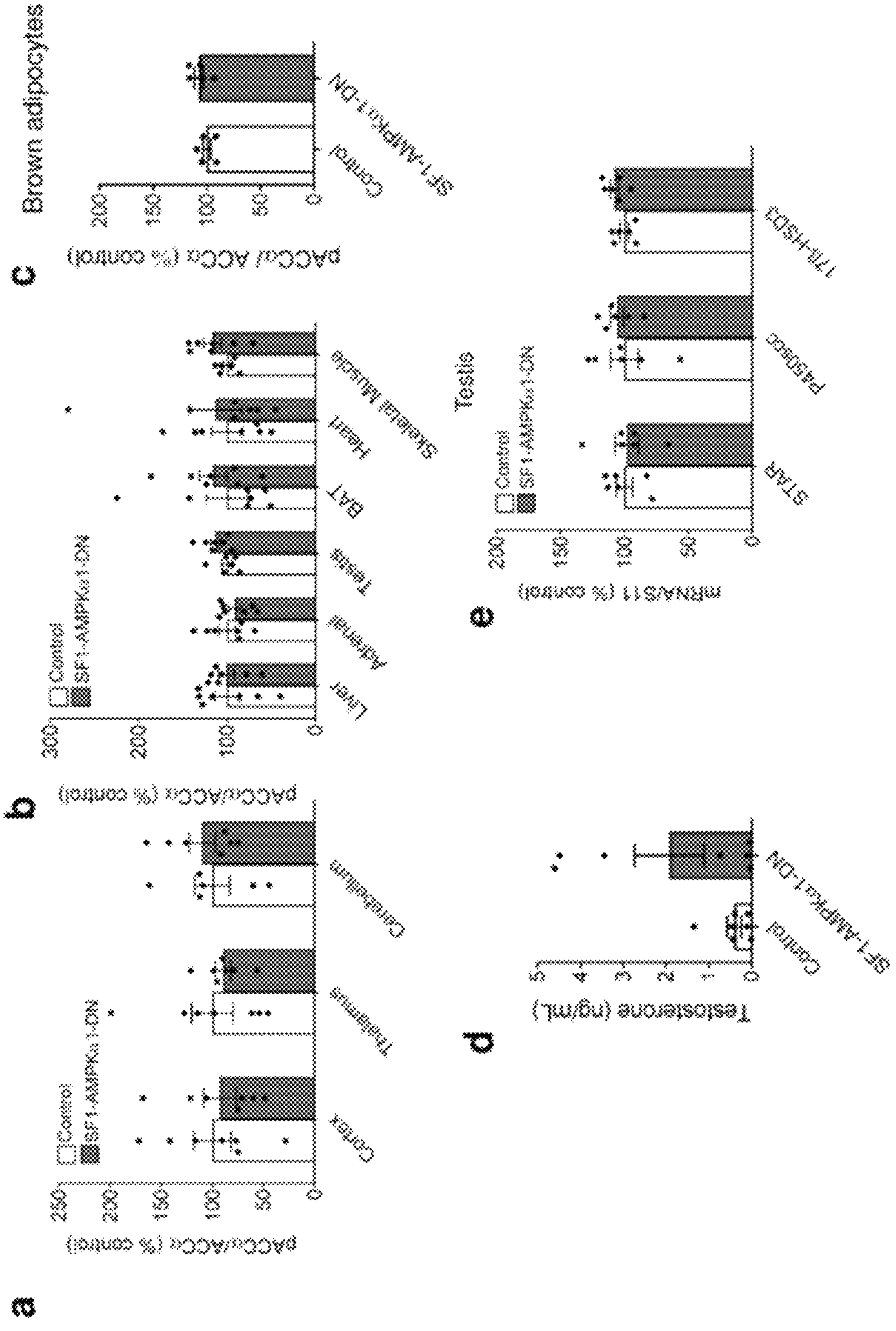
Figure 12:
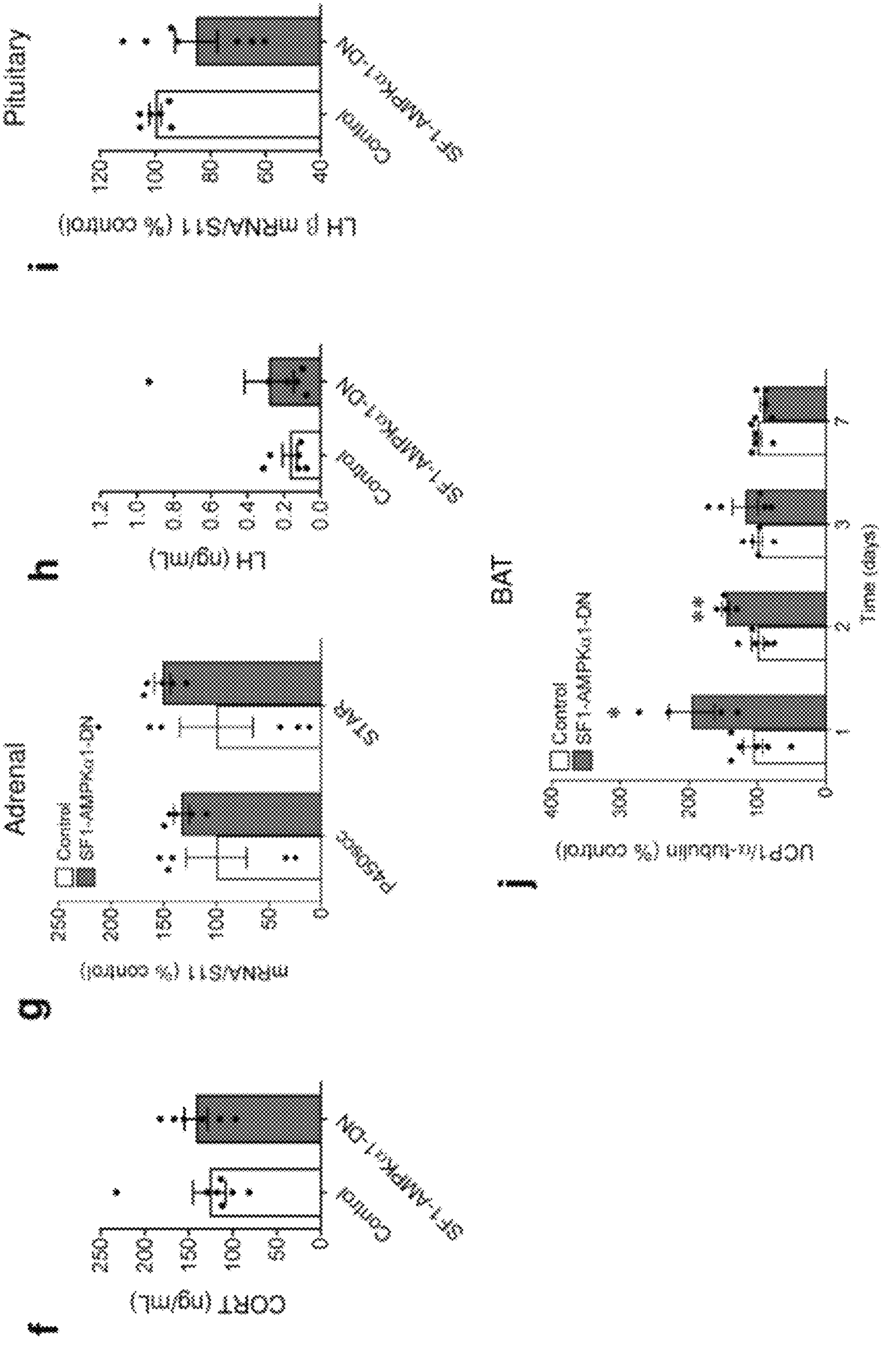

FIG. 12. Effect of systemic treatment with SF1-AMPKα1-DN loaded sEVs on central and peripheral tissues. (a) Quantification of pACCα/ACCα levels in cortex, thalamus and cerebellum after 28 days of intravenous injection with control (non-loaded, n=6-7 mice/group) or SF1-AMPKα1-DN loaded (n=7 mice/group) sEVs, expressed in % of the control. (b) Quantification of pACCα/ACCα levels in liver, adrenal gland, testis, BAT, heart and skeletal muscle after 28 days of intravenous injection with control (non-loaded, n=6-7 mice/group) or SF1-AMPKα1-DN loaded (n=7 mice/group) sEVs, expressed in % of the control. (c) Quantification of pACCα/ACCα levels in brown adipocytes after 24 h of incubation with control (non-loaded, n=5 samples/group) or SF1-AMPKα1-DN loaded (n=5 samples/group) sEVs, expressed in % of the control. (d) Quantification of circulating testosterone levels expressed in ng/ml after 28 days of intravenous injection with control (non-loaded, n=7 mice/group) or SF1-AMPKα1-DN loaded (n=7 mice/group) sEVs. (e) Quantification of mRNA levels of steroidogenic enzymes (STAR, p450scc and 17β-HSD3) in testis after 28 days of intravenous injection with control (non-loaded, n=7 mice/group) or SF1-AMPKα1-DN loaded (n=7 mice/group) sEVs, expressed in % of the control. (f) Quantification of circulating CORT levels expressed in ng/ml after 28 days of intravenous injection with control (non-loaded, n=7 mice/group) or SF1-AMPKα1-DN loaded (n=6 mice/group) sEVs. (g) Quantification of mRNA levels of steroidogenic enzymes (STAR and p450scc) in adrenal gland after 28 days of intravenous injection with control (non-loaded, n=5 mice/group) or SF1-AMPKα1-DN loaded (n=6 mice/group) sEVs, expressed in % of the control. (h) Quantification of circulating LH levels expressed in ng/ml after 28 days of intravenous injection with control (non-loaded, n=6 mice/group) or SF1-AMPKα1-DN loaded (n=6 mice/group) sEVs. (i) Quantification of mRNA levels of LH p subunit in pituitary after 28 days of intravenous injection with control (non-loaded, n=6 mice/group) or SF1-AMPKα1-DN loaded (n=7 mice/group) sEVs, expressed in % of the control. (j) Quantification of BAT UCP1 levels at 1, 2, 3 and 7 days after a single injection in the tail vein of control (non-loaded, n=5-6 mice/group) or SF1-AMPKα1-DN (n=4-5 mice/group) sEVs at day 0. Values are expressed in % of the control. Data expressed as mean±SEM. *P<0.05 and **P<0.01 vs. Control. Statistical significance was assessed by two-sided Student's t-test.

Figure 13:
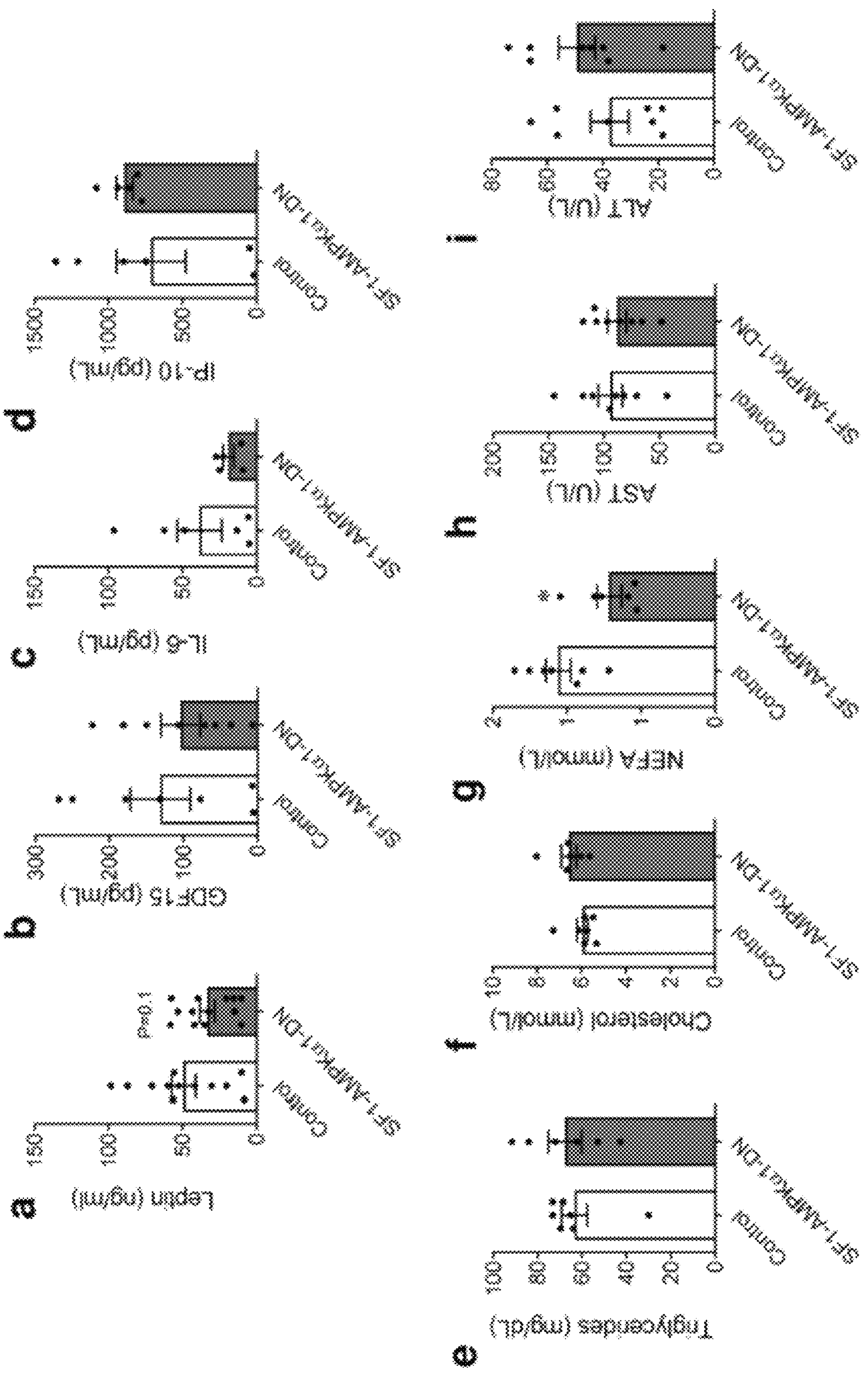
Figure 13:
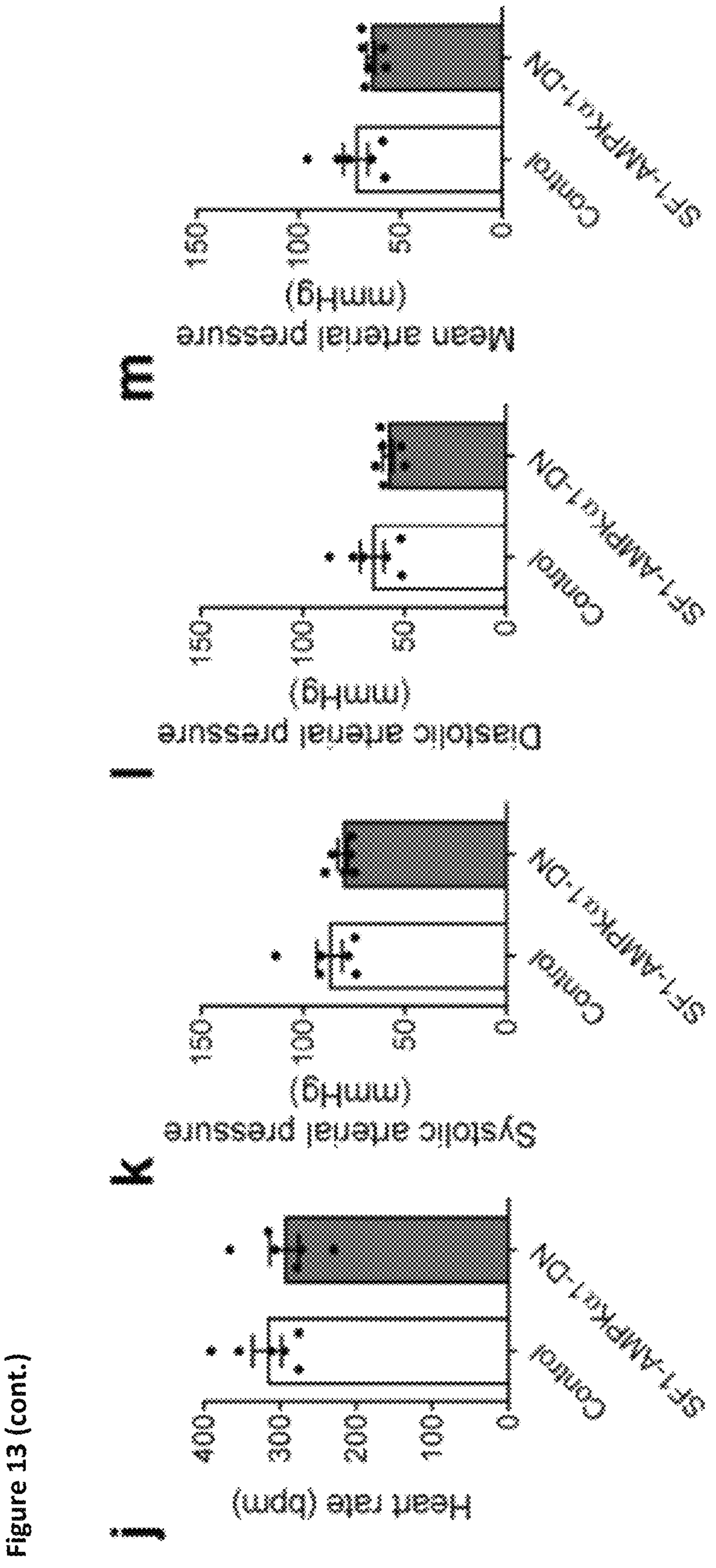

FIG. 13. Effect of systemic treatment with SF1-AMPKα1-DN sEVs on circulating and hemodynamic parameters. (a-i) Quantification of circulating leptin (a), GDF15 (b), IL-6 (c), IP-10 (d), triglycerides (e), cholesterol (f), NEFA (g), AST (h) and ALT (i) after 28 days of intravenous injection with control (non-loaded) or SF1-AMPKα1-DN loaded sEVs. (n=5-13 mice/group). (j-m) Quantification of heart rate (j, n=6 mice/group), systolic arterial pressure (k, n=6 mice/group), diastolic arterial pressure (I, n=6 mice/group) and mean arterial pressure (m, n=6 mice/group) after 24 h of intravenous injection with control (non-loaded) or SF1-AMPKα1-DN loaded sEVs. Data expressed as mean±SEM. Statistical significance was assessed by two-sided Student's t-test.

Figure 14:
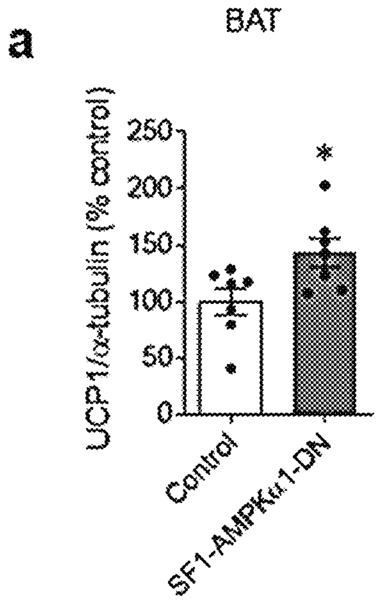
Figure 14:
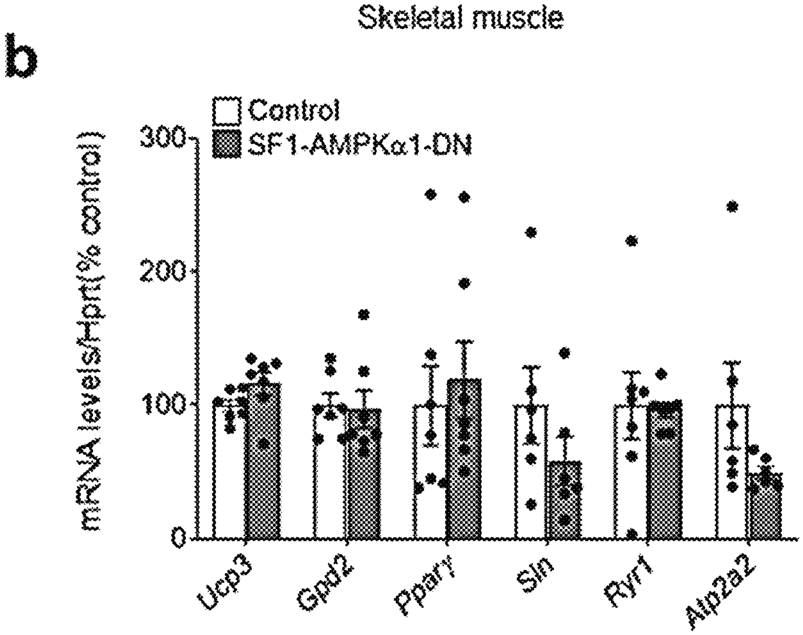

FIG. 14. Effect of systemic treatment with SF1-AMPKα 1-DN sEVs on BAT and skeletal muscle thermogenic markers. (a) Quantification of UCP1 protein levels in the BAT after 28 days of intravenous injection with control (non-loaded, n=7 mice/group) or SF1-AMPKα1-DN loaded (n=7 mice/group) sEVs. (b) Quantification of mRNA levels of thermogenic markers (Ucp3, Gpd2, Ppary, Sin, Ryr1, Atp2a2) in skeletal muscle after 28 days of intravenous injection with control (non-loaded, n=6-7 mice/group) or SF1-AMPKα1-DN loaded (n=6-7 mice/group) sEVs, expressed in % of the control. Data expressed as mean±SEM. *, **P<0.05 vs. Control. Statistical significance was assessed by Student's t-tests.

Figure 15:
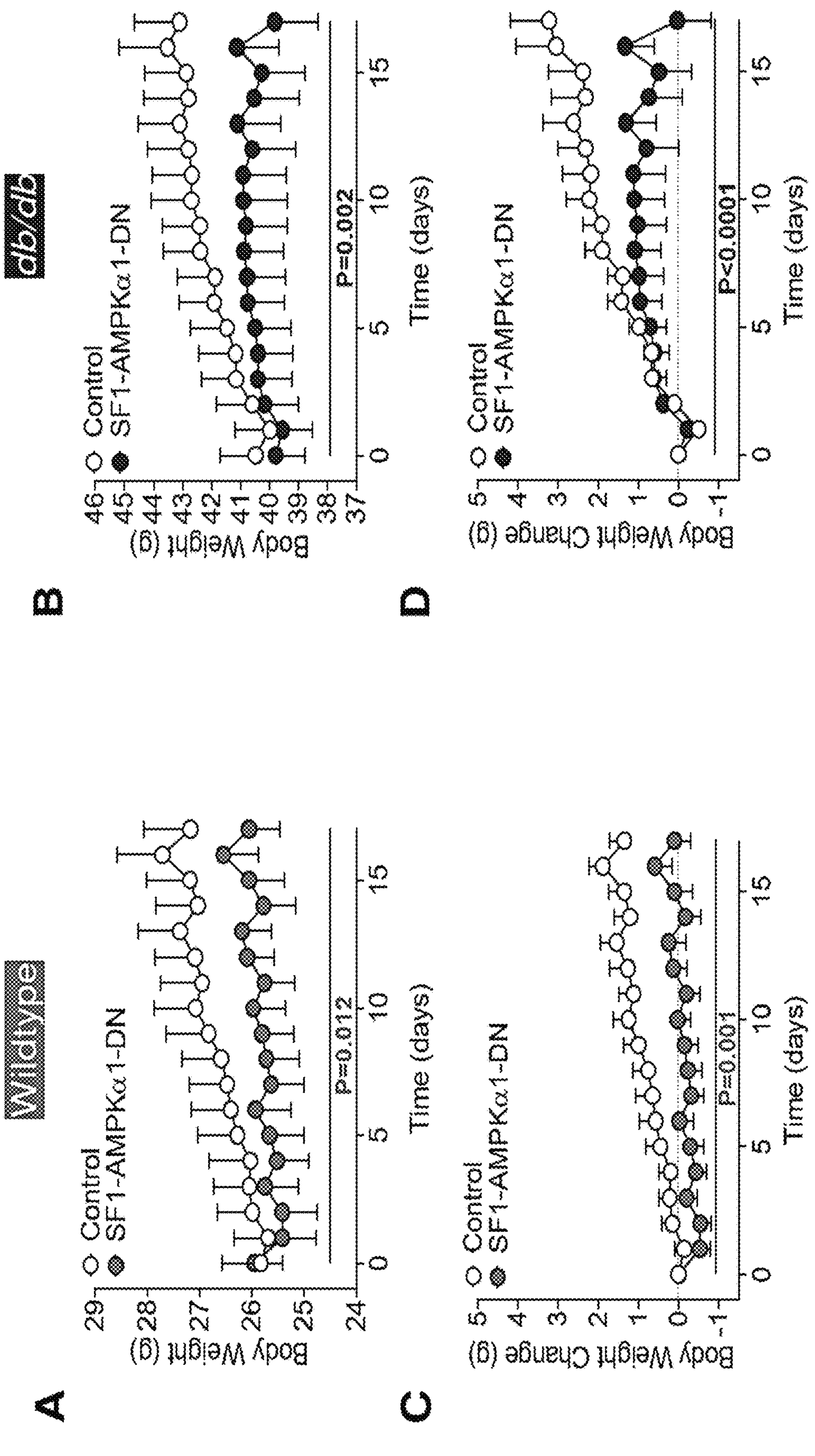
Figure 15:
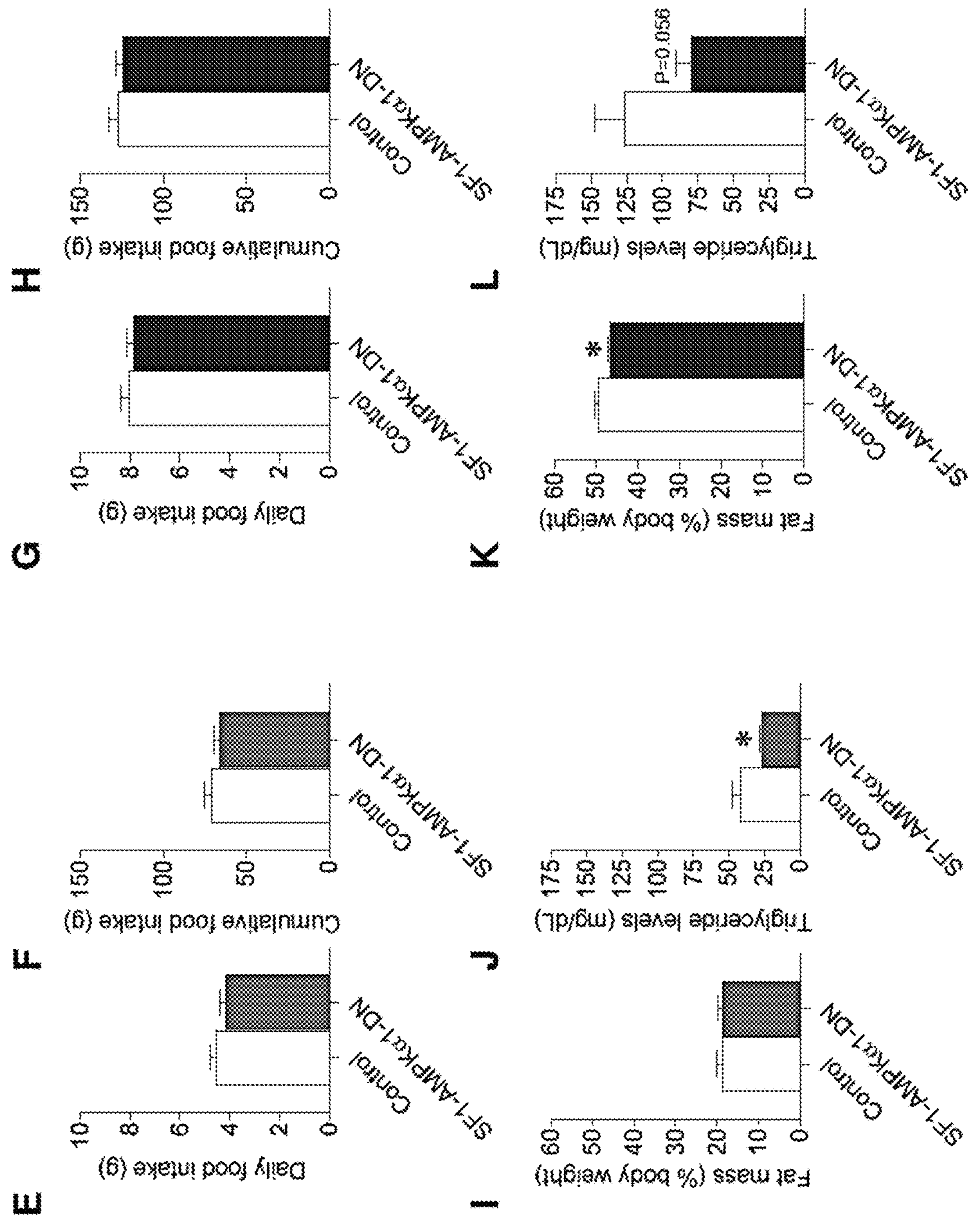

FIG. 15. Effect of systemic treatment with SF1-AMPKα1-DN loaded sEVs on energy balance in db/db mice (A-B) Body weight; (C-D) body weight change; (E-H) daily and cumulative food intake; (I and K) fat mass and (J and L) serum triglyceride levels of wildtype and db/db mice intravenously treated with control (non-loaded; n=8 wildtype mice; n=8 db/db mice) or SF1-AMPKα1-DN loaded (n=7 wildtype; n=7 db/db mice) sEVs. Data are expressed as MEAN±SEM. Statistical significance was determined by Mixed effect analysis (A-D) or two-sided Student's t-test (E-L). *P<0.05 vs. control.

Figure 16:
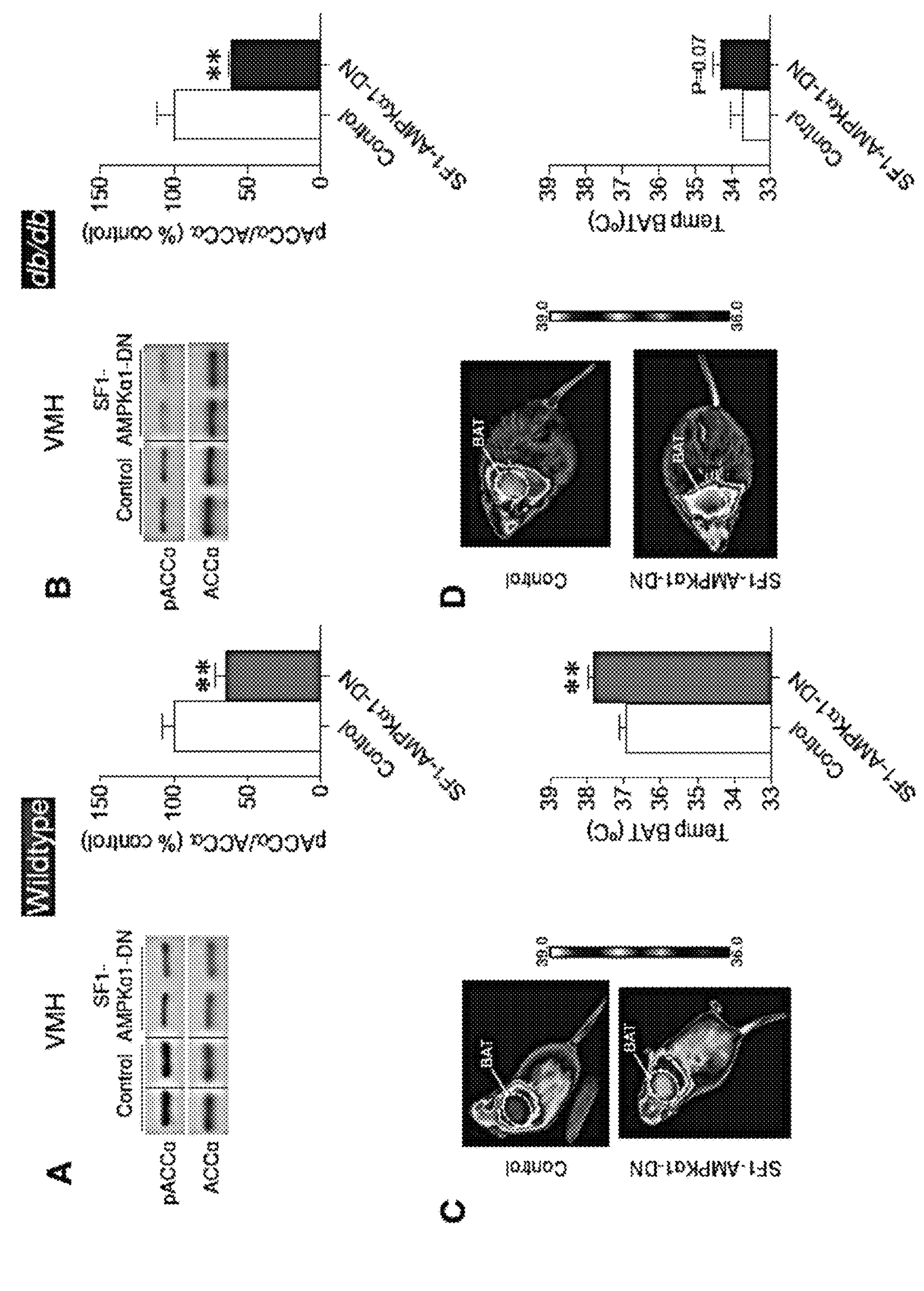
Figure 16:
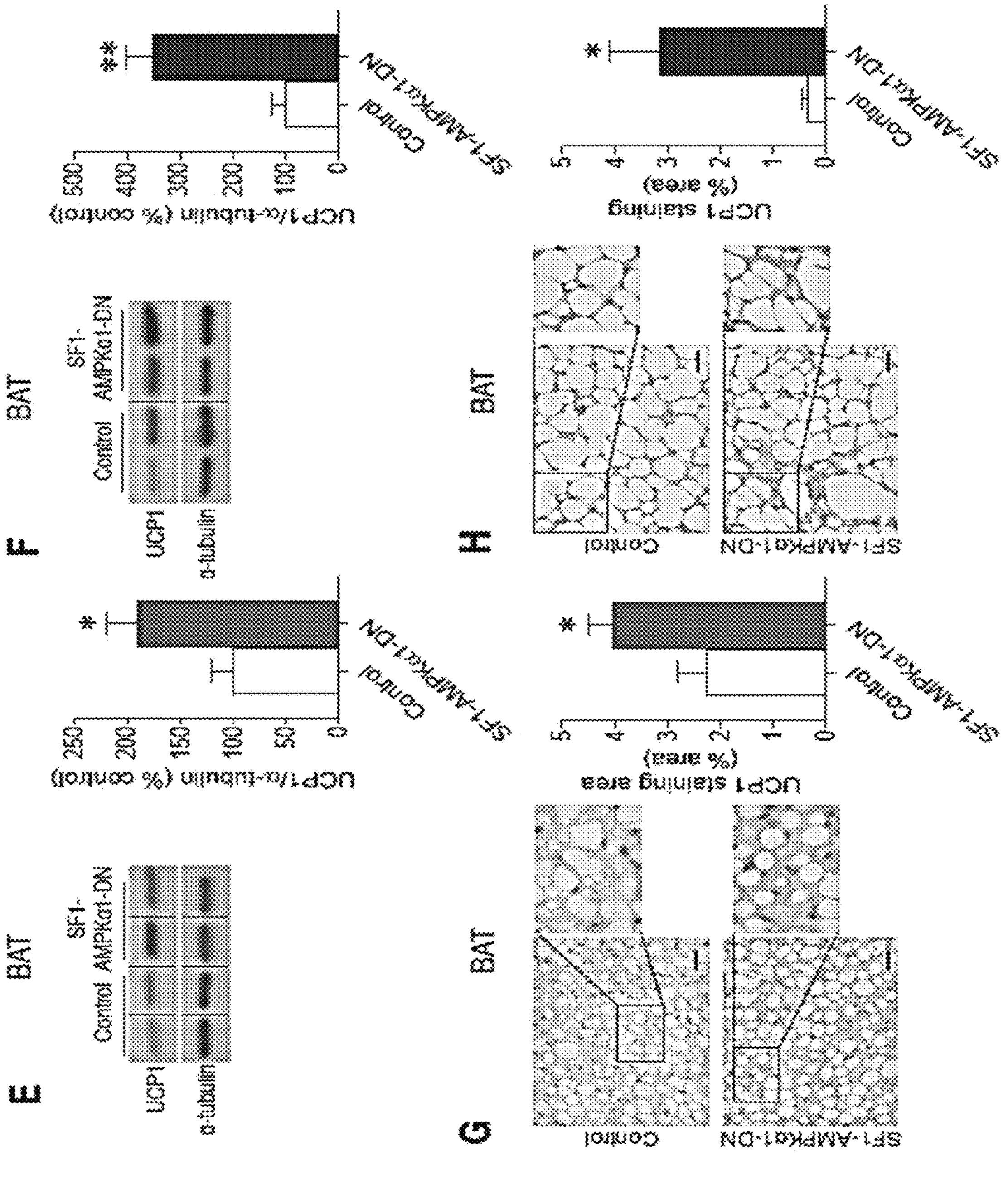
Figure 16:
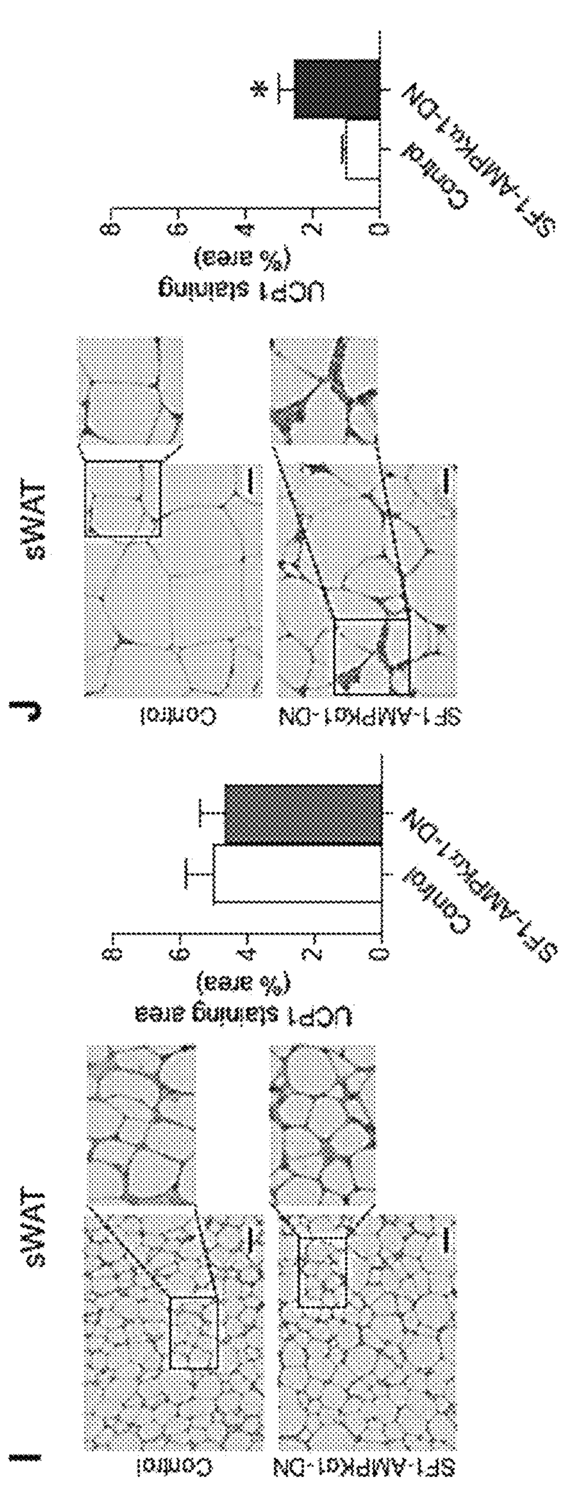

FIG. 16. Effect of systemic treatment with SF1-AMPKα1-DN loaded sEVs on BAT thermogenesis and WAT browning in db/db mice (A-B) Representative pACCα and ACCα western blot images and levels in the VMH (n=7 mice/group); (C-D) representative BAT thermographic images and BAT temperature (at day 14; n=7-8 mice/group); (E-F) representative UCP1 western blot images and levels in the BAT (n=6 mice/group); (G-H) representative BAT UCP1 staining and levels (n=7-8 mice/group) and (I-J) representative sWAT UCP1 staining and levels (n=7-8 mice/group) of wildtype and db/db mice intravenously injected with control or SF1-AMPKα1-DN loaded sEVs. In the western blot analyses (A-B and E-F) β-actin (in the VMH; not shown) and α-tubulin (in the BAT) were used as controls of protein loading. A black line was inserted on the immunoblots when samples were loaded on the same gel, but not side by side. Data are expressed as MEAN±SEM. Statistical significance was determined by two-sided Student's t-test, except for temperature of BAT in db/db mice (D) where one-side Student's t-test was used. *P<0.05, **P<0.01 vs. control.

BRIEF DESCRIPTION OF THE INVENTION

The present invention provides a population of small extracellular vesicles (sEVs) comprising at least one polynucleotide encoding a dominant negative AMP-activated protein kinase alpha 1 (AMPKα1-DN) mutant protein, wherein the amino acid sequence of the AMPKα1-DN mutant protein consists of SEQ ID NO: 1, 39, or 41; wherein said AMPKα1-DN mutant protein is operably linked and under the control of a steroidogenic factor 1 (SF1) promoter that has at least 98%, preferably 100%, sequence identity with SEQ ID NO: 3; and wherein the sEVs are engineered to express in their outer membrane at least one fusion protein comprising the neurotrophic rabies virus (RVG) peptide fused to lysosome-associated membrane protein 2b.

Preferably, the fusion protein comprising the neurotrophic rabies virus (RVG) peptide fused to lysosome-associated membrane protein 2b comprises SEQ ID NO: 5, or a sequence with at least 90% sequence identity to SEQ ID NO: 5.

Preferably, the population of sEVs is for use in the treatment or prevention of obesity, such as diet-induced obesity and/or genetic obesity. Preferably, the genetic obesity is leptin receptor (LEPR) deficiency-induced obesity.

Preferably, the population of sEVs is for use in the amelioration or reduction of the rebound effect after washout of the treatment of obesity, wherein, preferably, said amelioration or reduction of the rebound effect is measured at least 5 days after treatment washout.

Preferably, the administration of said small extracellular vesicles is systemic, preferably intravenous.

The present invention further provides a population of small extracellular vesicles (sEVs) capable of, when administered systemically, significantly decreasing the activation levels of AMP-activated protein kinase (AMPK) in SF1 expressing neurons located in the ventromedial nucleus of the hypothalamus (VMH) in comparison to the lack of effect on AMPK activity in untreated SF1 expressing cells, without said decrease being significantly reduced in other SF1 expressing tissues such as non-neuronal tissues/organs, preferably selected from the list consisting of adrenal glands, testicles, or pituitary gland; wherein said population of small extracellular vesicles (sEVs) comprises at least one polynucleotide encoding a dominant negative AMP-activated protein kinase alpha 1 (AMPKα1-DN) mutant protein, wherein the amino acid sequence of the AMPKα1-DN mutant protein consists of SEQ ID NO: 1, 39 or 41; wherein said AMPKα1-DN mutant protein is operably linked and under the control of a steroidogenic factor 1 (SF1) promoter that has at least 98%, preferably 100%, sequence identity with SEQ ID NO: 3, wherein the sEVs are engineered express in their outer membrane at least one fusion protein comprising the neurotrophic rabies virus (RVG) peptide fused to lysosome-associated membrane protein 2b, and wherein said population is for use in the treatment of obesity, preferably via the systemic route of administration, in a subject in need thereof.

Preferably, the nucleotide sequence of the AMPKα1-DN mutant protein consists of SEQ ID NO: 2. Preferably, the fusion protein comprising the neurotrophic rabies virus (RVG) peptide fused to lysosome-associated membrane protein 2b comprises SEQ ID NO: 5, or a sequence with at least 90% sequence identity to SEQ ID NO: 5.

Preferably, the use is in the amelioration or reduction of the rebound effect after washout of the treatment of obesity, wherein said amelioration or reduction of the rebound effect is measured at least 5 days after treatment washout. Preferably, the treatment comprises reverting or ameliorating obesity.

Preferably, the small extracellular vesicles have a size distribution of between 30 and 150 nm. Preferably, the sEVs are characterized by lacking the GRP94 marker. Preferably, the sEVs are produced or obtained from immature antigen presenting cells characterized by having a statistically significant reduced expression of at least one T-cell activator molecule in comparison to the expression of said T-cell activator molecule in a mature antigen presenting cell. Preferably, the antigen presenting cell is a dendritic cell, preferably JAWS II cell line, and wherein the at least one T-cell activator molecule is one or more T cell-activator molecule selected from the group consisting of major histocompatibility complex II (MHC-II), cluster of differentiation 80 (CD80) or cluster of differentiation 86 (CD86), or a combination thereof.

Preferably, the sEVs are exosomes.

GENERAL DEFINITIONS

It must be noted that, as used herein, the singular forms "a", "an", and "the", include plural references unless the context clearly indicates otherwise. Further, unless otherwise indicated, the term "at least" preceding a series of elements is to be understood to refer to every element in the series. Those skilled in the art will recognize or be able to ascertain using no more than routine experimentation, many equivalents to the specific embodiments of the invention described herein. Such equivalents are intended to be encompassed by the present invention.

The term "about" when referred to a given amount or quantity is meant to include deviations of plus or minus 10 percent.

As used herein, the conjunctive term "and/or" between multiple recited elements is understood as encompassing both individual and combined options. For instance, where two elements are conjoined by "and/or", a first option refers to the applicability of the first element without the second. A second option refers to the applicability of the second element without the first. A third option refers to the applicability of the first and second elements together. Any one of these options is understood to fall within the meaning, and therefore satisfy the requirement of the term "and/or" as used herein. Concurrent applicability of more than one of the options is also understood to fall within the meaning, and therefore satisfy the requirement of the term "and/or."

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or "including" or sometimes when used herein with the term "having". Any of the aforementioned terms (comprising, containing, including, having), whenever used herein in the context of an aspect or embodiment of the present invention may be substituted with the term "consisting of", though less preferred.

When used herein "consisting of" excludes any element, step, or ingredient not specified in the claim element. When used herein, "consisting essentially of does not exclude materials or steps that do not materially affect the basic and novel characteristics of the claim.

As used herein, the term "extracellular vesicles" (EVs), refers to lipid bilayer-bound vesicles released from living cells into the extracellular environment. These vesicles lack functional nuclei and cannot replicate. Traditionally, EVs can be roughly classified into two main subtypes regarding their characteristics and biogenesis pathway: ectosomes and small extracellular vesicles (sEVs). Ectosomes have a size distribution between 100 and 1000 nm and are generated by cytoplasmic membrane budding. sEVs, where exosomes are included, are smaller in diameter (usually between 30-150 nm) and released by the fusion of the multivesicular bodies (MVBs) with the plasma membrane. The components of sEVs indicate their cellular origin and potential biological functions. In the context of the present invention, it is preferred that the sEVs or exosomes are produced in antigen presenting cells, as is explained in detail below.

As used herein, the phrase "subject in need thereof" includes subjects, such as mammalian subjects, preferably humans, that would benefit from administration of the population of sEVs disclosed herein. The subject in need thereof can be a person attempting to lose weight, or in need of weight loss. The subject may be a female, preferably human female. Preferably, the subject is a male, more preferably a human male. More preferably, the subject is obese or in need of a treatment for obesity. The terms "individual", "patient" or "subject" are used interchangeably in the present application and are not meant to be limiting in any way. The "individual", "patient" or "subject" can be of any age, sex and physical condition.

"Nucleic acids," "nucleic acid molecules," "oligonucleotide," and "polynucleotide" are used interchangeably and refer to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix.

As used herein, the term "gene" or "coding sequence" refers to a polynucleotide sequence in vitro or in vivo that encodes a gene product. In some instances, the gene consists or consists essentially of coding sequence, that is, sequence that encodes the gene product.

As used herein, the term "AMP-activated protein kinase" (AMPK) refers to an enzyme that plays a role in cellular energy homeostasis, largely to activate glucose and fatty acid uptake and oxidation when cellular energy is low. It belongs to a highly conserved eukaryotic protein family. It consists of three proteins (subunits) that together make a functional enzyme, conserved from yeast to humans. It is expressed in a number of tissues, including the liver, brain, and skeletal muscle. In response to binding AMP and ADP, the net effect of AMPK activation is stimulation of hepatic fatty acid oxidation, ketogenesis, stimulation of skeletal muscle fatty acid oxidation and glucose uptake, inhibition of cholesterol synthesis, fatty acid synthesis, and triglyceride synthesis, inhibition of adipocyte lipogenesis, and modulation of insulin secretion by pancreatic beta-cells. AMPK is a heterotrimeric protein complex that is formed by α, β, and γ subunits. As used herein, "AMPKα" refers to the subunit alpha (α) of the AMPK protein. Due to the presence of isoforms of its components, there are 12 versions of AMPK in mammals, each of which can have different tissue localizations, and different functions under different conditions. The α, β, and γ subunits can also be found in different isoforms: the γ subunit can exist as either the γ1, γ2 or γ3 isoform; the β subunit can exist as either the β1 or β2 isoform; and the a subunit can exist as either the α1 or α2 isoform. As used herein, "AMPKα" refers to the isoform 1 of the subunit a of AMPK protein. As used herein, the term "dominant negative AMPKα1 mutant protein" (AMPKα1-DN) refers to an inactive isoform of the AMPKα1, preferably rat AMPKα1, protein by modification of its active site with at least the point mutation D168A, wherein the amino acid position (168) is expressed with respect to the wild-type rat AMPKα1 sequence, preferably the wild-type rat AMPKα1 sequence of SEQ ID NO: 40. In the context of the present invention, "AMPKα1-DN" refers to the inactive isoform of the AMPKα1, preferably rat AMPKα1, protein by modification of its active site with at least the point mutations D168 with respect to the wild-type rat AMPKα1 sequence, preferably the wild-type rat AMPKα1 sequence of SEQ ID NO: 40, wherein the sequence of the AMPKα1-DN protein can be the sequence of rat AMPKα1 protein (as shown in the Examples), or an homologous sequence of the rat AMPKα1 protein corresponding to the species where the treatment is applied, such as human homologous of AMPKα1 protein, or humanised or a codon-optimized AMPKα1 protein for treatment in humans. Alternatively, the rat sequence of AMPKα1 protein can be used to treat other species, such as humans, as it has been shown that rat AMPKα1-DN was effective in other animals such as mouse (see Seoane-Collazo et al, 2018, SF1-Specific AMPKα1 Deletion Protects Against Diet-Induced Obesity. Diabetes. 2018 November; 67(11):2213-2226) and human cells (Stein et al. 2000. The regulation of AMP-activated protein kinase by phosphorylation. Biochem. J. (2000) 345, 437-443). In case of using the AMPK human sequence, the sequence may also or alternatively comprise other point mutations, such as T172A mutation.

As used herein, the term "nuclear receptor steroidogenic factor-1 (SF-1)" refers to a transcription factor essential for terminal differentiation and maintenance of ventromedial nucleus neuronal populations.

As used herein, the term "SF1 expressing cell or tissue" refers to cells or tissues that are able to express the SF1 transcription factor. Preferably, the SF1 expressing cell is a SF1 expressing neuron located in the VMH region.

The hypothalamus is organized in anatomically distinct interconnected hypothalamic nuclei including the arcuate nucleus (ARC), the ventromedial nucleus (VMH), the paraventricular nucleus (PVH), the lateral hypothalamic area (LHA) and the dorsomedial nucleus (DMH) that among others, participate in the regulation of energy metabolism. Thus, as used herein, the term "ventromedial nucleus of the hypothalamus" (VMH) refers to a hypothalamic region. The VMH region is known for being involved in feeding behaviour and energy expenditure regulation via the brown adipose tissue (BAT) thermogenesis. The VMH is related to other nuclei through axonal projections.

As used herein, "pharmaceutically acceptable carrier" or "pharmaceutically acceptable diluent" means any and all solvents, dispersion media, coatings, antibacterial and antifungal agents, isotonic and absorption delaying agents, compatible with pharmaceutical administration. The use of such media and agents for pharmaceutically active substances is well known in the art. Acceptable carriers, excipients, or stabilizers are nontoxic to recipients at the dosages and concentrations employed and, without limiting the scope of the present invention, include: additional buffering agents; preservatives; co-solvents; antioxidants, including ascorbic acid and methionine; chelating agents such as EDTA; metal complexes (e.g., Zn-protein complexes); biodegradable polymers, such as polyesters; salt-forming counterions, such as sodium, polyhydric sugar alcohols; amino acids, such as alanine, glycine, glutamine, asparagine, histidine, arginine, lysine, ornithine, leucine, 2-phenylalanine, glutamic acid, and threonine; organic sugars or sugar alcohols, such as lactitol, stachyose, mannose, sorbose, xylose, ribose, ribitol, myoinisitose, myoinisitol, galactose, galactitol, glycerol, cyclitols (e.g., inositol), polyethylene glycol; sulphur containing reducing agents, such as urea, glutathione, thioctic acid, sodium thioglycolate, thioglycerol, [alpha]-monothioglycerol, and sodium thio sulphate; low molecular weight proteins, such as human serum albumin, bovine serum albumin, gelatin, or other immunoglobulins; and hydrophilic polymers, such as polyvinylpyrrolidone.

The positions or location of the amino acid residues of a protein or a polypeptide sequence are preferably numbered sequentially starting from the first amino acid residue which would then be located at position 1. For example, a protein of 137 amino acids will have those residues numbered 1 (first amino acid residue) until 137 (the last amino acid residue). Preferably, the first position or position number 1 corresponds to the first amino acid residue located at the 5-prime (5) end of the polypeptide chain that has a nitrogen atom or a free amino group. Thus, the numbering preferably starts from the first amino acid residue at the N terminal or 5' end of the protein or polypeptide and ends at the 3' end or C terminal end of the protein or polypeptide. Preferably, the positions of the amino acid residues are numbered using the amino acid sequence of the translated mature protein.

The terms "sequence identity" or "percent identity" in the context of two or more nucleotide sequences, polypeptide sequences or proteins sequences refers to two or more sequences or subsequences that are the same ("identical") or have a specified percentage of nucleotide or amino acid residues that are identical ("percent identity") when compared and aligned for maximum correspondence with a second molecule, as measured using a sequence comparison algorithm, preferably BLAST alignment tool, or alternatively, by visual inspection. The "sequence identity" or "percent identity" can be determined by calculating the number of identical nucleotides or amino acids at the same positions in a nucleic acid, polypeptide or protein. Calculation of percent identity includes determination of the optimal alignment between two or more sequences. Alignment can take into account insertions and deletions (i.e. "gaps") in each of the sequences to be tested, such as, without limitation, in the non-coding regions of nucleic acids and truncations or extensions of polypeptide sequences. Computer programs and algorithms such as the Basic Local Alignment Search Tool (BLAST) may be used to determine the percent identity. BLAST is one of the many resources provided by the U.S. National Center for Biotechnology Information. Because the genetic code is degenerate, and more than one codon can encode a given amino acid, coding regions of nucleic acids are considered identical if the nucleic acids encode identical polypeptides. Thus, percent identity could also be calculated based on the polypeptide encoded by the nucleic acid. Percent identity could be calculated based on full length consensus genomic sequences or on a fraction of the genomic sequence, such as for example without limitation on individual open reading frames (ORFs).

"Percent (%) amino acid sequence identity" with respect to proteins or polypeptides described herein is defined as the percentage of amino acid residues in a candidate sequence that are identical with the amino acid residues in the reference sequence (i.e., the protein or polypeptide from which it is derived), after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for example, using publicly available computer software such as BLAST. Those skilled in the art can determine appropriate parameters for measuring alignment, including any algorithms needed to achieve maximum alignment over the full-length of the sequences being compared.

Preferably, the "percentage of identity" as used herein is decided in the context of a local alignment, i.e., it is based on the alignment of regions of local similarity between nucleobase sequences, contrary to a global alignment, which aims to align two sequences across their entire span. Thus, in the context of the present invention, percentage identity is calculated preferably only based on the local alignment comparison algorithm.

DESCRIPTION

The aim of this study is to develop a new strategy for the treatment or prevention of obesity by specifically reducing the activity of hypothalamic AMPK in SF1 neurons. For this purpose, we used small extracellular vesicles (sEVs) as carriers of plasmids encoding a dominant negative AMPKα1 mutant (AMPKα1-DN). sEVs are derived from multivesicular bodies and contain proteins, lipids, and genetic information able to modify the phenotype and function of the target cells, which enables them to play a crucial role in physiology and pathophysiology. To confer specificity to the expression of this AMPKα1-DN mutant only in hypothalamic SF1 expressing neurons, the SF1 promoter was used to drive its expression. Notably, to avoid any invasive cranial surgery/procedure, the objective of this study was also to target specifically AMPK within hypothalamic SF1 neurons using systemic administration routes and making them affordable for potential therapeutic use.

The present invention thus provides SF1-AMPKα1-DN loaded sEVs administered systemically for use in treatment or prevention of obesity. Immature dendritic cells were used to generate large quantities of sEVs. To confer neuronal targeting capacities to the produced sEVs, immature dendritic cells were genetically modified to transiently express a fusion protein composed of (i) lysosome-associated membrane protein 2b (Lamp2b), a protein highly expressed in sEV membranes, fused to (ii) a specific glycoprotein derived from the neurotrophic rabies virus (RVG) that enables the blood brain barrier (BBB) crossing through its binding to the nicotinic acetylcholine receptor (nAChR).

Figure 2:
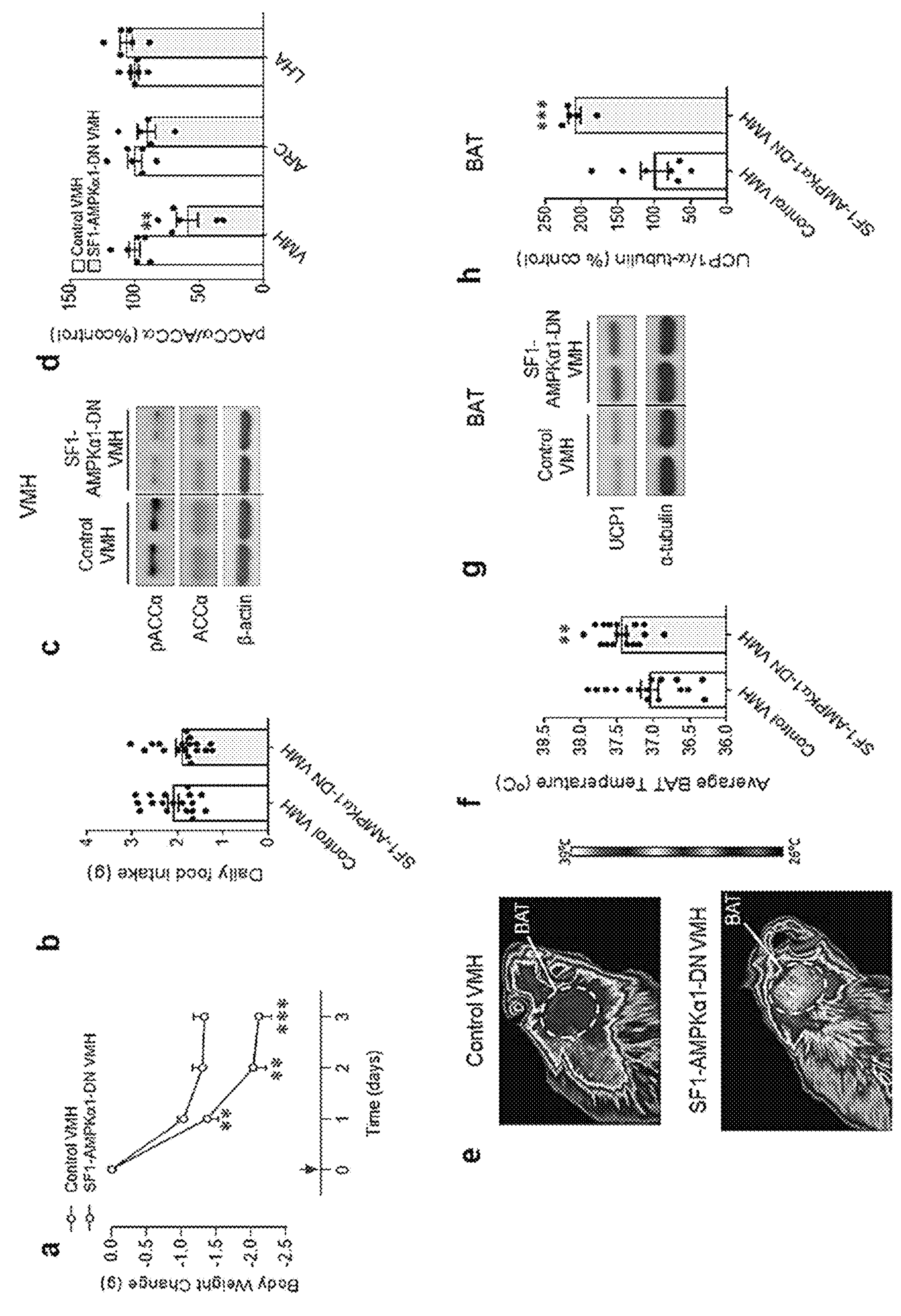
FIG. 2. Effect of stereotaxic VMH injection of SF1-AMPKα1-DN loaded sEVs on energy balance. (a) Body weight changes expressed in grams of mice after stereotaxic VMH injection with control (non-loaded) or SF1-AMPKα1-DN loaded sEVs. The red arrow indicates the onset of injections (n=18 animals per group). (b) Daily food intake expressed in grams of mice after stereotaxic VMH injection with control (non-loaded) or SF1-AMPKα1-DN loaded sEVs (n=18 animals per group). (c) Representative pACCα and ACCα western blot images in VMH harvested from mice after 72 h of stereotaxic VMH injection with control (non-loaded) or SF1-AMPKα1-DN loaded sEVs. ß-actin was used as control of protein loading. A black line was inserted on the immunoblots when samples were loaded on the same gel, but not side by side. (d) Quantification of pACCα/ACCα expressed in % of control in VMH, arcuate nucleus (ARC) and lateral hypothalamic area (LHA) (n=5-6 mice/group). (e, f) Representative thermographic images (e) and BAT interscapular temperature quantification (average of the 3 days) (f) of mice after 72 h of stereotaxic VMH injection with control (non-loaded, n=16 animals per group) or SF1-AMPKα1-DN loaded sEVs (n=17 animals per group). (g) Representative UCP1 western blot images of BAT harvested from mice after 72 h of stereotaxic VMH injection with control (non-loaded) or SF1-AMPKα1-DN loaded sEVs. α-tubulin was used as control of protein loading. A black line was inserted on the immunoblots when samples were loaded on the same gel, but not side by side. (h) Quantification of UCP1 protein expression of BAT harvested from mice after 72 h of stereotaxic VMH injection with control (non-loaded) or SF1-AMPKα1-DN loaded sEV. (n=5-7 mice/group). Data expressed as mean±SEM. P<0.01 and *P<0.001 vs. Control. Statistical significance was assessed by two-sided Student's t-test.
Figure 3:
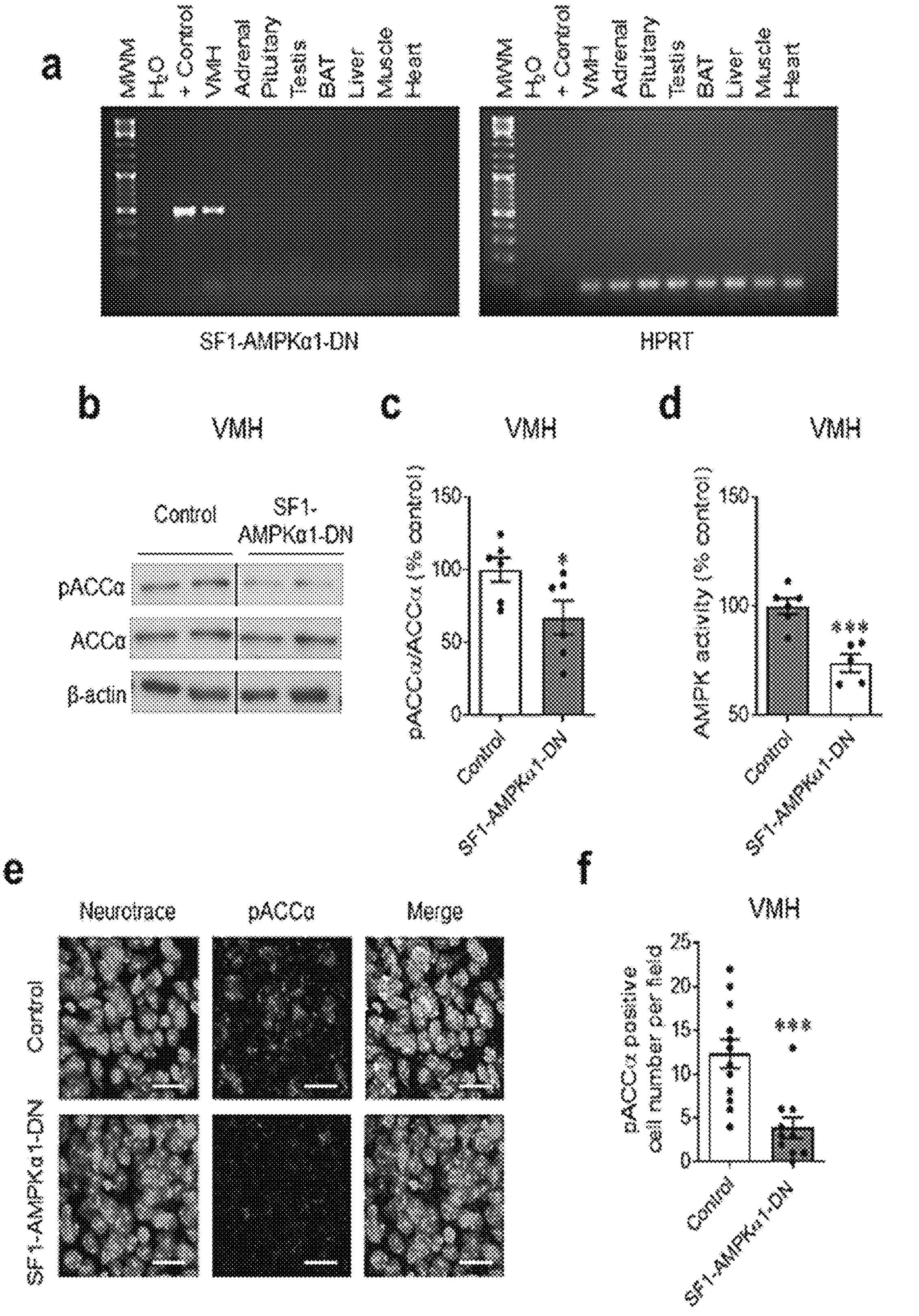
FIG. 3. Effect of systemic treatment with SF1-AMPKα1-DN loaded sEVs on hypothalamic AMPK activity. (a) SF1-AMPKα1-DN plasmid in vivo expression at 24 h in mice injected intravenously with SF1-AMPKα1-DN loaded sEVs. Representative agarose gel electrophoresis using specific SF1-AMPKα1-DN and HPRT primers. +Control being the SF1-AMPKα1-DN plasmid. (b) Representative pACCα and ACCα western blot images and quantification of pACCα in the VMH after 72 h of intravenous injection with control (non-loaded, n=6 mice/group) or SF1-AMPKα1-DN loaded sEVs (n=6 mice/group). β-actin was used as control of protein loading. A black line was inserted on the immunoblots when samples were loaded on the same gel, but not side by side. (c) Quantification of pACCα/ACCα expressed in % of control in VMH. (d) Quantification of AMPK activity in the VMH after 72 h of intravenous injection with control (non-loaded, n=6 mice/group) or SF1-AMPKα1-DN loaded sEVs (n=5 mice/group). (e, f) Representative images depicting Neurotrace 500/525 (green), pACCα (magenta)-positive cells and merged reactivity (e) and quantification (f) of pACCα positive cell number (quantification per field; 10-12 fields, 4 mice/group) in the VMH after 24 h of intravenous injection with control (non-loaded) or SF1-AMPKα1-DN loaded sEVs. Scale bars represent 20 μm. (g, h) Representative confocal images depicting DAPI (blue), SF1 (red), pACCα (green) and merged reactivity (g) and quantification of pACCα fluorescence (h) in SF1 cells (quantification per field; 2-3 fields, 4 mice/group) in the VMH after 24 h of intravenous injection with control (non-loaded) or SF1-AMPKα1-DN loaded sEVs (h). Arrows indicate pACC-positive SF1 cells. Scale bars represent 20 μm. (i, j) Time course of SF1-AMPKα1-DN plasmid expression in the VMH following one intravenous injection. Representative agarose gel electrophoresis using specific SF1-AMPKα1-DN and HPRT primers (i) and quantification of SF1-AMPKα1-DN plasmid expression in the VMH j) at different time points (n=4-5 mice/group). MWM, molecular weight marker. Data expressed as mean±SEM. *P<0.05, P<0.01 and *P<0.001, vs. Control. Statistical significance was assessed by two-sided Student's t-test.
Figure 3:
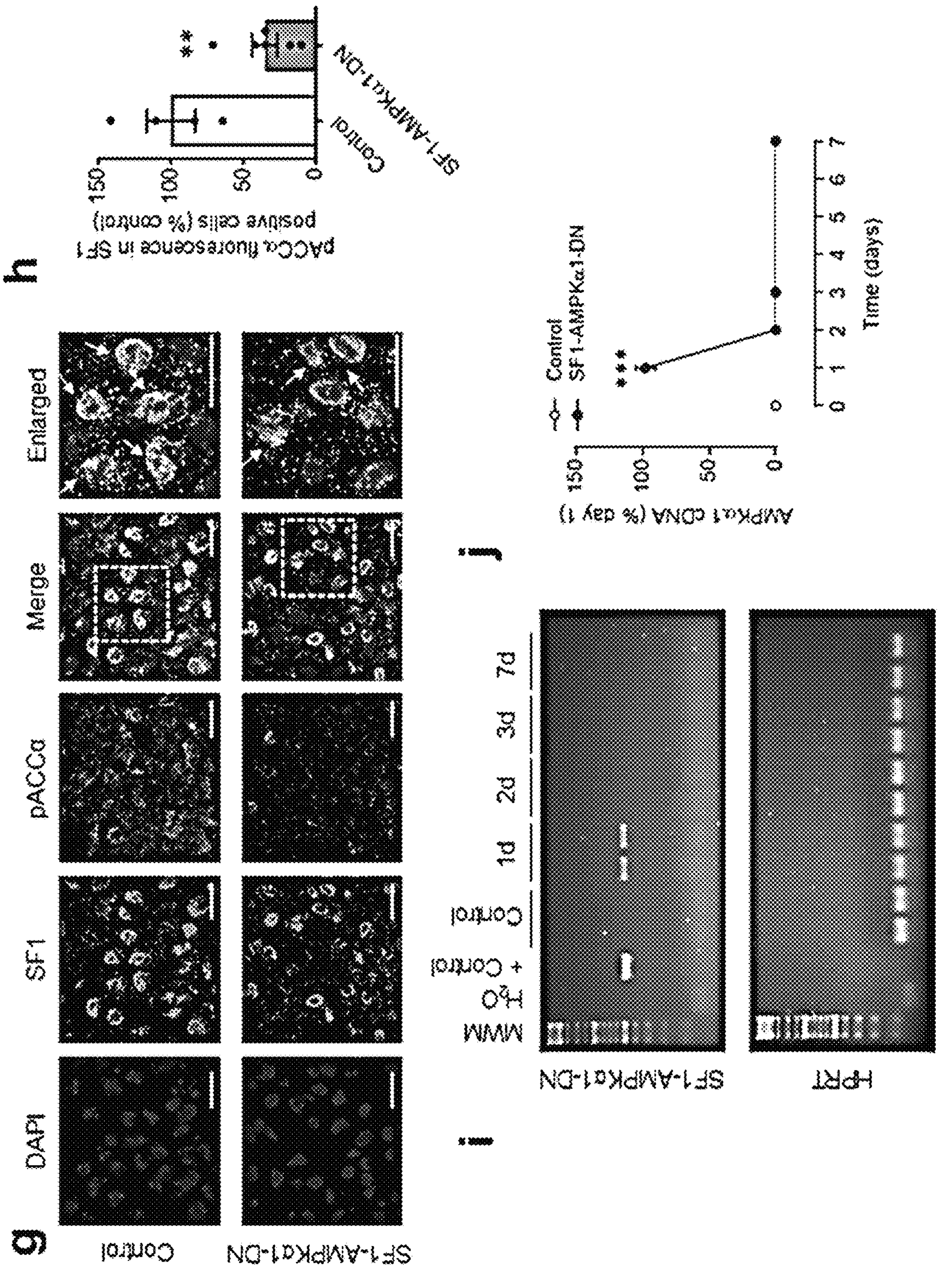

To study the efficacy of this strategy, the phosphorylated levels of acetyl-CoA carboxylase alpha (pACCα), which is a regulatory kinase that is a main target of the enzyme AMPK, were measured in obese mice treated with Lamp2b-RVG sEVs loaded with SF1-AMPKα1-DN via central and systemic administration routes. The results demonstrated that SF1-AMPKα1-DN sEVs induced a feeding-independent weight loss. The levels of pACCα, used to control the extent of AMPK inhibition, in hypothalamic extracts were also reduced specifically in the VMH area, but not in the ARC or LHA areas, and this was associated with increased BAT thermogenesis (FIG. 2). Upon systemic administration, the transgene was only detected in VMH samples, but not in any of the other evaluated organs including those expressing SF1 (i.e., adrenal, pituitary and testis), or those not expressing SF1 (i.e., BAT, liver, skeletal muscle and heart) (FIG. 3*a*), indicating that the effect of this treatment is restricted to neuronal cells, particularly the SF1-expressing neurons of the VMH, and demonstrating that this strategy is highly specific. Further, SF1-AMPKα1-DN loaded sEVs induced a significant decrease in the levels of phosphorylation of ACCα and AMPK activity in the VMH (FIG. 3).

Figure 4:
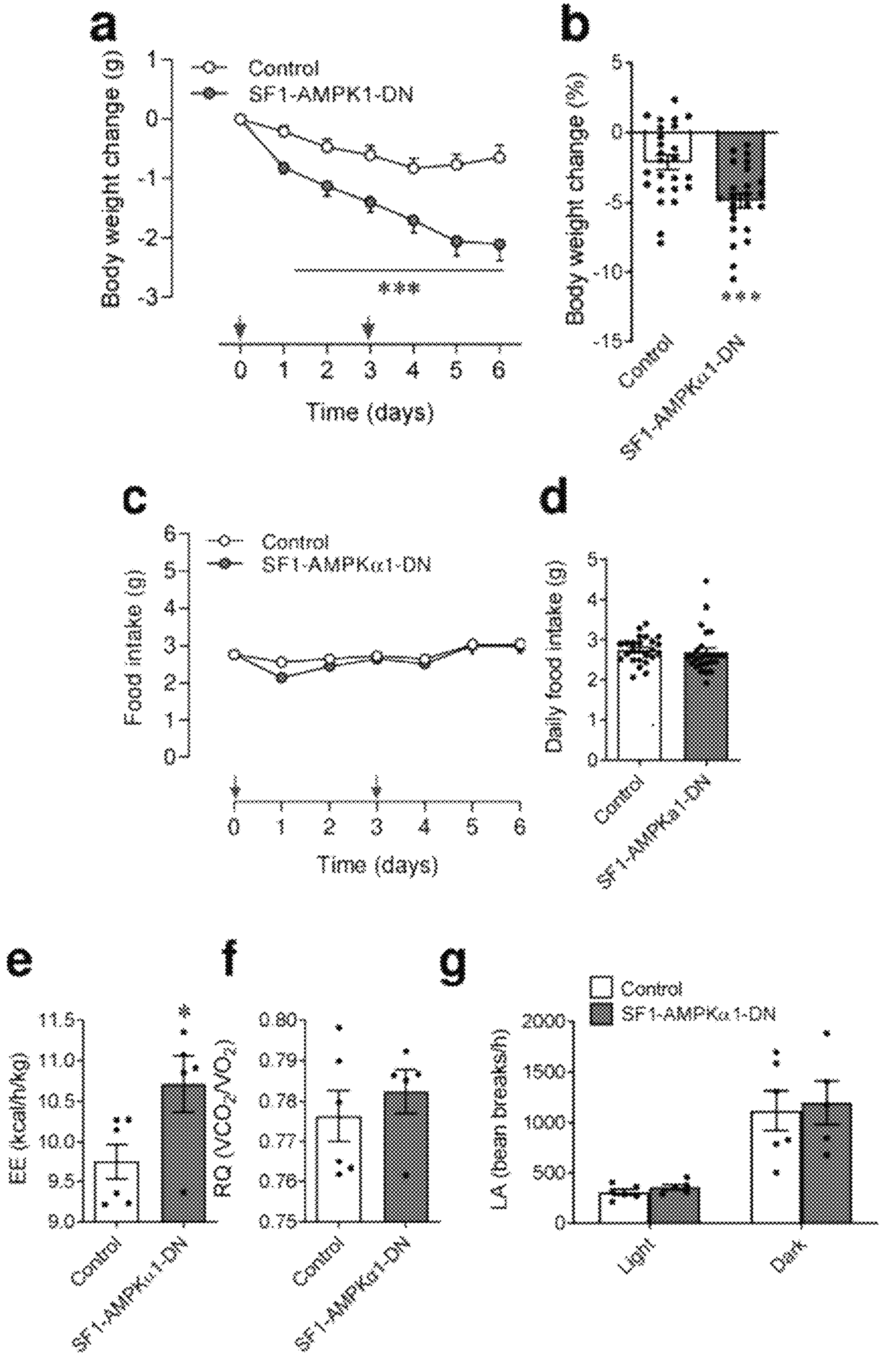
FIG. 4. Effect of systemic treatment with SF1-AMPKα1-DN loaded sEVs on energy balance. (a, b) Body weight changes expressed in grams (a) and percentage (b) of mice after intravenous injection with control (non-loaded) or SF1-AMPKα1-DN loaded sEVs every 3 days for 6 days. Red arrows indicate the injections (n=24-25 mice/group). (c) Food intake expressed in grams of mice after intravenous injection with control (non-loaded) or SF1-AMPKα1-DN loaded sEVs each 3 days for 6 days. Red arrows indicate the injections (n=25 mice/group). (d) Daily food intake expressed in grams of mice after intravenous injection with control (non-loaded) or SF1-AMPKα1-DN loaded sEVs each 3 days for 6 days (n=25 mice/group). (e-g) Energy expenditure (EE, e), respiratory quotient (RQ, f) and locomotor activity (LA, g) during light and dark phases of mice after intravenous VMH injection with control (non-loaded, n=6 mice/group) or SF1-AMPKα1-DN loaded sEVs (n=5 mice/group) each 3 days for 6 days. (h) Representative NMR images showing adipose tissue (AT) on images with (AT on) and without fat (AT off), total AT obtained subtracting AT on by AT off, subcutaneous AT (scAT) and visceral AT (VAT) of mice after intravenous VMH injection with control (non-loaded, n=7 mice/group) or SF1-AMPKα1-DN loaded sEVs (n=8 mice/group) each 3 days for 6 days. (i-k) Quantification of AT mass expressed in grams; total AT mass (i), scAT j) and vAT (k) of mice after intravenous VMH injection with control (non-loaded, n=7 mice/group) or SF1-AMPKα1-DN loaded sEVs (n=8 mice/group) every 3 days for 6 days. (1, n) Body weight (1) and body weight changes expressed in grams (m) and percentage (day28-d1) (n) of mice after intravenous injection with control (non-loaded) or SF1-AMPKα1-DN loaded sEVs every 3 days for 28 days (n=15 mice/group) and then 14 days of washout (n=8 mice/group). Red arrows indicate the injections. (o, p) Food intake (o) and daily food intake (p) of mice after intravenous injection with control (non-loaded) or SF1-AMPKα1-DN loaded sEVs every 3 days for 28 days and then 14 days of washout (n=15 mice/group). Red arrows indicate the injections. (q-s) Body weight changes expressed in grams during all period of treatment (q) and during of each week of treatment (r) of mice after intravenous injection with control (non-loaded) or SF1-AMPKα1-DN loaded sEVs every 3 days for 6 days, then 2 weeks of washout and again injections every 3 days for 6 days. Food intake expressed in grams (s) of mice after intravenous injection with control (non-loaded, n=7 mice/group) or SF1-AMPKα1-DN loaded (n=7 mice/group) sEVs following the same protocol. Red arrows indicate the injections. Data expressed as mean±SEM. *P<0.05, P<0.01 and *P<0.001 vs. Control. Statistical significance was assessed by two-sided Student's t-test.
Figure 4:
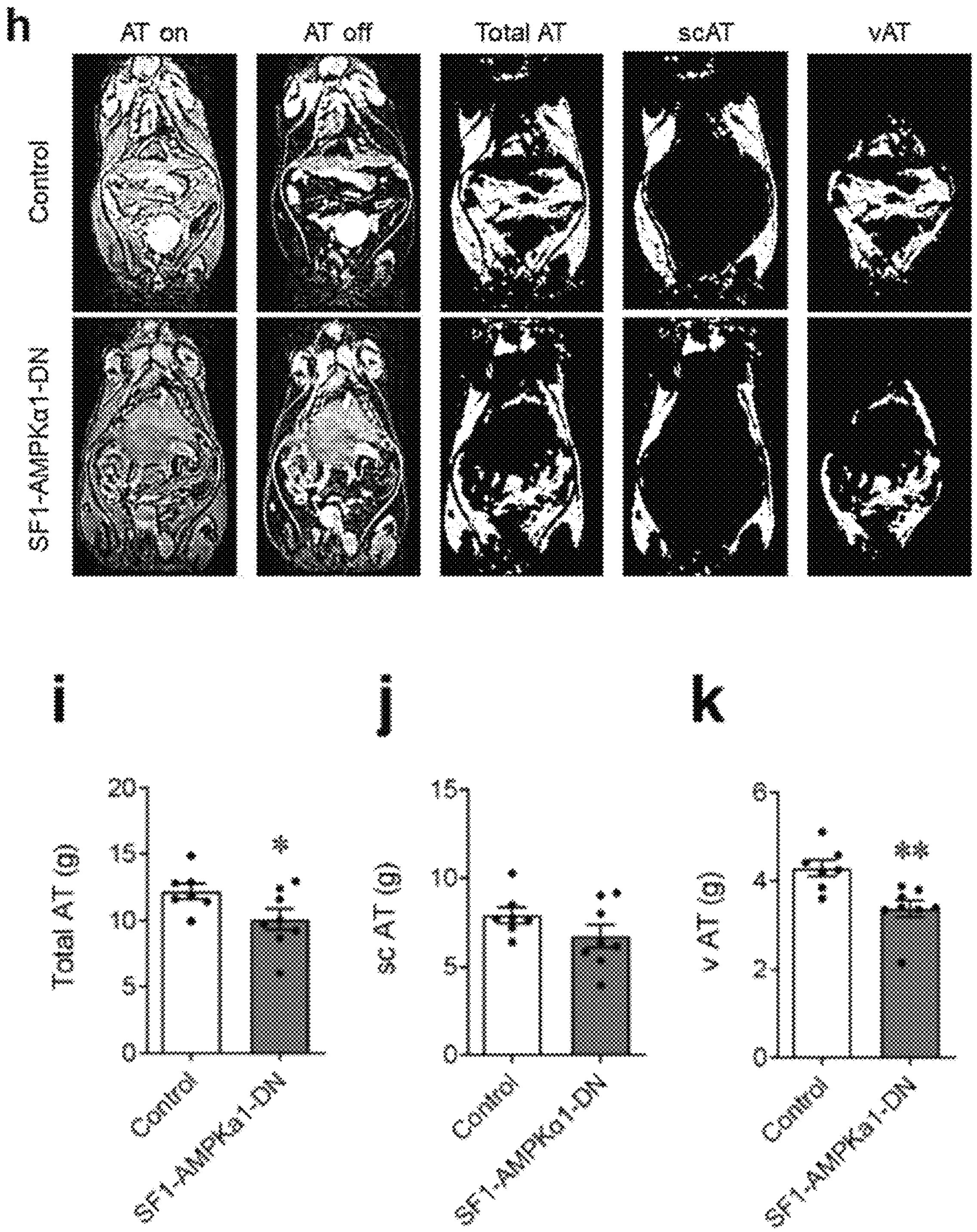
Figure 4:
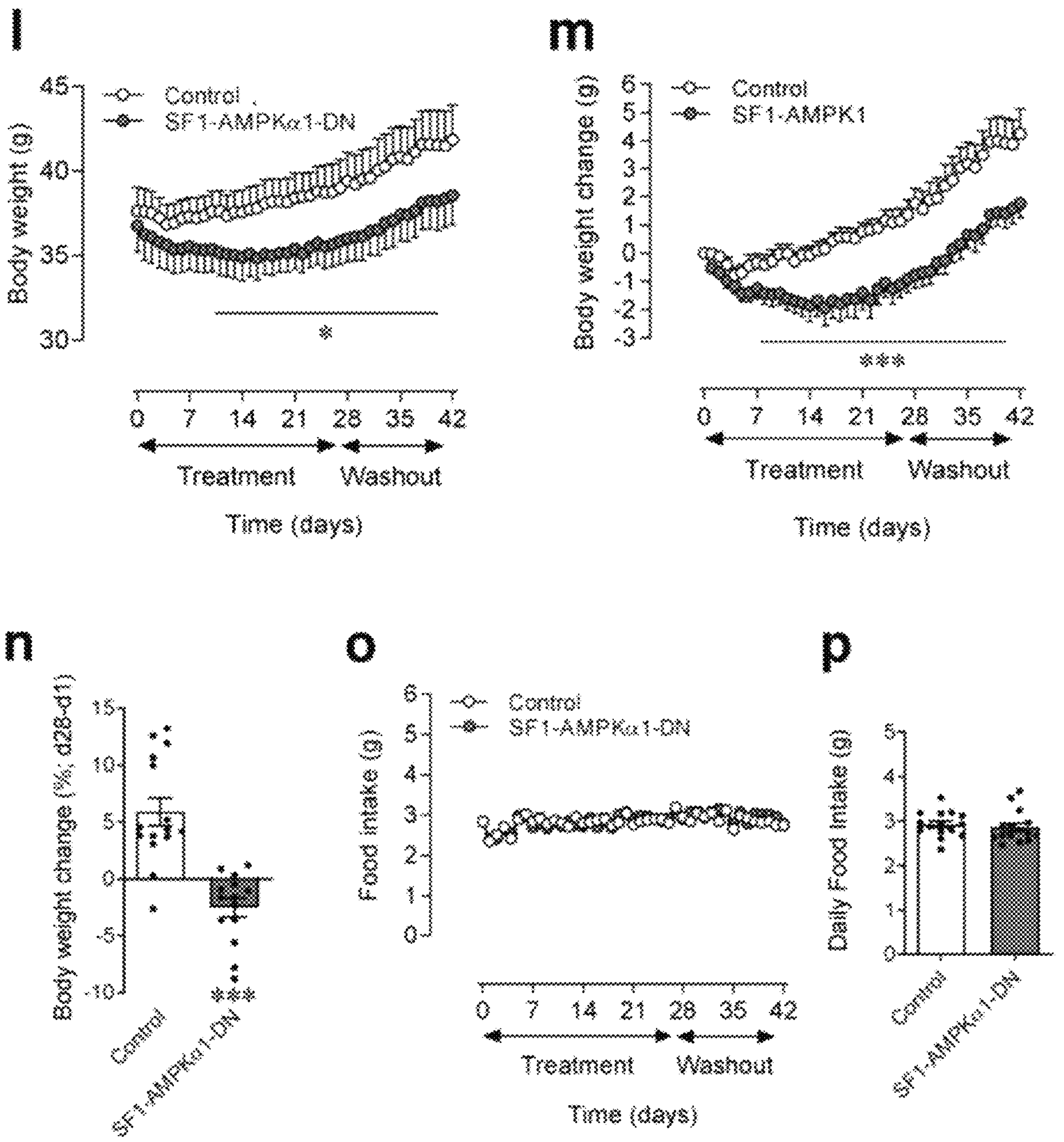
Figure 4:
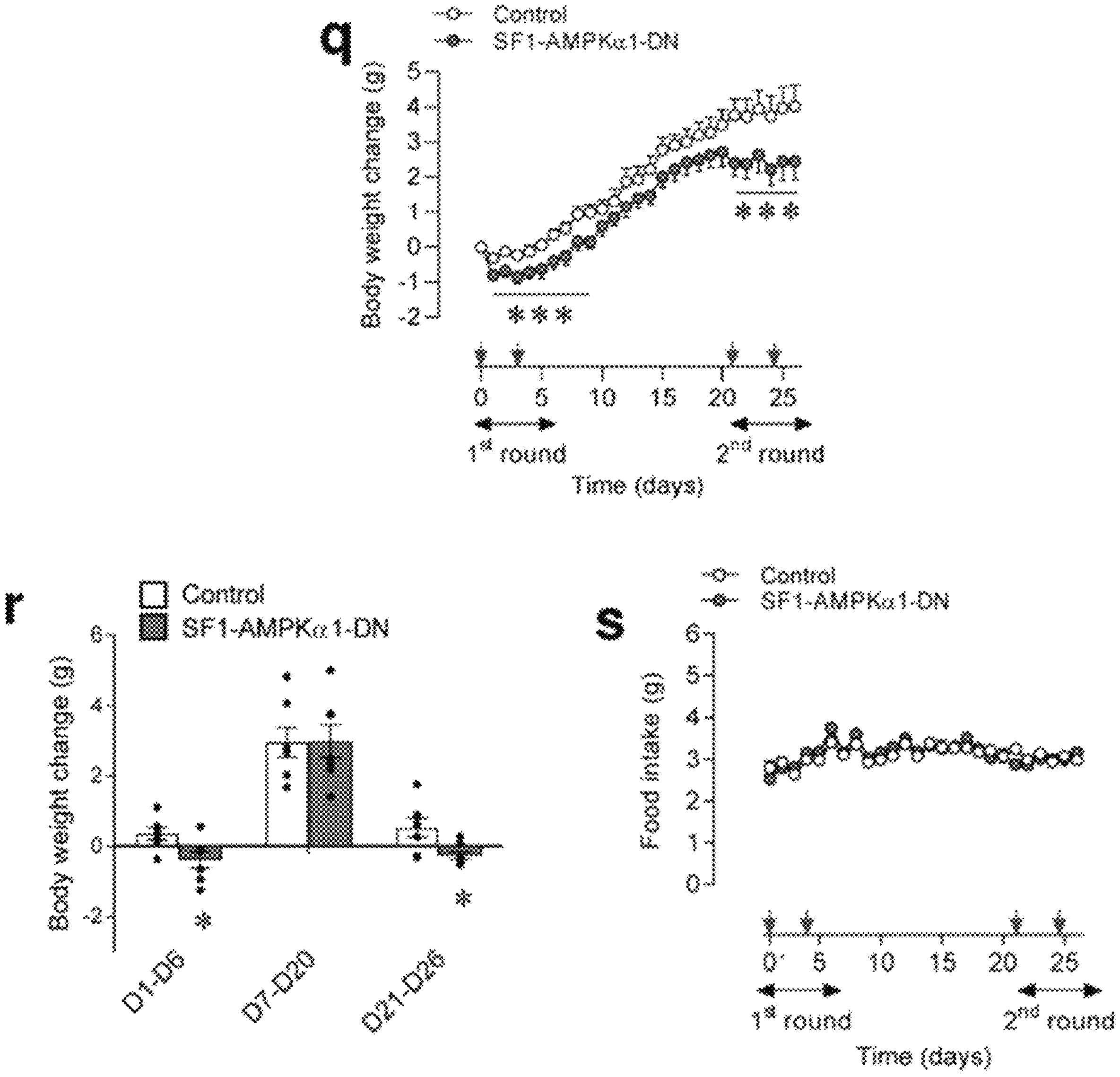

Additionally, we studied if the treatment with sEVs in obese mice had a rebound effect, namely a quick recovery of the lost weight to catch up with the weight of control mice. FIG. 4 shows that the effect of sEVs was sustained when the treatment was withdrawn. Mice treated with SF1-AMPKα1-DN loaded sEVs did not exhibit any catch up in their body weight up until 2 weeks after the injections were ceased (washout), when compared to mice treated with control sEVs. This indicates that the body weight loss is not transient, and a washout period does not imply a rebound effect in treated mice.

Altogether, these data support the suitability of the Lamp2b-RVG sEVs loaded with SF1-AMPKα1-DN mutants to specifically downregulate or inhibit AMPK activity in specific SF1 expressing neurons in order to induce weight loss and therefore the sEVs represent a potential therapeutic strategy to treat or prevent obesity.

In a first aspect, the present invention relates to the systemic administration of a population of small extracellular vesicles (sEVs) for use in the treatment or prevention of obesity in a subject in need thereof. Particularly, in a first aspect, the present invention relates to the systemic administration of a population of sEVs for use in the treatment or prevention of obesity in a subject in need thereof, wherein the sEVs comprise at least one polynucleotide encoding an AMPK protein, preferably AMPKα, preferably AMPKα1, most preferably AMPKα1-DN (dominant negative AMP-activated protein kinase alpha 1 mutant) protein operably linked and under the control of a steroidogenic factor 1 (SF1) promoter; and wherein the sEVs, are engineered to express, preferably transiently, in their outer membrane at least one fusion protein comprising the neurotrophic rabies virus (RVG) peptide fused to lysosome-associated membrane protein 2b (Lamp2b). A coding sequence and a gene expression control sequence or promoter are said to be operably linked when they are linked in such a way as to place the expression or transcription and/or translation of the coding sequence under the influence or control of the gene expression control sequence. For example, the dominant negative AMPKα1 mutant protein (AMPKα1-DN) is operably linked to the SF1 promoter so that the expression levels of the AMPKα1-DN are regulated by the SF1 promoter. In an embodiment, the obesity is diet-induced obesity and/or genetic obesity. In an embodiment, the obesity is genetic obesity, preferably leptin receptor (LEPR) deficiency-induced obesity.

Preferably, the population of sEVs are exosomes. In an embodiment, the population of sEVs or exosomes is a substantially pure population. Preferably, the sEVs or exosomes are isolated. In the context of the present invention, the term "isolated" indicates that the sEVs or exosomes or population thereof is not within the environment or cell culture where they were produced. The sEVs or exosomes or population thereof has been substantially separated from surrounding environment or cell culture. In some embodiments, the population is substantially pure or enriched in sEVs or exosomes and comprises at least about 50%, 55%, 60%, 70%, 75%, 80%, 85%, 90%, 95%, 98%, or 100% of sEVs or exosomes. In an embodiment, the population is pure in sEVs or exosomes. They are released by many cell types as a means of communicating with other cells and thus cell content may be potentially removed from the population. The cargo of extracellular vesicles includes the proteins, lipids, nucleic acids, and membrane receptors of the cells from which they originate. The term isolated also encompasses a population of sEVs or exosomes that have been removed from the environment or ell culture, e.g., from the supernatant or conditioning media, from which they originated.

In an embodiment, the sEVs or exosomes are spherical or round-shaped. Further, the sEVs or exosomes may have a size of greater than 2 nm. The sEVs or exosomes may have a size of greater than 5 nm, 10 nm, 20 nm, 30 nm, 40 nm, 50 nm, 60 nm, 70 nm, 80 nm, 90 nm, 100 nm, 110 nm, 120 nm, 130 nm, 140 nm, 150 nm or 160 nm. The exosome may have a size of substantially 160 nm or greater. The sEVs or exosomes may have a range of size distribution, such as between 30 nm to 50 nm, 30 nm to 100 nm, preferably 30 nm to 150 nm or 30 nm to 200 nm. The size distribution may be determined by various means. In principle, the size may be determined by size fractionation and filtration through a membrane with the relevant size cut-off. The sEVs or exosomes size may then be determined by tracking segregation of component proteins with SDS-PAGE or by a biological assay. The size may also be determined by electron microscopy or by Nanoparticle tracking analysis (NTA).

The population of sEVs or exosomes provided herein comprise or are loaded with at least one polynucleotide comprising a gene encoding an AMPK protein, preferably AMPKα, preferably AMPKα1, most preferably AMPKα1-DN mutant protein, wherein said gene is operably linked and under the control of a SF1 promoter. Preferably, each of the sEVs of the population is loaded with at least one polynucleotide comprising a gene encoding an AMPK protein, preferably AMPKα, preferably AMPKα1, most preferably AMPKα1-DN mutant protein, wherein said gene is operably linked and under the control of a SF1 promoter. Preferably, the at least one polynucleotide is DNA, more preferably a plasmid. Thus, designing a plasmid encoding for AMPK-DN under the control of SF-1 (SF1-AMPK-DN plasmid) will allow the AMPK-DN to be expressed only in the SF1 expressing neurons located in the VMH. Once the sEVs or exosomes are fused with the target cells, the AMPK protein, preferably AMPKα, preferably AMPKα1, most preferably AMPKα1-DN mutant protein would only be expressed if the target cell, which is preferably a SF1 expressing neuron located in the ventromedial nucleus of the hypothalamus (VMH). The techniques used to load sEVs with various cargo include free-thaw cycles to fuse sEVs and liposomes, sonication, extrusion, permeabilization with saponin, and electroporation. Several commercial kits are available for loading nucleic acids into sEVs and the skilled person would be familiar with them. Preferably, the at least one polynucleotide, preferably a plasmid, is mainly located in the core of the sEVs or exosomes.

In an embodiment, the AMPK protein, preferably AMPKα, preferably AMPKα1, most preferably AMPKα1-DN mutant protein comprised in the polynucleotide of the sEVs comprises at least the mutation or amino acid substitution D168A, wherein the amino acid numbering is expressed with respect to the AMPKα1 protein of rat, preferably with respect to the wild-type rat AMPKα1 sequence of SEQ ID NO: 40. In an embodiment, the nucleotide or amino acid sequence of the AMPK, AMPKα, AMPKα1, AMPKα1-DN proteins is the rodent, preferably mouse, sequence. In another embodiment, the nucleotide or amino acid sequence of the AMPK, AMPKα, AMPKα1, AMPKα1-DN sequences is the human homologue sequence, or a humanized or human codon-optimized version of the mouse sequence. In an embodiment, the AMPKα1-DN mutant protein encoded by the at least one polynucleotide comprised in the sEVs or exosomes comprises, consists, or consists essentially of an amino acid sequence with at least 50%, 60%, 70%, 75%, 80%, 85%, 90%, 91%, 92%, 93%, 94%, 95%, 96%, 97%, 98%, or 100% sequence identity, over its full length, with SEQ ID NO: 1. In an embodiment, the at least one polynucleotide encoding for the AMPKα1-DN mutant protein comprises, consists, or consists essentially of polynucleotide sequence with at least 50%, 60%, 70%, 75%, 80%, 85%, 90%, 91%, 92%, 93%, 94%, 95%, 96%, 97%, 98%, or 100% sequence identity, over its full length, with SEQ ID NO: 2.

In an embodiment, the steroidogenic factor 1 (SF1) polynucleotide sequence also comprised in the at least one polynucleotide comprised in the sEVs or exosomes comprises, consists, or consists essentially of a sequence with at least 50%, 60%, 70%, 75%, 80%, 85%, 90%, 91%, 92%, 93%, 94%, 95%, 96%, 97%, 98%, or 100% sequence identity, over its full length, with SEQ ID NO: 3.

In an embodiment, the at least one polynucleotide encoding an AMPKα1-DN mutant protein operably linked and under the control of the SF1 promoter comprises, consists, or consists essentially of a polynucleotide sequence with at least 50%, 60%, 70%, 75%, 80%, 85%, 90%, 91%, 92%, 93%, 94%, 95%, 96%, 97%, 98%, or 100% sequence identity, over its full length, with SEQ ID NO 4.

The sEVs or exosomes provided herein further comprise or are loaded with, preferably mainly at their outer membrane, a fusion protein comprising or consisting of the neurotrophic rabies virus (RVG) peptide fused to lysosome-associated membrane protein 2b (Lamp2b), wherein said fusion protein comprises, consists or consists essentially of an amino acid sequence with at least 50%, 60%, 70%, 75%, 80%, 85%, 90%, 91%, 92%, 93%, 94%, 95%, 96%, 97%, 98%, or 100% sequence identity, over its full length, with SEQ ID NO 5. By "fusion protein" is referred herein as to a protein formed by at least two domains, wherein the at least two domains have been joined, one after the other, so that they are synthetized or translated as a single unit, and thus the two domains of the fusion protein are part of a single polypeptide. In this particular case, the domains comprised or consisting of the fusion protein are the RVG peptide and the Lamp2b protein. In an embodiment, the domains of a fusion protein may be linked by a linker peptide. "Linker peptide" as used herein is a short peptide sequence that is located between the domains of a fusion protein. Linker peptides are placed to provide the two domains comprised in the fusion protein with movement flexibility. In the context of the present invention, the linker peptide has at least one amino acid residue, preferably at least two consecutive amino acid residues, optionally 3, 4, 5, 6, 7, 8, 9, 10, 11, 12, 13, 14, 15, 16, 17, 18, 19, 20 or 20 more amino acid residues. The linker peptide includes flexible linkers, rigid linkers, and in vivo cleavable linkers.

The population of sEVs or exosomes described herein are characterized by comprising at least one Lamp2b-RVG fusion protein. For that purpose, a Lamp2b-RVG plasmid, such as the one designed as previously described in reference 28 (see the examples of the present specification), can be transfected in exosome generating-cells, preferably in exosome generating-immature dendritic cells, to transiently express the fusion protein comprising the neurotrophic rabies virus (RVG) peptide fused to lysosome-associated membrane protein 2b, wherein, preferably, such fusion protein comprises an amino acid sequence with at least 95% sequence identity, over its full length, with SEQ ID NO 5. In an embodiment, the sEVs or exosomes further comprise markers derived from the cells used to produced them (hereinafter referred to as producer cell). Preferably, the producer cells are immune cells, more preferably antigen presenting cells, even more preferably dendritic cells. Preferably, the producer cells are mammalian cells. The producer cell may be a primary cell or an immortalized cell. In an embodiment, the producer cell is a cell with low immunogenicity, preferably an immature immune cell, preferably an immature antigen presenting cell, most preferably an immature dendritic cell or monocyte. By "immature" is referred herein as a cell that is not activated or biologically active, or that does not present activation markers or molecule in the surface. An immature dendritic cell has different morphological phenotype than the mature one. Immature dendritic cells have a round and smooth surface, while mature cells, such as mature dendritic cells, have a rough surface with multiple pseudopodia. Immature dendritic cells produce large quantities of exosomes devoid of T-cell activators such as MHC-II, CD80 and CD86. Thus, in an embodiment, the producer cell, preferably the immature dendritic cell, does not express activation markers, preferably T-cell activator markers or molecules such as major histocompatibility complex II (MHC-II), cluster of differentiation 80 (CD80) or cluster of differentiation 86 (CD86), or a combination thereof. In an embodiment, the producer cell is an immature immortalized cell, preferably an immature immortalized dendritic cell or monocyte, most preferably the JAWS II cell line from the American Type Culture Collection CRL-1194; ATCC; Manassas, VA, USA or a cell derived from said JAWS II cell line. Also, preferably, the producer cell is a genetically modified cell that expresses the RVG-Lamp2b fusion protein, preferably in its outer membrane. In an embodiment, the producer cell is an immature antigen presenting cell characterized by having a statistically significant reduced expression of at least a 20%, 30%, 40%, 50%, 60%, 70%, 80%, 90%, 95% or 100% of at least one T-cell activator molecule in comparison to the expression of said T-cell activator molecule in a mature antigen presenting cell. The percentage of reduction of said T-cell activator molecule can be measured by techniques known in the art, e.g. by flow cytometry or RT-PCR.

The producer cells are grown in a conditioned media, and the sEVs or the exosomes are produced and released to said media. In the context of the present invention, the term "conditioned media" is understood as the supernatant of cell cultures. Since the population of sEVs or exosomes is released into the extracellular media when the intracellular multivesicular bodies fuse with the plasma membrane of the producer cell, the sEVs or exosome outer membrane would be similar as the one of the producing cell. Thus, in an embodiment, the population of sEVs or exosomes are positive for cellular markers, preferably cellular immature dendritic cell (iDC) markers. Further preferred, the population of sEVs or exosomes comprise one or more of the specific exosome markers selected from the groups consisting of ALIX, TSG101, CD9 or CD81, or any combination thereof. In another embodiment, the sEVs or exosomes are characterized by lacking the MHC-II, CD80, CD86 or GRP94 markers, or any combination thereof. In an embodiment, the sEVs or exosomes have an immature phenotype, so that they are low immunogenic.

In a preferred embodiment, the population according to the first aspect or any of its embodiments comprises a substantially pure population of immature dendritic cells (iDC)-derived sEVs or exosomes, for use in the treatment or prevention of obesity in a subject in need thereof, wherein the iDC-derived sEVs or exosomes, preferably each of the iDC-derived sEVs or exosomes, comprise at least one polynucleotide encoding an AMPK protein, preferably AMPKα, preferably AMPKα1, most preferably AMPKα1-DN mutant protein operably linked and under the control of a SF1 promoter, and wherein the DC-derived sEVs or iDC-derived exosomes are engineered to transiently express in their outer membrane at least one fusion protein comprising the RVG peptide fused to Lamp2b.

As discussed above, the results provide evidence that the population of sEVs or exosomes described herein is able to decrease or reduce the phosphorylation levels of pACCα and/or the activation levels of AMPK in SF1 expressing neurons located in the VMH. Additionally, the present invention shows the outstanding specificity of the treatment disclosed herein: when the phosphorylation levels of pACCα were assessed in other tissues, it was found that pACCα levels were not decreased in the neighbouring hypothalamic nuclei such as ARC, DMH and PVH (FIG. 11) nor in other brain areas (cortex, thalamus, cerebellum, FIG. 12A). This indicates that the activation levels of AMPK in these brain areas were not modified by the treatment. Further, to investigate the impact of the treatment in other tissues out of the brain and to elucidate how the systemic treatment may be affecting other biological processes such as testicular, adrenal and pituitary function, the circulating levels of testosterone and corticosterone (CORT) as well as the mRNA expression of key steroidogenic enzymes in the testis and adrenal gland of mice treated with control and SF1-AMPKα1-DN loaded sEVs were analysed. The data showed that treatment with SF1-AMPKα1-DN loaded sEVs did not induce any significant change in any of these parameters (FIGS. 12*d* and *e*). Similarly, no changes were found either in the circulating levels of luteinizing hormone (LH; FIG. 12*h*) or in the mRNA levels of the LH beta subunit (FIG. 12*i*), which pituitary production is known to be regulated by SF1. Altogether, these results suggest that the potential side effects on blunting AMPK signalling in other tissues, including those that express SF1 such as, pituitary, testis and adrenal gland, are probably negligible, confirming that the activation levels of AMPK in said tissues were not affected or modified by the treatment, indicating that the treatment is not only effective, but also safe and highly specific. Thus, the safe profile and high specificity of the treatment provided herein guarantee its therapeutic use in the treatment of obesity. The safe profile and high specificity is associated, as shown in the Examples below, to the systemic administration of the sEVs described herein, as this type of administration is less invasive than local (brain) administration, but since the treatment is highly specific, no off-target effects are found, as the reduced AMPK signalling is only present in the target tissues (SF1 expressing neurons located in the VMH region of the brain).

In view of this, in a preferred embodiment, the population of sEVs for use in the treatment of obesity according to the first aspect or any of its embodiments is capable, when administered systemically, of significantly decreasing the activation levels of AMPK, preferably AMPKα1, in SF1 expressing neurons located in the ventromedial nucleus of the hypothalamus (VMH) in comparison to the activation levels of AMPK, preferably AMPKα1, in untreated SF1 expressing cells, preferably untreated SF1 expressing neurons, without said decrease being statistically significant in other SF1 expressing cells and/or tissues, preferably non-neuronal tissues/organs, more preferably those selected from the list consisting of adrenal glands, testicles, or pituitary gland. Thus, as a result of AMPK inhibition, the exogenous AMPKα1-DN isoform lacks kinase activity and therefore the AMPK heterotrimer (alpha, beta, gamma; preferably alpha1 in this case) cannot be properly regulated and exert its phosphorylation effect on downstream targets. By "AMPK inhibition" is referred herein as a decrease in AMPK activation levels.

In an embodiment, the absence of a statistically significant decrease in other SF1 expressing cells and/or tissues, which indicates the specificity of the treatment, may be due to the absence of said SF1 expressing cells and/or tissues in the subject, such as the case of the absence of testicles in females, and/or may be due to that, despite of the presence of said cells/tissues, the treatment is not affecting them.

It should be noted that, to study the safety and efficacy of the treatment provided herein, in addition to directly measuring the activation levels of AMPK in SF1 expressing neurons located in the ventromedial nucleus of the hypothalamus (VMH), other surrogate markers that are indicative of the decrease of said activations levels can be further used. For example, the phosphorylation levels of acetyl-CoA carboxylase alpha (pACCα) can be used as indicator of the effectiveness or safety of the treatment. Thus, in an embodiment, the population of sEVs for use in the treatment of obesity via the systemic route according to the first aspect or any of its embodiments is capable, when administered systemically, of significantly decreasing the phosphorylation levels of pACCα in SF1 expressing neurons located in the ventromedial nucleus of the hypothalamus (VMH) in comparison to the phosphorylation levels of pACCα in untreated SF1 expressing cells, preferably in SF1 expressing neurons, without said decrease being statistically significant in other SF1 expressing cells and/or tissues, preferably those selected from the list consisting of adrenal glands, testicles, or pituitary gland.

By "statistically significant" or "significant" is referred herein as the determination by an analyst that the results in the data are not explainable by chance alone. Statistical hypothesis testing is the method by which the skilled person makes this determination. This test provides a p-value, which is the probability of observing results as extreme as those in the data, assuming the results are truly due to chance alone. A p-value of 0.1 or lower (preferably 0.05, 0.01, 0.001 or lower) is considered herein to be statistically significant. For example, the reduction in the pACCα levels or activation levels of AMPK protein in DF expressing neurons located in the VMH is a statistically significant reduction or decrease when a statistical test is performed to compare treated SF1 expressing neurons located in the VMH with untreated SF1 expressing cells or neurons, and wherein the resulting p-value of said statistical test is of 0.1 or lower, preferably 0.05, 0.01, 0.001 or lower.

By "decrease" or "increase" is referred herein as a reduction or rise, respectively, in at least a 10%, 20%, 30%, 40%, 50%, 60%, 70%, 80%, 90%, or 100% in comparison to a reference cell or value or reference tissue. Preferably, the increase is at least 2, 3, 4, 5, 6, 7, 8, 9, 10, 12, 14, 16, 18, 20-fold increase with respect to a reference cell or value or reference tissue. By "reference cell or tissue" is referred herein to a cell or tissue not treated with the sEVs of exosomes described herein. Preferably, said cell or tissue is a mammalian cell e.g., a human cell, preferably a neuron or a cell or tissue from the central nervous system, preferably from the VMH region. The reference cell may also be any SF1 expressing cell, preferably a SF1 expressing neuron located in the hypothalamus, preferably in the VMH region. The reference cell may also be a single cell or a population of cells derived from the same subject or from a population of subjects. The reference cell may also be a cell, preferably a SF1 expressing cell, from a subject not affected by obesity. By "reference value" is referred herein to the average known and correct measurement of a parameter, for instance the levels of pACCα or the activity levels of AMPK protein in untreated cells or in reference cells. Reference values are an average of repeated measurements from more accurate measuring equipment. A skilled artisan would know how to obtain said reference value.

Preferably, the SF1 expressing cell is a neuron located in the ventromedial nucleus of the hypothalamus (VMH). The levels of phosphorylation or enzymatic activity may be expressed or measured by an "absolute" quantification or by a "relative" or comparative quantification and they can be calculated by a skilled person using suitable techniques. Methods or techniques used to measure the phosphorylation levels of pACCα include, but are not limited to, Sodium Dodecyl Sulfate Polyacrylamide Gel Electrophoresis (SDS-PAGE), Western blotting, Flow Cytometry, Kinase activity assays, Enzyme-Linked Immunosorbent Assay (ELISA), and Antibody Array, Mass Spectrometry (MS). Methods or techniques used to measure the activity levels of AMPK protein include, but are not limited to, Optical, Magnetic Resonance, and Nuclear Imaging Methods (Fluorescence-based methods such as In situ zymography, Magnetic resonance-based methods), Mass spectrometry-based methods, Sampling-based methods (Microdialysis, Electroosmosis-based methods), and Measuring Enzyme Activity methods.

As explained above and as shown in FIG. 4, mice treated with the sEVs described herein displayed a marked long-term reduction on their body weight, with no changes in food intake. Of note, the effect of sEVs was sustained when the treatment was withdrawn, showing that treated mice did not exhibit any catch up in their body weight after treatment was ceased (washout), when compared to control mice treated with control sEVs. Overall, these data indicate that the body weight loss induced by the population of SF1-AMPKα1-DN loaded sEVs comprising RVG-Lamp2b fusion protein is not transient and treatment washout does not produce a rebound effect that lead the treated mice to reach the weight of untreated mice. This data supports the notion that the treatment disclosed herein further provides ameliorating or reduction of the rebound effect during and/or after treatment washout or cessation. By "ameliorating" is referred herein as the improvement in a subject's condition, or the activity of making an effort to correct, or at least make more acceptable, conditions that are difficult to endure related to patient's condition. Particularly, the condition is the obesity. By "rebound effect" is referred herein as the production negative symptoms when the effect of the treatment (population of sEVs or exosomes) has passed, or the patient is no longer responding to it. As a mode of example of a rebound effect, we refer to FIG. 3 in paper by Kawashima (2019, doi: 10.3389/fphys.2019.01483), where it is observed that treated mice were significantly heavier than the control mice after 40 days of the initial cycle of high-fat dieting. Thus, by "rebound effect" is meant herein an increase of at least 15%, 20%, 25%, 30%, 35%, 40%, 50%, 60%, or more of the basal body weight of the subject, understanding basal body weight as the weight of the subject without the treatment.

Preferably, the reduction or the amelioration of the rebound effect is measured at least 5, 10, 15, 20, 25, 30, 35, 40, 45, 50, 55, 60, 65, 70, 75, 80, 85, 90, or more than 90 days during or after treatment washout. Preferably, the reduction or the amelioration of the rebound effect is measured at least between 5-15, 5-20, 5-30, or 5-40 days after during or treatment washout.

Thus, in an embodiment, the population of sEVs or exosomes is capable, when administered systemically, of significantly decreasing or ameliorating the rebound effect, which is preferably measured as an increase of at least 15%-20% of the basal body weight of the subject without the treatment, during and/or after treatment washout or cessation. In an embodiment, the population of sEVs or exosomes is capable, when administered systemically, of significantly reverting or ameliorating obesity or its symptoms.

In some embodiments, the sEVs or exosomes are produced from autologous cells of the subject to be treated or were obtained from cells that were isolated from the subject to be treated. In other embodiments, the sEVs or exosomes are produced from allogeneic cells to the subject to be treated or were obtained from cells that were isolated from a donor other than the subject to be treated. In particular embodiments, the cell is a mammalian cell, e.g., a human cell. In particular embodiments, the cell is an immature dendritic cell.

sEVs Preparation and Storage and Compositions Thereof

The population described herein comprises an effective amount of oil-in-water emulsion of a substantially pure population of sEVs or exosomes as defined above, together with one or more pharmaceutically acceptable carriers. An "effective amount" is the amount sufficient to reduce, ameliorate, treat and/or prevent obesity or the rebound effect after obesity treatment. The effective amount will vary depending upon several factors including the age and weight of the subject to be treated, how advanced the disease state is, the general health of the patient, the severity of the symptoms, and whether the emulsion is being administered alone or in combination with other therapies.

The carrier should be biologically acceptable without eliciting an adverse reaction (e.g. immune response) when administered to the host. Suitable pharmaceutically acceptable carriers are well known in the art and vary with the desired form and mode of administration of the pharmaceutical formulation. For example, they may include diluents or excipients such as fillers, binders, wetting agents, disintegrators, surface-active agents, lubricants and the like. Typically, the carrier is a solid, a liquid or a vaporizable carrier, or a combination thereof. Each carrier should be "acceptable" in the sense of being compatible with the other ingredients in the formulation and not injurious to the subject.

The population may be part of a composition comprising emulsions containing sEVs or exosomes. Such emulsions may comprise oil-in-water emulsions. The emulsions may be made by means known in the art. They may be made from freshly prepared sEVs or exosomes, or lyophilised sEVs or exosomes or sEVs or exosomes stored in oil. Emulsions are heterogeneous systems composed of at least two immiscible liquids, for example water and oil, one of which is usually uniformly dispersed as fine droplets throughout the other liquid phase by a mechanical agitation process. The composition may further comprise at least one emulsifier. An emulsifier (also known as an "emulgent") is a substance that stabilizes an emulsion by increasing its kinetic stability.

The sEVs or exosomes may be conveniently stored as a suspension or dispersion in oil. For this purpose, freshly prepared sEVs or exosomes or lyophilised exosomes may be suspended or dispersed in oil. The oil may comprise any suitable oil, such as a plant oil. The sEVs or exosomes may be suspended or dispersed in for example olive oil, palm oil, soy oil or coconut oil. The sEVs or exosomes may be suspended or dispersed in the oil in any suitable proportion.

The sEVs or exosomes suspension or dispersion in oil may be stored, for example at room temperature, prior to use. The sEVs or exosomes suspension or dispersion in oil may be such that the exosome exhibits at least one biological activity of an sEVs or exosomes following a period of storage or after a period of storage. The biological activity may comprise a therapeutic activity, such as correcting, reducing, ameliorating, treating, preventing obesity or the rebound effect after obesity treatment. The biological activity may be derived from the presence of a dominant negative AMPKα1 protein (AMPKα1-DN), which in turn decreases AMPK activity and pACC phosphorylation. The biological activity may be derived from the reduced levels of phosphorylation of acetyl-CoA carboxylase alpha (pACCα). The sEVs or exosomes may exhibit at least 5%, 10%, 20%, 30%, 40%, 50%, 60%, 70%, 75%, 80%, 85%, 90%, 95%, or 100% of the biological activity as defined above following storage or after storage.

In an embodiment, the composition is a pharmaceutical composition. The pharmaceutical composition is preferably enriched with the population of sEVs exosomes having a size of between about 30 to 200 nm, preferably 30 to 150 nm in size. The sEVs or exosomes amount can be measured by protein amount, for example, by using a Bradford assay (BioRad) or a BCA protein assay kit (Pierce). Yet, the optimal dose will be selected according to the administration route, treatment regime and/or administration schedule, having regard to the existing toxicity and effectiveness data. In a preferred embodiment the substantially pure population of sEVs or exosomes comprised in the composition is in a dosage capable of providing a weight reducing or BAT increase effect in the absence of toxic effects.

In addition, said population or composition or pharmaceutical composition is formulated to be compatible with its intended route of administration. As shown in the Examples and as discussed above, the administration route can be systemic or local. Local administration routes include intracerebroventricular or, more preferably, specific stereotaxic administration in discrete hypothalamic nuclei. By "systemic administration routes" is referred herein the administration of the composition into the circulatory system, directly or indirectly. Systemic administrations are usually safer than local administrations, but they may not be well tolerated, or they can cause off-target effects. However, the present invention shows the safety of the treatment when administered systemically, and thus this is the preferred administration route for the treatment provided herein. Systemic administration routes comprise parenteral route such as intravascular, intravenous, intraarterial, subcutaneous, intramuscular, intraperitoneal, intraventricular, intraepidural, or others as well as oral, nasal, ophthalmic, or rectal. A preferred systemic route of administration is intravascular, which is herein understood as the administration within a vessel or vessels and typically includes intravenous or intraarterial administration.

Method for producing the population or the composition or pharmaceutical composition according to the present invention are known in the art, and they optionally comprise the step of specifically enriching for substantially pure populations of sEVs or exosomes. For this, generally any suitable method for purifying and/or enriching can be used, such as methods comprising magnetic particles, filtration, dialysis, ultracentrifugation, ExoQuick™ (Systems Biosciences, CA, USA), and/or chromatography.

As explained above, the principal object of the present invention is the provision of a safe and effective, tissue-specific population of sEVs for treatment or prevention of obesity. The use provided herein may be short or long term defined as a period of time exceeding three months. The use for treating or preventing obesity provided herein minimizes side effects and/or complications, especially those derived from suppression the activity of AMPK proteins in SF1 expressing tissues. Further, the use provided herein may simultaneously treat other diseases or obesity related diseases such as type II diabetes, cardiovascular disease, hypertension, or hypercholesterolemia.

A second aspect of the present invention refers to a population of sEVs as defined under the first aspect, wherein the sEVs comprise at least one polynucleotide encoding an AMPK protein, preferably AMPKα, preferably AMPKα1, most preferably AMPKα1-DN (dominant negative AMP-activated protein kinase alpha 1 mutant) protein operably linked and under the control of a steroidogenic factor 1 (SF1) promoter; and wherein the sEVs, are engineered to transiently express in their outer membrane at least one fusion protein comprising the neurotrophic rabies virus (RVG) peptide fused to lysosome-associated membrane protein 2b (Lamp2b). As the sEVs have been characterized above under the first aspect of the invention, all of the embodiments related to the sEVs also apply herein to the second aspect.

Preferably, the population of sEVs are exosomes, preferably a pure population of exosomes. In an embodiment, the population of sEVs or exosomes is a substantially pure population. In some embodiments, the population is substantially pure or enriched in sEVs or exosomes and comprises at least about 50%, 55%, 60%, 70%, 75%, 80%, 85%, 90%, 95%, 98%, or 100% of sEVs or exosomes. In an embodiment, the sEVs or exosomes are spherical or round shaped. Embodiments relating to the size have been defined above under the first aspect and apply herein.

The population of sEVs or exosomes provided herein comprise or are loaded with at least one polynucleotide comprising a gene encoding an AMPK protein, preferably AMPKα, preferably AMPKα1, most preferably AMPKα1-DN mutant protein, wherein said gene is operably linked and under the control of a SF1 promoter. Preferably, each of the sEVs of the population is loaded with at least one polynucleotide comprising a gene encoding an AMPK protein, preferably AMPKα, preferably AMPKα1, most preferably AMPKα1-DN mutant protein, wherein said gene is operably linked and under the control of a SF1 promoter.

In an embodiment, the AMPKα1-DN mutant protein encoded by the at least one polynucleotide comprised in the sEVs or exosomes comprises, consists, or consists essentially of an amino acid sequence with at least 80%, 85%, 90%, 91%, 92%, 93%, 94%, 95%, 96%, 97%, 97.5% 98%, 98.5%, 99%, 99.5%, or 100% sequence identity, over its full length, with SEQ ID NO: 1, 39 or 41.

In an embodiment, the AMPKα1-DN mutant protein encoded by the at least one polynucleotide comprised in the sEVs or exosomes comprises an amino acid sequence with at least 50%, 60%, 70%, 75%, 80%, 85%, 90%, 91%, 92%, 93%, 94%, 95%, 96%, 97%, 98%, 98.2%, 98.4%, 98.6%, 98.8%, 99%, 99.2%, 99.4%, 99.6%, 99.7%, 99.8%, 99.9% or 100% sequence identity with SEQ ID NO: 40 (wild-type rat AMPKα1 sequence), with the proviso that the amino acid residue in position number 168 in SEQ ID NO: 40, which corresponds with an Aspartic acid, is substituted by an amino acid residue that is not Aspartic acid, preferably substituted by Alanine (mutation D168A).

Please note that here and thorough the whole document, the amino acid residue positions are preferably numbered sequentially or consecutively starting from the N terminal end of the protein or polypeptide. It is also noted that the amino acid numbering, and therefore the number of the amino acid substitution that results in AMPKα1-DN mutant protein as defined herein, may change within different AMPKα1 proteins. For example, the substitution D168A in SEQ ID NO: 40 or 41 equals to substitution D169A in SEQ ID NO: 1 (AMPKα1-DN mutant protein amino acid sequence with Myc-Tag and G-linker), and substitution D156A in SEQ ID NO: 39 (AMPKα1-DN mutant protein amino acid sequence without Myc-Tag and G-linker). Thus, it is to be understood that, regardless of the numbering where said Aspartic acid is placed in the sequence of the AMPKα1 protein, and if it is changed for a different amino acid residue, one can arrive at the AMPKα1-DN mutant protein as defined herein. Preferably, the Aspartic acid to be mutated in the sequence of the AMPKα1 to generate the AMPKα1-DN mutant protein is the Aspartic acid of the conservative sequence "NAKIADFGLS". Preferably, said AMPKα1-DN mutant protein is capable of impairing or decreasing the activity of the cells' endogenous functional counterpart (AMPKα1 wild-type), resulting in a decrease of the pACC phosphorylation levels in a treated cell, preferably in the VMH area, but not in other SF-1 expressing tissues such as adrenal, pituitary and testis.

As explained above in the first aspect, the sEVs or exosomes provided herein further comprise or are loaded with, preferably mainly at their outer membrane, a fusion protein comprising or consisting of the neurotrophic rabies virus (RVG) peptide fused to lysosome-associated membrane protein 2b (Lamp2b), wherein said fusion protein comprises, consists or consists essentially of an amino acid sequence with at least 50%, 60%, 70%, 75%, 80%, 85%, 90%, 91%, 92%, 93%, 94%, 95%, 96%, 97%, 98%, or 100% sequence identity, over its full length, with SEQ ID NO 5. In this case, the domains comprised or consisting of the fusion protein are the RVG peptide and the Lamp2b protein. In an embodiment, the domains of a fusion protein may be linked by a linker peptide.

In an embodiment, the population of sEVs according to the second aspect or any of its embodiments are for use in therapy. In an embodiment, the population of sEVs according to the second aspects are for use in the treatment or prevention of obesity in a subject in need thereof, wherein preferably the obesity is diet-induced and/or genetic-induced obesity, preferably leptin receptor (LEPR) deficiency-induced obesity.

In an embodiment, the population of sEVs according to the second aspect or any of its embodiments are for use in the amelioration or reduction of the rebound effect during and/or after washout of the treatment of obesity. Description and embodiments of "ameliorating" and "rebound effect" are included above under the first aspect and apply herein.

In an embodiment, the population of sEVs is capable of, preferably when administered systemically, significantly decreasing the activation levels of AMP-activated protein kinase (AMPK) in SF1 expressing neurons located in the ventromedial nucleus of the hypothalamus (VMH) in comparison to the activation levels of AMPK in untreated SF1 expressing cells, without said decrease being significantly reduced in other SF1 expressing tissues selected from the list consisting of adrenal glands, testicles, or pituitary gland, wherein said population of sEVs comprises at least one polynucleotide encoding a dominant negative AMP-activated protein kinase alpha 1 (AMPKα1-DN) mutant protein, wherein the amino acid sequence of the AMPKα1-DN mutant protein is characterized by having at least 95%, 96%, 97%, 97.5%, 98%, 98.5%, 99%, 99.5% or 100% sequence identity with SEQ ID NO: 1, 39, or 41, and wherein said AMPKα1-DN mutant protein is operably linked and under the control of a steroidogenic factor 1 (SF1) promoter, wherein preferably said SF1 promoter has at least 90%, 93%, 95%, 96%, 97%, 98%, 99%, or 100% sequence identity with SEQ ID NO: 3, wherein the sEVs are engineered to transiently express in their outer membrane at least one fusion protein comprising the neurotrophic rabies virus (RVG) peptide fused to lysosome-associated membrane protein 2b, and wherein said population is for use in the in the treatment or prevention of obesity, preferably via the systemic route of administration, in a subject in need thereof.

In an embodiment, the population of sEVs is capable of, preferably when administered systemically, significantly decreasing the activation levels of AMP-activated protein kinase (AMPK) in SF1 expressing neurons located in the ventromedial nucleus of the hypothalamus (VMH) in comparison to the activation levels of AMPK in untreated SF1 expressing cells, without said decrease being significantly reduced in other SF1 expressing tissues selected from the list consisting of adrenal glands, testicles, or pituitary gland, wherein said population of sEVs comprises at least one polynucleotide encoding a dominant negative AMP-activated protein kinase alpha 1 (AMPKα1-DN) mutant protein, wherein the amino acid sequence of the AMPKα1-DN mutant protein is characterized by having at least 95%, 96%, 97%, 97.5%, 98%, 98.5%, 99%, 99.5% or 100% sequence identity with SEQ ID NO: 40 (wild-type rat AMPKα1 sequence), with the proviso that the amino acid residue in position number 168 in SEQ ID NO: 40, which corresponds with an Aspartic acid, is substituted by an amino acid residue that is not Aspartic acid, preferably substituted by Alanine (mutation D168A), and wherein said AMPKα1-DN mutant protein is operably linked and under the control of a steroidogenic factor 1 (SF1) promoter, wherein preferably said SF1 promoter has at least 90%, 93%, 95%, 96%, 97%, 98%, 99%, or 100% sequence identity with SEQ ID NO: 3, wherein the sEVs are engineered to transiently express in their outer membrane at least one fusion protein comprising the neurotrophic rabies virus (RVG) peptide fused to lysosome-associated membrane protein 2b, and wherein said population is for use in the in the treatment or prevention of obesity, preferably via the systemic route of administration, in a subject in need thereof.

SEQUENCE LISTING
SEQ ID NO 1: AMPKα1-DN mutant protein amino acid sequence.
Note: (Underlined: Myc-Tag)
(Gray highlighted: G-Linker)
(Bold and underlined: mutations D168->A wherein the amino acid numbering or position of the mutation is with respect to rat AMPKα1 protein, preferably of SEQ ID NO: 40)

MEQKLISEEDLGGGEKQKHDGRVKIGHYILGDTLGVGTFGKVKVGKHELTGHKVAVKILNRQ

KIRSLDVVGKIRREIQNLKLFRHPHIIKLYQVISTPSDIFMVMEYVSGGELFDYICKNGRLDEKE

SRRLFQQILSGVDYCHRHMVVHRDLKPENVLLDAHMNAKIAAFGLSNMMSDGEFLRTSCG

SPNYAAPEVISGRLYAGPEVDIWSSGVILYALLCGTLPFDDDHVPTLFKKICDGIFYTPQYLN

-continued

PSVISLLKHMLQVDPMKRATIKDIREHEWFKQDLPKYLFPEDPSYSSTMIDDEALKEVCEKFE

CSEEEVLSCLYNRNHQDPLAVAYHLIIDNRRIMNEAKDFYLATSPPDSFLDDHHLTRPHPER

VPFLVAETPRARHTLDELNPQKSKHQGVRKAKWHLGIRSQSRPNDIMAEVCRAIKQLDYEW

KVVNPYYLRVRRKNPVTSTFSKMSLQLYQVDSRTYLLDFRSIDDEITEAKSGTATPQRSGSI

SNYRSCQRSDSDAEAQGKPSEVSLTSSVTSLDSSPVDVAPRPGSHTIEFFEMCANLIKILAQ

SEQ ID NO 2: Polynucleotide sequence encoding for the dominant negative AMP-activated protein kinase alpha 1 (AMPKα1) mutant protein.

Note: Underlined (Myc-tag sequence)

ATGGAGCAGAAGCTTATCTCCGAGGAGGACCTCGGTGGCGGCGAGAAGCAGAAGCAC

GACGGGCGGGTGAAGATCGGCCACTACATCCTGGGGGACACGCTGGGCGTCGGCACC

TTCGGGAAAGTGAAGGTGGGCAAGCACGAGTTGACTGGACATAAAGTTGCTGTGAAGA

TACTCAACCGGCAGAAGATTCGAAGCCTGGACGTGGTCGGGAAAATCCGCAGAGAGAT

CCAGAACCTGAAGCTTTTCAGGCACCCTCATATAATCAAACTGTACCAGGTCATCAGTAC

ACCGTCTGATATTTTCATGGTCATGGAATATGTCTCAGGAGGAGAGCTATTTGATTATAT

CTGTAAAAATGGAAGGTTGGACGAAAAGGAGAGTCGACGTCTGTTCCAGCAGATCCTTT

CTGGTGTGGACTATTGTCACAGGCATATGGTGGTCCACAGAGATTTGAAACCTGAAAAC

GTCCTGCTTGATGCACACATGAATGCAAAGATAGCCGCCTTCGGTCTTTCAAACATGAT

GTCAGATGGTGAATTTTTAAGAACGAGCTGTGGCTCGCCCAATTATGCTGCACCAGAAG

TAATTTCAGGAAGATTGTACGCAGGCCCTGAAGTAGACATCTGGAGCAGCGGGGTCATT

CTCTATGCTTTGCTGTGTGGAACTCTCCCTTTTGATGATGACCACGTGCCAACTCTTTTT

AAGAAGATATGTGACGGGATATTTTATACCCCTCAGTATTTGAATCCCTCTGTAATAAGC

CTTTTGAAGCATATGCTGCAGGTAGATCCTATGAAGAGGGCCACAATAAAAGATATCAG

GGAACATGAATGGTTTAAGCAGGACCTTCCAAAATATCTCTTTCCTGAAGACCCGTCTTA

TAGTTCAACCATGATTGATGATGAAGCCTTAAAAGAAGTGTGTGAGAAGTTCGAGTGCT

CAGAGGAGGAGGTCCTCAGCTGCCTGTACAACAGAAACCACCAGGACCCACTGGCAGT

TGCCTACCACCTCATAATAGACAACAGGAGAATAATGAACGAAGCCAAAGATTTCTACTT

GGCAACAAGCCCACCCGATTCTTTCCTCGATGATCACCATTTAACTCGGCCTCACCCTG

AGAGAGTACCATTCTTGGTTGCCGAAACACCAAGGGCCCGACACACCCTAGATGAATTA

AACCCACAGAAATCCAAACACCAAGGCGTACGGAAGGCAAAGTGGCATTTGGGGATTC

GAAGTCAAAGCCGACCCAATGACATCATGGCAGAAGTGTGTAGAGCAATCAAGCAGTTG

GACTATGAATGGAAGGTTGTAAACCCCTATTATTTGCGTGTGCGAAGGAAGAACCCTGT

GACAAGCACATTTTCCAAAATGAGTCTACAGCTATACCAAGTGGATAGTAGGACTTACTT

ATTGGATTTCCGAAGTATTGATGATGAGATTACAGAAGCCAAATCAGGGACTGCTACTC

CACAGAGATCGGGATCCATCAGCAACTATCGATCTTGCCAAAGGAGCGACTCCGACGC

CGAGGCTCAAGGAAAGCCCTCAGAAGTCTCTCTTACCTCATCCGTGACCTCCCTCGACT

CCTCTCCTGTTGACGTAGCTCCAAGACCAGGAAGTCACACGATAGAATTTTTTGAAATGT

GTGCAAATCTAATTAAAATTCTTGCACAGTAA

SEQ ID NO 3: Steroidogenic factor 1 (SF1) polynucleotide sequence.

AAAACAAAACAAAACAAAACAAAACAAAACAAAACAAACAAACAAACAAACAAACAAAAA

CCCTTCTTTCCTACCTGGTCCTAGTACCCACATAGTCCTACCTGAAGTCCCTGAAGCCA

CACCCTTAGCCCAGCAGTCTTGGCACAACCTCAGTTTCCCCAGCTACCAATGGACCATA

TCTGCAGCTCCCAGAGAAGCCACCAAAAAGGCCACACAAACCCCACCTGATGGGTTCC

ACCATGCCATTTCTCCACACTAGCCATTCTGACTCCTCACTCAGATCTGGGACAAGCTG

-continued

GACCACGCAGCCCAGGCAAGGACCCAGGGAGGAAGCCATTCAAGGGGAGAAACTCCC

AGCCTGGTAAGGGAGCAGGCCATAAATCAGGTCCCACTCCCACCCAGTCGCTAACAAG

CCGCTGCCTATCTGCCTACATGGGGTCCCTGCCTCAGGCTCCCTCATCAGCCTGGACA

GCCAGCTGGCCAAGGTCTCTCCAGTGCCTTGGCCTCTGCCCCCACCCAGGGCCCCCAT

AAAGATAGGGATATTTTTTTTTCTTTTAGAAGAGTGAAAAAAGATATAGACCCAAATGAAG

AGAAACACCAACAAAGGAGGAGAAAGGCCTGCAGAGTCACGTGGGGGCAGAGACCAA

TTGGGCCTCCGGTGGCCCCCCCACCCACGAGGGGAGGAGGAAAGGACGATCGGACAG

GGCCAGTTTCCAGTCCGCCGCTGCCCGCCCGCTGCTGGGT

SEQ ID NO 4: Polynucleotide sequence encoding an AMPKα1-DN mutant protein operably linked and under the control of the SF1 promoter.

AAAACAAAACAAAACAAAACAAAACAAAACAAAACAAACAAACAAACAAACAAACAAAAA

CCCTTCTTTCCTACCTGGTCCTAGTACCCACATAGTCCTACCTGAAGTCCCTGAAGCCA

CACCCTTAGCCCAGCAGTCTTGGCACAACCTCAGTTTCCCCAGCTACCAATGGACCATA

TCTGCAGCTCCCAGAGAAGCCACCAAAAAGGCCACACAAACCCCACCTGATGGGTTCC

ACCATGCCATTTCTCCACACTAGCCATTCTGACTCCTCACTCAGATCTGGGACAAGCTG

GACCACGCAGCCCAGGCAAGGACCCAGGGAGGAAGCCATTCAAGGGGAGAAACTCCC

AGCCTGGTAAGGGAGCAGGCCATAAATCAGGTCCCACTCCCACCCAGTCGCTAACAAG

CCGCTGCCTATCTGCCTACATGGGGTCCCTGCCTCAGGCTCCCTCATCAGCCTGGACA

GCCAGCTGGCCAAGGTCTCTCCAGTGCCTTGGCCTCTGCCCCCACCCAGGGCCCCCAT

AAAGATAGGGATATTTTTTTTTCTTTTAGAAGAGTGAAAAAAGATATAGACCCAAATGAAG

AGAAACACCAACAAAGGAGGAGAAAGGCCTGCAGAGTCACGTGGGGGCAGAGACCAA

TTGGGCCTCCGGTGGCCCCCCCACCCACGAGGGGAGGAGGAAAGGACGATCGGACAG

GGCCAGTTTCCAGTCCGCCGCTGCCCGCCCGCTGCTGGGTACCGTTTAAACTCGAGGT

CGACGGTATCGATAAGCTTGATATCGAATTCGCCATGGAGCAGAAGCTTATCTCCGAGG

AGGACCTCGGTGGCGGCGAGAAGCAGAAGCACGACGGGGGGTGAAGATCGGCCACT

ACATCCTGGGGGACACGCTGGGCGTCGGCACCTTCGGGAAAGTGAAGGTGGGCAAGC

ACGAGTTGACTGGACATAAAGTTGCTGTGAAGATACTCAACCGGCAGAAGATTCGAAGC

CTGGACGTGGTCGGGAAAATCCGCAGAGAGATCCAGAACCTGAAGCTTTTCAGGCACC

CTCATATAATCAAACTGTACCAGGTCATCAGTACACCGTCTGATATTTTCATGGTCATGG

AATATGTCTCAGGAGGAGAGCTATTTGATTATATCTGTAAAAATGGAAGGTTGGACGAAA

AGGAGAGTCGACGTCTGTTCCAGCAGATCCTTTCTGGTGTGGACTATTGTCACAGGCAT

ATGGTGGTCCACAGAGATTTGAAACCTGAAAACGTCCTGCTTGATGCACACATGAATGC

AAAGATAGCCGCCTTCGGTCTTTCAAACATGATGTCAGATGGTGAATTTTTAAGAACGAG

CTGTGGCTCGCCCAATTATGCTGCACCAGAAGTAATTTCAGGAAGATTGTACGCAGGCC

CTGAAGTAGACATCTGGAGCAGCGGGGTCATTCTCTATGCTTTGCTGTGTGGAACTCTC

CCTTTTGATGATGACCACGTGCCAACTCTTTTTAAGAAGATATGTGACGGGATATTTTAT

ACCCCTCAGTATTTGAATCCCTCTGTAATAAGCCTTTTGAAGCATATGCTGCAGGTAGAT

CCTATGAAGAGGGCCACAATAAAAGATATCAGGGAACATGAATGGTTTAAGCAGGACCT

TCCAAAATATCTCTTTCCTGAAGACCCGTCTTATAGTTCAACCATGATTGATGATGAAGC

CTTAAAAGAAGTGTGTGAGAAGTTCGAGTGCTCAGAGGAGGAGGTCCTCAGCTGCCTG

TACAACAGAAACCACCAGGACCCACTGGCAGTTGCCTACCACCTCATAATAGACAACAG

GAGAATAATGAACGAAGCCAAAGATTTCTACTTGGCAACAAGCCCACCCGATTCTTTCCT

-continued

CGATGATCACCATTTAACTCGGCCTCACCCTGAGAGAGTACCATTCTTGGTTGCCGAAA

CACCAAGGGCCCGACACACCCTAGATGAATTAAACCCACAGAAATCCAAACACCAAGG

CGTACGGAAGGCAAAGTGGCATTTGGGGATTCGAAGTCAAAGCCGACCCAATGACATC

ATGGCAGAAGTGTGTAGAGCAATCAAGCAGTTGGACTATGAATGGAAGGTTGTAAACCC

CTATTATTTGCGTGTGCGAAGGAAGAACCCTGTGACAAGCACATTTTCCAAAATGAGTCT

ACAGCTATACCAAGTGGATAGTAGGACTTACTTATTGGATTTCCGAAGTATTGATGATGA

GATTACAGAAGCCAAATCAGGGACTGCTACTCCACAGAGATCGGGATCCATCAGCAACT

ATCGATCTTGCCAAAGGAGCGACTCCGACGCCGAGGCTCAAGGAAAGCCCTCAGAAGT

CTCTCTTACCTCATCCGTGACCTCCCTCGACTCCTCTCCTGTTGACGTAGCTCCAAGAC

CAGGAAGTCACACGATAGAATTTTTTGAAATGTGTGCAAATCTAATTAAAATTCTTGCACA

GTAA

SEQ ID NO 5: Fusion protein: Neurotrophic rabies virus (RVG) peptide fused to lysosome-associated membrane protein 2b (Lamp2b).
Note: (Not underlined: Lamp2b sequence)
(Underlined: RVG sequence)

MCLSPVKGAKLILIFLFLGAVQSNALIVNLTDSKGTCLYARYTIWMPENPRPGTPCDIFTNSRGKRASNGS

GGAEWEMNFTITYETTNQTNKTITIAVPDKATHDGSSCGDDRNSAKIMIQFGFAVSWAVNFTKEASHYSI

HDIVLSYNTSDSTVFPGAVAKGVHTVKNPENFKVPLDVIFKCNSVLTYNLTPVVQKYWGIHLQAFVQNGT

VSKNEQVCEEDQTPTTVAPIIHTTAPSTTTTLTPTSTPTPTPTPTPTVGNYSIRNGNTTCLLATMGLQLNITE

EKVPFIFNINPATTNFTGSCQPQSAQLRLNNSQIKYLDFIFAVKNEKRFYLKEVNVYMYLANGSAFNISNKN

LSFWDAPLGSSYMCNKEQVLSVSRAFQINTFNLKVQPFNVTKGQYSTAQECSLDDDTILIPIIVGAGLSGLII

VIVIAYLIGRRKTYAGYQTL

SEQ ID NO 38: Nucleotide sequence of the fusion protein made of the Neurotrophic rabies virus (RVG) peptide fused to lysosome-associated membrane protein 2b (Lamp2b). Note: (Not underlined: Lamp2b sequence)
(Underlined: RVG sequence)

GCTAGCGGTCGCCACCATGTGCCTCTCTCCGGTTAAAGGCGCAAAGCTCATCCTGATCTTTCT

GTTCCTAGGAGCCGTTCAGTCCAATGCATTGATAGTTAATTTGACAGATTCAAAGGGTACTTG

CCTTTATGCTCGATACACCATTTGGATGCCCGAGAATCCGAGACCAGGGACACCTTGTGACAT

TTTTACCAATAGCAGAGGGAAGAGAGCATCCAACGGGTCCGGAGGTGCAGAATGGGAGATGA

ATTTCACAATAACATATGAAACTACAAACCAAACCAATAAAACTATAACCATTGCAGTACCT

GACAAGGCGACACACGATGGAAGCAGTTGTGGGGATGACCGGAATAGTGCCAAAATAATGAT

ACAATTTGGATTCGCTGTCTCTTGGGCTGTGAATTTTACCAAGGAAGCATCTCATTATTCAAT

TCATGACATCGTGCTTTCCTACAACACTAGTGATAGCACAGTATTTCCTGGTGCTGTAGCTAA

AGGAGTTCATACTGTTAAAAATCCTGAGAATTTCAAAGTTCCATTGGATGTCATCTTTAAGT

GCAATAGTGTTTTAACTTACAACCTGACTCCTGTCGTTCAGAAATATTGGGGTATTCACCTGC

AAGCTTTTGTCCAAAATGGTACAGTGAGTAAAAATGAACAAGTGTGTGAAGAAGACCAAACT

CCCACCACTGTGGCACCCATCATTCACACCACTGCCCCGTCGACTACAACTACACTCACTCCAA

CTTCAACACCCACTCCAACTCCAACTCCAACTCCAACCGTTGGAAACTACAGCATTAGAAATG

GCAATACTACCTGTCTGCTGGCTACCATGGGGCTGCAGCTGAACATCACTGAGGAGAAGGTGC

CTTTCATTTTTAACATCAACCCTGCCACAACCAACTTCACCGGCAGCTGTCAACCTCAAAGTG

CTCAACTTAGGCTGAACAACAGCCAAATTAAGTATCTTGACTTTATCTTTGCTGTGAAAAATG

AAAAACGGTTCTATCTGAAGGAAGTGAATGTCTACATGTATTTGGCTAATGGCTCAGCTTTC

AACATTTCCAACAAGAACCTTAGCTTCTGGGATGCCCCTCTGGGAAGTTCTTATATGTGCAAC

AAAGAGCAGGTGCTTTCTGTGTCTAGAGCGTTTCAGATCAACACCTTTAACCTAAAGGTGCAA

CCTTTTAATGTGACAAAAGGACAGTATTCTACAGCCCAGGAGTGTTCGCTGGATGATGACACC

-continued

ATTCTAATACCAATTATAGTTGGTGCTGGTCTTTCAGGCTTGATTATCGTTATAGTGATTGCT

TACCTAATTGGCAGAAGAAAGACCTATGCTGGATATCAGACTCTGTAACACTAAGGATCC

SEQ ID NO 39: AMPKα1-DN mutant protein amino acid sequence (without the Myc-Tag peptide and the G-linker) Bold and underlined: mutations D168->A wherein the amino acid numbering or position of the mutation is with respect to rat AMPKα1 protein, preferably of SEQ ID NO: 40)

Met Glu Lys Gln Lys His Asp Gly Arg Val Lys Ile Gly His Tyr Ile
1 5 10 15
Leu Gly Asp Thr Leu Gly Val Gly Thr Phe Gly Lys Val Lys Val Gly
20 25 30
Lys His Glu Leu Thr Gly His Lys Val Ala Val Lys Ile Leu Asn Arg
35 40 45
Gln Lys Ile Arg Ser Leu Asp Val Val Gly Lys Ile Arg Arg Glu Ile
50 55 60
Gln Asn Leu Lys Leu Phe Arg His Pro His Ile Ile Lys Leu Tyr Gln
65 70 75 80
Val Ile Ser Thr Pro Ser Asp Ile Phe Met Val Met Glu Tyr Val Ser
85 90 95
Gly Gly Glu Leu Phe Asp Tyr Ile Cys Lys Asn Gly Arg Leu Asp Glu
100 105 110
Lys Glu Ser Arg Arg Leu Phe Gln Gln Ile Leu Ser Gly Val Asp Tyr
115 120 125
Cys His Arg His Met Val Val His Arg Asp Leu Lys Pro Glu Asn Val
130 135 140
Leu Leu Asp Ala His Met Asn Ala Lys Ile Ala Ala Phe Gly Leu Ser
145 150 155 160
Asn Met Met Ser Asp Gly Glu Phe Leu Arg Thr Ser Cys Gly Ser Pro
165 170 175
Asn Tyr Ala Ala Pro Glu Val Ile Ser Gly Arg Leu Tyr Ala Gly Pro
180 185 190
Glu Val Asp Ile Trp Ser Ser Gly Val Ile Leu Tyr Ala Leu Leu Cys
195 200 205
Gly Thr Leu Pro Phe Asp Asp Asp His Val Pro Thr Leu Phe Lys Lys
210 215 220
Ile Cys Asp Gly Ile Phe Tyr Thr Pro Gln Tyr Leu Asn Pro Ser Val
225 230 235 240
Ile Ser Leu Leu Lys His Met Leu Gln Val Asp Pro Met Lys Arg Ala
245 250 255
Thr Ile Lys Asp Ile Arg Glu His Glu Trp Phe Lys Gln Asp Leu Pro
260 265 270
Lys Tyr Leu Phe Pro Glu Asp Pro Ser Tyr Ser Ser Thr Met Ile Asp
275 280 285
Asp Glu Ala Leu Lys Glu Val Cys Glu Lys Phe Glu Cys Ser Glu Glu
290 295 300
Glu Val Leu Ser Cys Leu Tyr Asn Arg Asn His Gln Asp Pro Leu Ala
305 310 315 320
Val Ala Tyr His Leu Ile Ile Asp Asn Arg Arg Ile Met Asn Glu Ala
325 330 335
Lys Asp Phe Tyr Leu Ala Thr Ser Pro Pro Asp Ser Phe Leu Asp Asp
340 345 350
His His Leu Thr Arg Pro His Pro Glu Arg Val Pro Phe Leu Val Ala
355 360 365
Glu Thr Pro Arg Ala Arg His Thr Leu Asp Glu Leu Asn Pro Gln Lys
370 375 380
Ser Lys His Gln Gly Val Arg Lys Ala Lys Trp His Leu Gly Ile Arg
385 390 395 400
Ser Gln Ser Arg Pro Asn Asp Ile Met Ala Glu Val Cys Arg Ala Ile
405 410 415
Lys Gln Leu Asp Tyr Glu Trp Lys Val Val Asn Pro Tyr Tyr Leu Arg
420 425 430
Val Arg Arg Lys Asn Pro Val Thr Ser Thr Phe Ser Lys Met Ser Leu
435 440 445
Gln Leu Tyr Gln Val Asp Ser Arg Thr Tyr Leu Leu Asp Phe Arg Ser
450 455 460
Ile Asp Asp Glu Ile Thr Glu Ala Lys Ser Gly Thr Ala Thr Pro Gln
465 470 475 480
Arg Ser Gly Ser Ile Ser Asn Tyr Arg Ser Cys Gln Arg Ser Asp Ser
485 490 495
Asp Ala Glu Ala Gln Gly Lys Pro Ser Glu Val Ser Leu Thr Ser Ser
500 505 510

-continued

Val Thr Ser Leu Asp Ser Ser Pro Val Asp Val Ala Pro Arg Pro Gly
515 520 525
Ser His Thr Ile Glu Phe Phe Glu Met Cys Ala Asn Leu Ile Lys Ile
530 535 540
Leu Ala Gln
545

SEQ ID NO: 40: Wild-type 5'-AMP-activated protein kinase catalytic subunit alpha-1 [Rattus norvegicus]. NCBI Reference Sequence: NP_062015.2

Met Arg Arg Leu Ser Ser Trp Arg Lys Met Ala Thr Ala Glu 15 Gln
1 5 10 Lys
Lys His Asp Gly Arg Val Lys Ile Gly His Tyr Ile Leu Gly Asp Thr
20 25 30
Leu Gly Val Gly Thr Phe Gly Lys Val Lys Val Gly Lys His Glu Leu
35 40 45
Thr Gly His Lys Val Ala Val Lys Ile Leu Asn Arg Gln Lys Ile Arg
50 55 60
Ser Leu Asp Val Val Gly Lys Ile Arg Arg Glu Ile Gln Asn Leu Lys
65 70 75 80
Leu Phe Arg His Pro His Ile Ile Lys Leu Tyr Gln Val Ile Ser Thr
85 90 95
Pro Ser Asp Ile Phe Met Val Met Glu Tyr Val Ser Gly Gly Glu Leu
100 105 110
Phe Asp Tyr Ile Cys Lys Asn Gly Arg Leu Asp Glu Lys Glu Ser Arg
115 120 125
Arg Leu Phe Gln Gln Ile Leu Ser Gly Val Asp Tyr Cys His Arg His
130 135 140
Met Val Val His Arg Asp Leu Lys Pro Glu Asn Val Leu Leu Asp Ala
145 150 155 160
His Met Asn Ala 165 Ile Ala Asp Phe Gly Leu Ser Asn Met Met Ser
Lys 170 175
Asp Gly Glu Phe Leu Arg Thr Ser Cys Gly Ser Pro Asn Tyr Ala Ala
180 185 190
Pro Glu Val Ile Ser Gly Arg Leu Tyr Ala Gly Pro Glu Val Asp Ile
195 200 205
Trp Ser Ser Gly Val Ile Leu Tyr Ala Leu Leu Cys Gly Thr Leu Pro
210 215 220
Phe Asp Asp Asp His Val Pro Thr Leu Phe Lys Lys Ile Cys Asp Gly
225 230 235 240
Ile Phe Tyr Thr Pro Gln Tyr Leu Asn Pro Ser Val Ile Ser Leu Leu
245 250 255
Lys His Met Leu Gln Val Asp Pro 265 Lys Arg Ala Thr 270 Lys Asp
260 Met Ile
Ile Arg Glu His Glu Trp Phe Lys Gln Asp Leu Pro Lys Tyr Leu Phe
275 280 285
Pro Glu Asp Pro Ser Tyr Ser Ser Thr Met Ile Asp Asp Glu Ala Leu
290 295 300
Lys Glu Val Cys Glu Lys Phe Glu Cys Ser Glu Glu Glu Val Leu Ser
305 310 315 320
Cys Leu Tyr Asn Arg Asn His Gln Asp Pro Leu Ala Val Ala Tyr His
325 330 335
Leu Ile Ile Asp Asn Arg Arg Ile Met Asn Glu Ala Lys Asp Phe Tyr
340 345 350
Leu Ala Thr Ser Pro Pro Asp Ser Phe Leu Asp Asp His His Leu Thr
355 360 365
Arg Pro His Pro Glu Arg Val Pro Phe Leu Val Ala Glu Thr Pro Arg
370 375 380
Ala Arg His Thr Leu Asp Glu Leu Asn Pro Gln Lys Ser Lys His Gln
385 390 395 400
Gly Val Arg Lys Ala Lys Trp His Leu Gly Ile Arg Ser Gln Ser Arg
405 410 415
Pro Asn Asp Ile Met Ala Glu Val Cys Arg Ala Ile Lys Gln Leu Asp
420 425 430
Tyr Glu Trp Lys Val Val Asn Pro Tyr Tyr Leu Arg Val Arg Arg Lys
435 440 445
Asn Pro Val Thr Ser Thr Phe Ser Lys Met Ser Leu Gln Leu Tyr Gln
450 455 460
Val Asp Ser Arg Thr Tyr Leu Leu Asp Phe Arg Ser Ile Asp Asp Glu
465 470 475 480
Ile Thr Glu Ala Lys Ser Gly Thr Ala Thr Pro Gln Arg Ser Gly Ser
485 490 495
Ile Ser Asn Tyr Arg Ser Cys Gln Arg Ser Asp Ser Asp Ala Glu Ala
500 505 510
Gln Gly Lys Pro Ser Glu Val Ser Leu Thr Ser Ser Val Thr Ser Leu
515 520 525
Asp Ser Ser Pro Val Asp Val Ala Pro Arg Pro Gly Ser His Thr Ile
530 535 540
Glu Phe Phe Glu Met Cys Ala Asn Leu Ile Lys Ile Leu Ala Gln
545 550 555

-continued

SEQ ID NO: 41: Wild-type 5'-AMP-activated protein kinase catalytic subunit alpha-1 [Rattus norvegicus] with D168A mutation with respect to SEQ ID NO: 40.

```
Met  Arg  Arg  Leu  Ser  Ser  Trp  Arg  Lys  Met  Ala  Thr  Ala  Glu  Lys  Gln
1                   5                        10                       15
Lys  His  Asp  Gly  Arg  Val  Lys  Ile  Gly  His  Tyr  Ile  Leu  Gly  Asp  Thr
               20                       25                       30
Leu  Gly  Val  Gly  Thr  Phe  Gly  Lys  Val  Lys  Val  Gly  Lys  His  Glu  Leu
          35                       40                       45
Thr  Gly  His  Lys  Val  Ala  Val  Lys  Ile  Leu  Asn  Arg  Gln  Lys  Ile  Arg
     50                       55                       60
Ser  Leu  Asp  Val  Val  Gly  Lys  Ile  Arg  Arg  Glu  Ile  Gln  Asn  Leu  Lys
65                       70                       75                       80
Leu  Phe  Arg  His  Pro  His  Ile  Ile  Lys  Leu  Tyr  Gln  Val  Ile  Ser  Thr
                    85                       90                       95
Pro  Ser  Asp  Ile  Phe  Met  Val  Met  Glu  Tyr  Val  Ser  Gly  Gly  Glu  Leu
               100                      105                      110
Phe  Asp  Tyr  Ile  Cys  Lys  Asn  Gly  Arg  Leu  Asp  Glu  Lys  Glu  Ser  Arg
          115                      120                      125
Arg  Leu  Phe  Gln  Gln  Ile  135  Ser  Gly  Val  Asp  140  Cys  His  Arg  His
     130                      Leu                      Tyr
Met  Val  Val  His  Arg  Asp  Leu  Lys  Pro  Glu  Asn  Val  Leu  Leu  Asp  Ala
145                      150                      155                      160
His  Met  Asn  Ala  Lys  Ile  Ala  Ala  Phe  Gly  Leu  Ser  Asn  Met  175  Ser
                    165                      170                      Met
Asp  Gly  Glu  Phe  Leu  Arg  Thr  Ser  Cys  Gly  Ser  Pro  Asn  Tyr  Ala  Ala
               180                      185                      190
Pro  Glu  Val  Ile  Ser  Gly  Arg  Leu  Tyr  Ala  Gly  Pro  Glu  Val  Asp  Ile
          195                      200                      205
Trp  Ser  Ser  Gly  Val  Ile  Leu  Tyr  Ala  Leu  Leu  Cys  Gly  Thr  Leu  Pro
     210                      215                      220
Phe  Asp  Asp  Asp  His  Val  Pro  Thr  Leu  Phe  Lys  Lys  Ile  Cys  Asp  Gly
225                      230                      235                      240
Ile  Phe  Tyr  Thr  Pro  Gln  Tyr  Leu  Asn  Pro  Ser  Val  Ile  Ser  Leu  Leu
                    245                      250                      255
Lys  His  Met  Leu  Gln  Val  Asp  Pro  Met  Lys  Arg  Ala  Thr  Ile  Lys  Asp
               260                      265                      270
Ile  Arg  Glu  His  Glu  Trp  Phe  Lys  Gln  Asp  Leu  Pro  Lys  Tyr  Leu  Phe
          275                      280                      285
Pro  Glu  Asp  Pro  Ser  Tyr  Ser  Ser  Thr  Met  Ile  Asp  Asp  Glu  Ala  Leu
     290                      295                      300
Lys  Glu  Val  Cys  Glu  Lys  Phe  Glu  Cys  Ser  Glu  Glu  Glu  Val  Leu  Ser
305                      310                      315                      320
Cys  Leu  Tyr  Asn  Arg  Asn  His  Gln  Asp  Pro  Leu  Ala  Val  Ala  Tyr  His
                    325                      330                      335
Leu  Ile  Ile  Asp  Asn  Arg  Arg  Ile  Met  Asn  Glu  Ala  Lys  Asp  Phe  Tyr
               340                      345                      350
Leu  Ala  Thr  Ser  Pro  Pro  Asp  Ser  Phe  Leu  Asp  Asp  His  His  Leu  Thr
          355                      360                      365
Arg  Pro  His  Pro  Glu  Arg  Val  Pro  Phe  Leu  Val  Ala  Glu  Thr  Pro  Arg
     370                      375                      380
Ala  Arg  His  Thr  Leu  Asp  Glu  Leu  Asn  Pro  Gln  Lys  Ser  Lys  His  Gln
385                      390                      395                      400
Gly  Val  Arg  Lys  Ala  Lys  Trp  His  Leu  Gly  Ile  Arg  Ser  Gln  Ser  Arg
                    405                      410                      415
Pro  Asn  Asp  Ile  Met  Ala  Glu  Val  Cys  Arg  Ala  Ile  Lys  Gln  Leu  Asp
               420                      425                      430
Tyr  Glu  Trp  Lys  Val  Val  Asn  Pro  Tyr  Tyr  Leu  Arg  Val  Arg  Arg  Lys
          435                      440                      445
Asn  Pro  Val  Thr  Ser  Thr  Phe  Ser  Lys  Met  Ser  Leu  Gln  Leu  Tyr  Gln
     450                      455                      460
Val  Asp  Ser  Arg  Thr  Tyr  Leu  Leu  Asp  Phe  Arg  Ser  Ile  Asp  Asp  Glu
465                      470                      475                      480
Ile  Thr  Glu  Ala  Lys  Ser  Gly  Thr  Ala  Thr  Pro  Gln  Arg  Ser  Gly  Ser
                    485                      490                      495
Ile  Ser  Asn  Tyr  Arg  Ser  Cys  Gln  Arg  Ser  Asp  Ser  Asp  Ala  Glu  Ala
               500                      505                      510
Gln  Gly  Lys  Pro  Ser  Glu  Val  Ser  Leu  Thr  Ser  Ser  Val  Thr  Ser  Leu
          515                      520                      525
Asp  Ser  Ser  Pro  Val  Asp  Val  Ala  Pro  Arg  Pro  Gly  Ser  His  Thr  Ile
     530                      535                      540
Glu  Phe  Phe  Glu  Met  Cys  Ala  Asn  Leu  Ile  Lys  Ile  Leu  Ala  Gln
545                      550                      555
```

The present invention also comprises the following clauses:

1. A population of small extracellular vesicles (sEVs) capable, when administered systemically, of significantly decreasing the activation levels of AMP-activated protein kinase (AMPK) in SF1 expressing neurons located in the ventromedial nucleus of the hypothalamus (VMH) in comparison to the activation levels of AMPK in untreated SF1 expressing cells, without said decrease being significantly reduced in other SF1 expressing tissues selected from the list consisting of adrenal glands, testicles, or pituitary gland;
   wherein said population of small extracellular vesicles (sEVs) is characterized by comprising at least one polynucleotide encoding a dominant negative AMP-activated protein kinase alpha 1 (AMPKα1-DN) mutant protein operably linked and under the control of a steroidogenic factor 1 (SF1) promoter, wherein the sEVs are engineered to transiently express in their outer membrane at least one fusion protein comprising the neurotrophic rabies virus (RVG) peptide fused to lysosome-associated membrane protein 2b, and wherein said composition is for use in the treatment of obesity via the systemic route of administration in a subject in need thereof.

2. The population for use according to clause 1, wherein the treatment further provides ameliorating or reduction of the rebound effect during and/or after treatment washout.
3. The population for use according to any of clauses 1 or 2, wherein the dominant negative AMP-activated protein kinase alpha 1 (AMPKα1) mutant protein encoded by the at least one polynucleotide comprises an amino acid sequence with at least 95% sequence identity, over its full length, with SEQ ID NO: 1.
4. The population for use according to any of clauses 1 to 3, wherein the at least one polynucleotide encoding for the dominant negative AMP-activated protein kinase alpha 1 (AMPKα1) mutant protein comprises a polynucleotide sequence with at least 95% sequence identity, over its full length, with SEQ ID NO 2.
5. The population for use according to any of clauses 1 to 4, wherein the steroidogenic factor 1 (SF1) promoter comprises a polynucleotide sequence with at least 95% sequence identity, over its full length, with SEQ ID NO 3.
6. The population for use according to any of clauses 1 to 5, wherein the at least one polynucleotide encoding a dominant negative AMP-activated protein kinase alpha 1 (AMPKα1) mutant protein operably linked and under the control of a steroidogenic factor 1 (SF1) promoter comprises a polynucleotide sequence having 100% sequence identity, over its full length, with SEQ ID NO 4.
7. The population for use according to any of clauses 1 to 6, wherein the transiently expressed fusion protein comprising the neurotrophic rabies virus (RVG) peptide fused to lysosome-associated membrane protein 2b comprises an amino acid sequence with at least 95% sequence identity, over its full length, with SEQ ID NO 5.
8. The population for use according to any of clauses 1 to 7, wherein the small extracellular vesicles have a size distribution of between 30 and 150 nm.
9. The population for use according to any of clauses 1 to 8, wherein the small extracellular vesicles further comprise one or more of the specific markers selected from the groups consisting of ALIX, TSG101, CD9 or CD81, or any combination thereof.
10. The population for use according to any of clauses 1 to 9, wherein the small extracellular vesicles are characterized by lacking the GRP94 marker.
11. The population for use according to any of clauses 1 to 10, wherein the small extracellular vesicles are produced or obtained from immature antigen presenting cells characterized by having a statistically significant reduced expression of at least one T-cell activator molecule in comparison to the expression of said T-cell activator molecule in a mature antigen presenting cell.
12. The population for use according to any of clauses 1 to 11, wherein the antigen presenting cell is a dendritic cell, preferably JAWS II cell line, and wherein the at least one T-cell activator molecule is one or more T cell-activator molecule selected from the group consisting of major histocompatibility complex II (MHC-II), cluster of differentiation 80 (CD80) or cluster of differentiation 86 (CD86), or a combination thereof.
13. The population for use according to any of clauses 1 to 12, wherein the small extracellular vesicles are exosomes.
14. The population for use according to any of clauses 1 to 13, wherein the systemic route is the intravascular route.
15. The population for use according to any of clauses 1 to 14, wherein the treatment comprises reverting or ameliorating obesity.

EXAMPLES

Example 1

Methods

Cell Culture

The JAWS II dendritic cell line was purchased from the American Type Culture Collection (CRL-1194; ATCC; Manassas, VA, USA). JAWS II cells were grown in an incubator at 37° C. and 5% CO2 in a complete culture medium composed of alpha minimum essential medium (αMEM) (Lonza; Basel, Switzerland) containing ribonucleosides, desoxyribonucleosides and supplemented with 20% (vol/vol) of fetal bovine serum (FBS) (Gibco, Life Technologies; Grand Island, NY, USA), 4 mM of L-glutamine (Lonza; Basel, Switzerland), 1 mM of sodium pyruvate (Lonza; Basel, Switzerland), 1% of penicillin/streptomycin (GE Healthcare; Little Chalfont, Buckinghamshire, UK) and 5 ng/mL of murine GM-CSF (Miltenyi Biotec; San Diego, CA, USA). The mouse hypothalamic GT1-7 cell line (gently provided by Eduardo Dominguez; University of Santiago de Compostela) was cultured in a 37° C. incubator with 5% CO2 in a complete medium composed of Dulbecco's Modified Eagle Medium (DMEM) (Lonza; Basel, Switzerland) containing 4.5 g/L of glucose, 1 mM of sodium pyruvate and 1 mM of L-glutamine and supplemented with 10% FBS (Gibco, Life Technologies; Grand Island, NY, USA) and 1% of penicillin/streptomycin (GE Healthcare; Little Chalfont, Buckinghamshire, UK). The mouse neuroblastoma Neuro-2A cell line (generously provided by the laboratory Micro et Nanomédecines Translationnelles, University of Angers, France) were grown at 37° C. and 5% CO2 in a growth medium composed of DMEM supplemented with 10% (vol/vol) of FBS, 10 U/mL of penicillin, 100 μg/mL of streptomycin, 2 mM of L-glutamine and 1 mM of sodium pyruvate. Immortalized brown adipocytes from C57BL/6J mice 49 were seeded at a density of 2.5×105 cells/well in 6-well plates in DMEM containing 10% FBS, 20 mM HEPES, 1 nM T3 and 20 nM insulin until 70% to 80% confluence was reached. Then, 500 nM dexamethasone, 1 μM rosiglitazone, 125 μM indomethacin, and 500 μM 3-isobutyl-1-methylxanthine (IBMX) were added for 44 h. The cells were then cultured in media containing only T3 and insulin until they were differentiated (4-5 days). Primary cortical astrocytes were obtained from cerebral cortices of 3-day-old C57BL/6 mice and maintained in culture for 4 to 6 days. These cells were cultured in DMEM supplemented with 10% FBS.

Animals

Adult (8-12 weeks) male C57BL/6 mice (25 g; Centro de Biomedicina Experimental; Santiago de Compostela, Spain or Jackson Laboratory, USA), nude mice (NRj:NMRI-Foxn1nu/Foxn1nu; Janvier Labs; Saint Berthevin, France) and C57BL/6 homozygous UCP1 knockout (UCP1-KO; ucp1−/−) males and their corresponding wild-type littermates50 (bred in the GTH University of Lubeck, Germany) were used for the experiments. The experiments were performed in agreement with the International Law on Animal Experimentation and were approved by the USC Ethical Committee (Project ID 15010/14/006) and the University of Iowa Animal Research Committee (Protocol 8101549). Animals were housed with an artificial 12-h light (8:00 to 20:00)/12-h dark cycle, under controlled temperature and humidity conditions and allowed to free access to regular chow diet or 60% HFD (D12492; Research Diets, Inc; New Brunswick, USA) and filtered tap water for 10 weeks. For all the procedures, the animals were caged individually, and became accustomed to the handling procedure under non-stressful conditions. The experiments were performed in agreement with the International Law on Animal Experimentation and were approved by the USC Ethical Committee (15012/2020/010)

Plasmids

The Lamp2b-RVG plasmid was designed as previously described 28. Briefly, the plasmid encoding for Lamp2b sequence (gently provided by Seow Yiqi, University of Oxford) containing NheI and BamHI restriction sites was cloned into a pEGFP-C1 backbone, taking care to remove eGFP encoding sequence. RVG primers (Forward: 5'-TCG ATA CAC CAT TTG GAT GCC CGA GAA TCC GAG ACC AGG GAC ACC TTG TGA CAT TTT TAC CAA TAG CAG AGG GAA GAG AGC ATC CAA CGG GT-3'; Reverse: 5'-CCG GAC CCG TTG GAT GCT CTC TTC CCT CTG CTA TTG GTA AAA ATG TCA CAA GGT GTC CCT GGT CTC GGA TTC TCG GGC ATC CAA ATG GTG TA-3') were inserted between XhoI and BspEI at the N terminus of Lamp2b. The plasmids encoding for the dominant negative mutant of AMPKα1 under the control of the steroidogenic factor-1 (SF1) promoter (SF1-AMPKα1-DN) were purchased from Viraquest (North Liberty, IA, USA).

Small Extracellular Vesicles Generation and Isolation

JAWS II cells were seeded at a density of $5\times10^6$ cells in T75 cell culture flasks in complete culture medium (see composition above) the day before the transfection. On the transfection day, JAWS II cells were transiently transfected with Lamp2b-RVG plasmids using the MacsFectin transfection reagent (Miltenyi Biotec; San Diego, CA, USA). As indicated in the manufacturer's protocol, 20 μg of Lamp2b-RVG plasmid diluted into 350 μL of serum-free medium were added to 40 μL of MacsFectin diluted into 350 μL of serum-free medium. The mixtures were incubated for 20 min at room temperature to allow the formation of transfection complexes before being added to the cells. Twenty-four h later, the cell medium was replaced by FBS-sEV-free-medium (complete αMEM supplemented with 200,000 g twice ultra-centrifuged FBS). Forty-eight h later, the cell medium was collected, centrifuged twice at 300 g and 2,000 g for 10 min to remove cells and cell debris, respectively. The resultant supernatant was centrifuged at 20,000 g for 30 min to exclude large EVs. The sEVs pellets were further isolated from large EV-depleted supernatants by a 200,000 g centrifugation step for 2 h at 4° C. using a MLA-50 rotor in an Optima Max-XP ultracentrifuge (Beckman Coulter; Brea, CA, USA). The sEVs pellet was washed once with PBS using the same previously ultracentrifuge process before being resuspended in PBS. The sEV samples were kept at −80° C. until use.

Electron Microscopy sEVs were fixed overnight in a freshly prepared 2.5% paraformaldehyde (PFA) in 0.1 M sodium cacodylate buffer (pH 7.4). sEVs were pelleted using previously described ultracentrifugation process and resuspended in 2.5% glutaraldehyde solution. sEVs were deposited on copper grids and negatively stained with phosphotungstic acid and observed with a JEM1400 Transmission Electron Microscope (JEOL; Peabody, MA, USA) at 200 kV.

Nanoparticle Tracking Analysis (NTA)

Fifty μg of purified (i) native non-modified, (ii) Lamp2b-RVG neuronal targeted or (iii) Lamp2b-RVG SF1-AMPKα1-DN loaded sEVs were diluted in 1 mL of PBS, and size distribution was analyzed at 37° C. using the NanoSight NS 300 (Malvern Instruments; Orsay, France) according to the manufacturer's instructions.

Briefly, NTA applies the properties of both light scattering and Brownian motion of the particles of interest to obtain the size distribution of the nanoparticles in the liquid suspension. Sixty seconds videos were recorded and later analyzed by the NTA software determining the size distribution using the Stokes-Einstein equation.

Small Extracellular Vesicles Loading and Evaluation of Nucleic Content

Purified sEVs were loaded with nucleic acids—either siRNA Texas Red (System Biosciences; Palo Alto, CA, USA), GFP plasmid or SF1-AMPKα1-DN—using Exo-Fect (System Biosciences) following the manufacturer's protocol. Briefly, sEVs (50-300 μg) were incubated with 10 μL of Exo-Fect solution, 20 pmol siRNA Texas Red or 5 μg of plasmid (GFP or SF1-AMPKα1-DN) and 70 μL of PBS for 10 min at 37° C.

Then, after adding 30 μL of Exo-Quick solution (System Biosciences; Palo Alto, CA, USA), the mixture was placed at 4° C. for 30 min. The samples were then centrifugated for 3 min at 14,000 rpm to pellet the sEVs before being resuspended in an appropriate volume of PBS depending on the later use. sEVs were either used directly or stored at −80° C. until further use.

To evaluate the loading with the SF1-AMPKα1-DN plasmid, purified SF1-AMPKα1-DN loaded sEVs were treated or not with DNase I (RNase free, Qiagen, Valencia, CA, USA) diluted in RDD buffer (according to manufacturer's instructions) in absence or presence of 0.2% Triton X-100 (Thermo Fisher Scientific, Inc., Waltham, MA, USA) at 37° C. for 10 min. To inactivate DNase activity, the samples were heated at 75° C. for 10 min. Both non- and DNA-digested sEVs were then subjected to end-point PCR in presence of AMPK or GAPDH (as a control) primers (sequences below).

The products of the PCR reaction were then run on a 2% agarose gel (Sigma-Aldrich; St. Louis, MO, USA) containing 0.001% ethidium bromide. The gels were visualized in the UV light in an INFINITY VX2 1120M Gel Documentation System (Vilber Lourmat; Collégien France). • AMPK: Forward: 5'-ACG GCC GAG AAG CAG AAG CAC-3'; Reverse: 5'-TCG TGC TTG CCC ACC TTC AC-3' •GAPDH: Forward: 5'-AGT ATG TCG TGG AGT CTA C-3'; Reverse: 5'-CAT ACT TGG CAG GTT TCT C-3'.

Small Extracellular Vesicles Labelling and Bio-Distribution Analysis sEVs were stained with DID solution (excitation max: 644 nm; emission max: 665 nm) (Vybrant™ DiD Cell, Molecular Probes; Eugene, OR, USA) following the manufacturer's protocol. Briefly, sEVs were incubated with 5 μg/mL of Vybrant™ DiD Cell in PBS for 10 min at RT, washed two times in PBS with a 200,000 g ultracentrifuge step for 2 h. The resultant DID-labelled sEVs were recovered in PBS and directly used.

One hundred μg of DID-labelled native or Lamp2b-RVG sEVs were injected intravenously in nude mice. For the analysis of DID-labelled sEVs bio-distribution, the multi-spectral imaging system MAESTRO In-Vivo Fluorescence Imaging System (Cambridge Research & Instrumentation; Woburn, MA, USA) was used. DID-labelled sEVs bio-distribution was analyzed at different times (30 min, 2, 4 and 6 h) on isoflurane-sedated mice. The respective fluorescence of isolated organs (liver, spleen, lungs, heart, brain and skeletal muscle) was also analyzed following the sacrifice of the animal. The data were analyzed with the MAESTRO In-Vivo Fluorescence Imaging System software (Cambridge Research & Instrumentation).

In Vitro Treatment with sEVs

Twenty-four h before treatments with sEVs, (i) JAWS II cells were plated at a density of $2\times10^4$ cells in μ-Slide 8 Well (Ibidi; Munich, Germany) with 300 μL of complete growth medium, (ii) GT1-7 and (iii) Neuro2A cells were seeded in 6-well plates at a density of $2\times10^5$ cells in 1 mL of complete growth medium and (iv) primary cortical astrocytes were plated at a density of $5\times10^5$ cells in 1 mL of complete growth medium. On the day of the treatment, JAWS II cells were incubated with either non-loaded sEVs, siRNA Texas Red- or GFP-loaded sEVs (1 μg for all conditions) before being fixed and the respective fluorescence-siRNA Texas Red (excitation max: 596 nm and emission max: 615 nm) and GFP (excitation max: 488 nm and emission max: 509 nm)—were evaluated at different times (2, 6 and 24 h) by confocal microscopy (CLMS 700, Zeiss, ZEN fluorescence; Jena, Germany). On the other side, GT1-7, Neuro2A cells, brown adipocytes and primary cortical astrocytes cells were treated with 10 μg/mL of SF1-AMPKα1-DN loaded sEVs for 24 h before being collected and protein-extracted for later analysis.

Stereotaxic Treatment with sEVs

DIO mice were placed in a stereotaxic frame (David Kopf Instruments; Tujunga, CA, USA) under ketamine-xylazine anesthesia (50 mg/kg, intraperitoneal).

The VMH was targeted bilaterally using a 32-gauge needle (Hamilton; Reno, NV, USA), using the following stereotaxic coordinates: 1.7 mm posterior to the bregma, ±0.5 mm lateral to midline and 5.5 mm deep, as previously shown[17,18]. Two μg of control- or SF1-AMPKα1-DN loaded-sEVs were delivered at a rate of 100 nL $min^{-1}$ for 10 min (0.5 μL at each injection site). Daily measurements of body weight, food intake and BAT temperature (see below) were performed. At day 3, the animals were sacrificed, and the organs collected for further analysis (see below).

Systemic Treatment with sEVs

One hundred μg of non- or SF1-AMPKα1-DN loaded sEVs (indirect quantification by considering the total sEV protein content measured by Bradford) were injected in the tail vein of the mice each 3 days for corresponding times depending on the experiments. For the time course experiments (both SF1-AMPKα1-DN plasmid in vivo expression and UCP1 BAT expression time courses), the mice were injected once and sacrificed at corresponding time points (24 h, 48 h, 72 h and 1 week). Daily measurements of body weight, food intake and BAT temperature (see below) were performed. The animals were sacrificed at the end of the different experimental procedures, and the organs collected for further analysis (see below). Six to fifteen animals per group were used for each experiment, which were repeated 2-6 times. The β3-AR specific antagonist SR59230A ([3-(2ethylphenoxy)-1-[(1,S)-1,2,3,4-tetrahydronapth-1-ylamino]-2S-2-propanol-oxalate](3 mg/Kg/day dissolved in DMSO; Tocris Bioscience; Bristol, UK) 12, 13, 15-18, 44 was administrated subcutaneously twice a day at the onset of the cycles at 8:00 and 20:00, starting 3 days before the first intravenous injection. For the thermoneutrality experiments, the mice were housed at thermoneutral conditions (30° C.). The mice were allowed to adapt to the temperature fluctuations (2° C. increase each day for 4 days) before the 6 days experimental procedure and daily measurements as previously described.

Temperature Measurements

Skin temperature surrounding BAT and temperatures of tail base were recorded with an infrared camera (B335: Compact-Infrared-Thermal-Imaging-Camera; FLIR; West Malling, Kent, UK) and analyzed with a specific software package (FLIR-Tools-Software; FLIR; West Malling, Kent, UK), as shown 12,13,15-18, 44. In all the cases, the average temperature of the selected area was chosen. The size of that area and the landmarks were similar for all the mice. Emissivity (ε) was set at 0.95. The BAT and tail temperature recordings were performed daily during all the experimental procedures, always at the same time of the day, to gain consistency in the results analysis. The results are presented as time courses to highlight time-dependent effects or as an average of the different daily measurements performed throughout the experiments.

Indirect Calorimetry

Animals were analyzed for EE, oxygen consumption (VO2), respiratory quotient (RQ) and locomotor activity (LA) using a calorimetric system (LabMaster; TSE Systems; Bad Homburg, Germany) as in our previous reports[13,15-18,44,51]

Nuclear Magnetic Resonance

All studies were conducted on a 9.4T horizontal bore magnet (Bruker BioSpin, Ettlingen, Germany) with 440 mT/m gradients. A quadrature volume coil (7 cm in diameter) was used for body composition. NMR procedures were carried out under sevoflurane anesthesia (6% induction and 3.5% maintenance in a gas mixture of 70% NO2 and 30% 02). During MRI studies, each animal was fixed in a Plexiglas holder using a tooth bar, ear bar and adhesive tape to minimize spontaneous movement during imaging acquisition. For body composition studies, fast low angle shot (FLASH) sequences with repetition time/echo time (RT/ET)=1300/3.5 ms, number of averages (NA)=2, 30 coronal slices of 1 mm, field of view (FOV)=60×80 mm and matrix size=256×350 (in plane resolution of 0.234×0.229 mm/pixel) were acquired with and without fat suppression option to generate both "fat-suppression" and "fat" image sets.

Total acquisition time was 31 min. The MR post-processing was performed using ImageJ software (W. Rasband, NIH, USA). Semi-automatic image processing was used to create fat masks (volumes of total (Total AT), subcutaneous adipose tissue (scAT) and visceral adipose tissue (vAT)) comparing co-registered image sets with and without fat suppression option. Using a standard density for adipose tissue (0.9 g/mL) and other tissues (1.04 g/mL), we converted the MRI volumes to weights[52-54].

Positron Emission Tomography-Computed Tomography

Whole-body microPET/CT (positron emission tomography-computed tomography) images were acquired with the Albira PET/CT Preclinical Imaging System (Bruker Biospin; Woodbridge, CT, US). Mice received an injection of (7.4±1.85) MBq of 2-[18]F-Fluoro-2-Deoxy-2-Glucose ($^{18}$F-FDG) in the tail vein. The acquisition was performed 45±10 min after the $^{18}$F-FDG injections. Images were generated by using the Bruker Albira Suite Software Version 5.0. The brown fat and liver areas were delineated by using image tools implemented the AMIDE Software (http://amide.sourceforge.net/) to generate a three-dimensional spherical volume of interest with radius of 6 mm. Thus, mean standardized uptake values (SUV) were calculated[17, 18].

Sympathetic Nerve Activity (SNA) Recording

Multi-fiber recording of SNA was obtained from the nerve subserving BAT as previously described[12,15,17,18,55]. Each mouse was anaesthetized with intraperitoneal administration of ketamine (91 mg/kg body weight) and xylazine (9.1 mg/kg body weight) and underwent intubation with PE-50 to provide an unimpeded airway for the mouse to spontaneously breathe 02-enriched room air. Next, a micro-renathane tubing (MRE-40, Braintree Scientific; Braintree, MA, USA) was inserted into the right jugular vein for infusion of the sustaining anaesthetic agent, α-chloralose (initial dose: 12 mg/kg, then a sustaining dose of 6 mg/kg per h). Another MRE-40 catheter was inserted into the left carotid artery for continuous measurement of arterial pressure and heart rate. Core body temperature was monitored with a use of a rectal probe and continuously maintained at 37.5° C. Each mouse was then equipped for direct multifiber SNA from the nerves serving the sub-scapular BAT. A bipolar platinum-iridium electrode (36-gauge, A-M Systems; Sequim, WA, USA) was suspended under the nerve and secured with silicone gel (Kwik-Sil, WPI; Sarasota, FL, USA). The electrode was attached to a high-impedance probe (HIP-511, Grass Instruments; West Warwick, RI, USA) and the nerve signal was amplified at 105 times and filtered at 100-Hz and 1,000-Hz cutoffs with a Grass β5 AC pre-amplifier. The amplified and filtered nerve signal was routed to a speaker system and to an oscilloscope (model 54501A, Hewlett-Packard; Palo Alto, CA, USA) to monitor the audio and visual quality of the BAT sympathetic nerve recordings for quantification purposes. The amplified, filtered nerve signal was also directed to a MacLab analogue-digital converter (Model 8S, ADlnstruments; Colorado Springs CO, USA) containing the software (MacLab Chart Pro, version 7.0; Takoma, MD, USA) that utilizes a cursor to analyze the number of spikes per second that exceeds the background noise threshold and to a resetting voltage integrator (Model B600C, University of Iowa Bioengineering; Iowa City, IA, USA).

Under a stable isothermic (37.5° C.) condition and anesthesia, baseline BAT SNA was recorded over a 30-min period. The nerve was then cut distally to record the efferent SNA during another 15 min. Next, we measured the background noise, which was subtracted to measure real SNA, by recording the activity remaining after cutting the nerve proximal to the recording site. Afferent nerve activity was determined by subtracting the efferent from total nerve activity. During nerve recording, systolic, diastolic, and mean arterial pressure along with heart rate were measured in every animal.

Sample Processing

Mice were killed by cervical dislocation and decapitation. From each animal, the VMH, cortex, thalamus and cerebellum, as well as peripheral tissues were collected for western blotting and real-time RT-PCR and immediately homogenized on ice to preserve RNA and protein levels. Those samples and the serum were stored at −80° C. until further processing. Dissection of the VMH was performed by micro-punch procedure under the microscope, as previously described[12,13,15-18,44].

Blood Biochemistry

LH serum levels measured in duplicate using a double-antibody method and radioimmunoassay kits, supplied by Dr. AF Parlow (National Institute of Diabetes and Digestive and Kidney Diseases National Hormone and Peptide Program, Torrance, CA), as described in detail elsewhere 15,56. Serum testosterone and CORT levels were measured using RIA kits (MPBiomedicals, LLC; Santa Ana, CA, USA). Leptin circulating levels were measured using a mouse ELISA kit (#EZML-82K, Millipore; Billerica, MA, USA). Cholesterol (#1001093, Spinreact; Barcelona, Spain), triglycerides (#1001314, Spinreact; Barcelona, Spain), free fatty acids (NEFA Standard: 270-77000 and NEFA-HR R2 set: 436-91995 WAKO; Neuss, Germany) circulating levels and AST (#41272, AST) and ALT (#41282, ALT) activities (Spinreact; Barcelona, Spain) were measured by spectrophotometry in a Multiskan GO spectrophotometer (Invitrogen-Thermofisher Carlsbad, CA, USA). GDF 15 serum levels were measured using mouse ELISA kits (Cloud Clone Corp., Wuhan, China).

Serum cytokines (IL-6 and IP-10) were measured with a Milliplex kit (Merk-Millipore, France) following the manufacturer's instructions.

RT-PCR Analysis

For testis and adrenal gland analysis, real-time PCR (SYBR GreenER™ qPCR SuperMix System; Invitrogen; Carlsbad, CA, USA) was performed as previously described 57,58 using the following specific primers: • STAR: Forward: 5'-AGT TCG ACG TCG GAG CTC TCT-3'; Reverse: 5'-TAC TTA GCA CTT CGT CCC CG-3'; • P450scc: Forward: 5'-GAT TGC GGA GCT GGA GAT GA-3'; Reverse: 5'-TCT TTT CTG GTC ACG GCT GG-3'; • 17β-HSD3: Forward: 5'-CTG AGC ACT TCC GGT GAG AG-3'; Reverse: 5'-GGC CTT TCC TCC TTG ACT CC-3'; • LH R: Forward: 5'-GAG TTC TGC CCA GTC TGC AT-3'; Reverse: 5'-AGG AAA GGA GAC TAT GGG GTC T-3'• S11: Forward: 5'-CAT TCA GAC GGA GCG TGC TTA C-3'; Reverse: 5'-TGC ATC TTC ATC TTC GTC AC-3'.

For the skeletal muscle thermogenic markers RNA levels, real-time PCR (TaqMan; Applied Biosystems; Foster City, CA, USA) was performed using the specific following primers and probes: • Atp2α2: Forward: 5'-TCC GCT ACC TCA TCT CAT CC-3'; Reverse: 5'-CAG GTC TGG AGG ATT GAA CC-3'; • Gdp2: Forward: 5'-GAA GGG GAC TAT TCT TGT GGG T-3'; Reverse: 5'-GGA TGT CAA ATT CGG GTG TGT-3'; • Pparγ: Forward: 5'-TCG CTG ATG CAC TGC CTA TG-3'; Reverse: 5'-GAG AGG TCC ACA GAG CTG ATT-3'; • Ryr1: Forward: 5'-CAG TTT TTG CGG ACG GAT GAT-3'; Reverse: 5'-CAC CGG CCT CCA CAG TAT TG-3'; • Sln: Forward: 5'-GAG GTG GAG AGA CTG AGG TCC TTG G-3'; Reverse: 5'-GAA GCT CGG GGC ACA CAG CAG-3'; • Ucp3: Forward: 5'-GAG ATG GTG ACC TAC GAC ATC A-3'; Reverse: 5'-GCG TTC ATG TAT CGG GTC TTT A-3'.

For the analysis of SF1-AMPKα1-DN expression in vivo, total RNA was isolated from tissues coming from mice sacrificed at corresponding times with Trizol (Invitrogen; Carlsbad, CA, USA) then, reverse transcribed to cDNA using M-MLV enzyme (Invitrogen; Carlsbad, CA, USA) following the supplier's protocol.

Corresponding cDNAs were used as a template in the PCR reaction containing 10 μM of each primer (see sequences below). PCR cycling conditions were designed as followed: an initial denaturation step at 95° C. for 3 min, followed by 40 cycles of denaturation at 95° C. for 30 seconds, annealing at 55° C. for 30 seconds, and extension at 72° C. for 45 seconds. PCR products were analyzed on a 2% agarose gel. The next primers were used: • SF1-AMPKα1-DN: Forward: 5'-AAA CAC CAA GGC GTA CGG AA-3'; Reverse: 5'-TGG CGG CCG CTC TAG ATT AC-3' • HPRT: Forward: 5'-GGT TAA GCA GTA CAG CCC CA-3'; Reverse: 5'-TCC AAC ACT TCG AGA GGT CC-3'.

AMPK Activity Assay

AMPK activity was measured with CycLex AMPK Kinase Assay (CY-1182; MBL International Corporation; Woburn, MA, US) according to the manufacturer's recommendations and shown by others 59,60. Briefly, 10ul of lysis buffer containing 5 μg of VMH protein was added to 90 μL of kinase assay buffer. Each sample was analyzed by duplicate, and U2OS WT or AMPK KO cell extracts were used as controls. Absorbance was measured at 450/550 nm in a MultiSkan Go (Invitrogen-Thermofisher; Carlsbad, CA, USA).

Immunohistochemistry

Brains were post-fixed overnight in 4% PFA at 4° C., equilibrated in a solution containing 30% sucrose in Tris-buffered saline (TBS, pH 7.2) and sectioned into 30 μm coronal slices on a cryostat (CM3050S, Leica; Wetzlar, Germany). Brain sections along the medial part of the medio-basal hypothalamus were selected. Brain slices were first washed with TBS, blocked with SUMI solution (0.25% porcine gelatin and 0.5% Triton X-100 in TBS, pH 7.2) and incubated overnight at 4° C. with the following primary antibodies dissolved in SUMI solution: rabbit anti-pACCα-Ser79 (PA5-17725, Invitrogen-Thermofisher; Carlsbad, CA, USA), goat anti-GFAP (SAB2500462; Sigma-Aldrich; Saint Louis, MO, USA) and goat anti-Iba1 (ab107519, Abcam; Cambridge, UK). Brain slices were washed with TBS and incubated for 2 h at room temperature with the respective secondary antibodies diluted in SUMI: donkey anti-rabbit Alexa 647 (A21206, Invitrogen-Thermofisher; Carlsbad, CA, USA) and donkey anti-goat Alexa 488 (A21206, Invitrogen-Thermofisher; Carlsbad, CA, USA). Sections were washed in TBS and incubated with DAPI (D3571, Life Technologies; Carlsbad, CA, USA) and/or NeuroTrace™ 500/525 (N21480, Invitrogen-Thermofisher; Carlsbad, CA, USA) dissolved in TBS. Images were acquired as z-stacks using a confocal microscope (TCS SP8 Leica; Wetzlar, Germany) with a glycerol-immersed 20× objective and 3 μm step size in the z-direction. ImageJ/FIJI was used to process the acquired images. The quantifications were made based on the visualization of cellular bodies using pACCα-Ser79 staining (PA5-17725, Invitrogen-Thermofisher; Carlsbad, CA, USA), which showed a predominant neuronal profiling. The presence and absence of pACCα-Ser79 in neurons within the VMH was assessed by using co-staining with Neurotrace 500/525 (N21480, Invitrogen-Thermofisher; Carlsbad, CA, USA). No distinguished cellular staining of pACCα-Ser79 were discarded as part of the quantifications.

Double SF1 and pACCα-Ser79 Immunofluorescence Staining

Mice were deeply anesthetized and perfused transcardially with 0.9% saline followed by 4% PFA. Brains were removed, postfixed overnight in 4% PFA at 4° C., washed with ice-cold 0.1 M PBS to remove excess fixative solution and, subsequently, transferred to 30% sucrose in 0.1 M PBS (pH 7.4) overnight at 4° C., before being frozen at −80° C. Twenty μm thick sections were obtained using a cryostat. Sections centered on the VMH were selected (−1.34 to −1.94 mm from bregma) and processed for double immunofluorescence staining of SF1 neurons and pACCα-Ser79.

Briefly, the brain slices were washed with 0.1 M PBS 3 times for 5 min before being incubated with a blocking solution (5% normal donkey serum in 0.1 M PBS containing 0.3% Triton X-100) for 2 h at RT. Next, the slices were washed with 0.1 M PBS twice for 5 min and then incubated with the first primary antibody (SF1, 1:200 diluted in 0.1 M PBS; ab65815, Abcam; Cambridge, UK) overnight at 4° C. Following 3 washes of 5 min in 0.1 M PBS, the slices were incubated with a donkey anti-rabbit Alexa Fluor 594 (1:1000; A21207, Life Technologies) in 0.1 M PBS for 2 h at room temperature.

As the two primary antibodies were obtained from the same specie (i.e., rabbit), the brain sections were incubated with AffiniPure Fab Fragment goat anti-rabbit IgG (1:40; 111-007-003, Jackson ImmunoResearch; West Grove, PA, USA) for 4 h at room temperature to saturate the remaining open binding sites on the first primary antibody to avoid any cross-reactivity between both anti-rabbit primary antibodies. To determine a saturating concentration of Fab Fragment antibody, we performed a titration curve to determine the optimal concentration of Fab Fragment antibody. After extensive washing, the slices were incubated with the second primary antibody (pACCα-Ser79, 1:100 diluted in 0.1 M PBS; PA5-17725, Invitrogen) overnight at 4° C. The slices were then washed 3 times with 0.1 M PBS for 5 min before being incubated with a donkey anti-rabbit Alexa 488 (1:1000; 711-545-512, Jackson ImmunoResearch) for 2 h at RT.

Following a final step composed of 3 0.1 M PBS washes, slices were mounted using DAPI-containing Vectashield (Vector Laboratories; Peterborough UK) and stored in the dark at 4° C. until imaging.

Images were acquired using a confocal Leica TCS SP-5-X microscope equipped with an oil-immersed 63× objective and using a zoom of 3×. To ensure similar imaging conditions for all pictures of VMH slices (n=4 animals per group), exact same microscope setup (laser power and gain) was used to capture all pictures. Images were imported into Fiji (NIH; Bethesda, MD, USA) where maximum intensity projections were made, and brightness and contrast were equally adjusted. For quantification, each SF1 positive neuron per section were manually selected and the intensity of pACC signal were analyzed and are expressed as percentage relative to control. Additionally, pACC levels in other hypothalamic nuclei (ARC, DMH and PVH) were quantified as negative controls of the sEV injections.

Western Blotting

For their characterization, 10 μg of sEVs were separated on PAGE. After migration, proteins were transferred to nitrocellulose membranes and incubated with the following antibodies: Alix (Biolegend; San Diego, CA, USA), CD9 (BD Pharmingen; San Diego, CA, USA), CD81, TSG101 and GRP94 (Santa Cruz Biotechnology, Dallas, TX, USA). To evaluate the transfection efficiency of the JAWS II cells with Lamp2b-RVG and its translocation to the membrane of the sEVs, purified sEVs (native or Lamp2b-RVG modified) were immunoblotted with Lamp2b (Abcam; Cambridge, UK) following the same Western Blotting protocol as described above.

Dissected VMH or peripheral tissues were homogenized and lysed with buffer with the following composition: Tris-HCl pH 7.5 50 mM, EGTA 1 mM, EDTA 1 mM, 1% Triton X-100 vol/vol, 0.1 mM sodium orthovanadate, 50 mM sodium fluoride, 5 mM sodium pyrophosphate, 0.27 M sucrose and protease inhibitor cocktail, as previously shown[12,13,15-18,44] Protein lysates were subjected to SDS-PAGE, electrotransferred on a PVDF membrane and probed with the following antibodies: pACCα-Ser79, ACCα (Cell Signaling, Danvers, MA, USA), UCP1, UCP3, Lamp2b (Abcam; Cambridge, UK), PGC1α, PGC1β, GRP94 (Santa Cruz Biotechnology, Dallas, TX, USA), β-actin, α-tubulin (Sigma-Aldrich; St. Louis, MO, USA) and GAPDH (Merck Millipore; Billerica, MA, USA), as previously described[12,13,15-18,44].

Each membrane was then incubated with the corresponding secondary antibody: anti-mouse or anti-rabbit (DAKO; Glostrup, Denmark). Values were expressed in relation to α-tubulin (for BAT, skeletal muscle and heart) or β-actin (for the rest of the analyzed tissues) protein levels. Regarding sEVs, the values were expressed in relation to the total content of protein measured by Ponceau S. Autoradiographic films were scanned and the band signals were quantified by densitometry using ImageJ-1.33 software (NIH; Bethesda, MD, USA). Representative images for all proteins are shown; in the case of the loading controls a representative gel is displayed, although each protein was corrected by its own internal control (β-actin or α-tubulin), as explained above. In all the figures showing images of gels, all the bands for each picture come always from the same gel, although they may have been spliced for clarity, which is marked with vertical lines.

Statistical Analysis

Data are expressed as mean±SEM; when data are relativized, they are given as percentage of the appropriate controls. Statistical significance was determined by two-sided (at least one-sided is specified) Student's t-test (when two groups were compared) or two-sided ANOVA (when more than two groups were compared) followed of post-hoc Bonferroni test. The relation between continuous variables was analyzed by simple correlation (Pearson's test). $P<0.05$ was considered significant.

Data Availability

The data that support the findings of this study are available from the corresponding authors upon reasonable request.

Results

Figure 1:
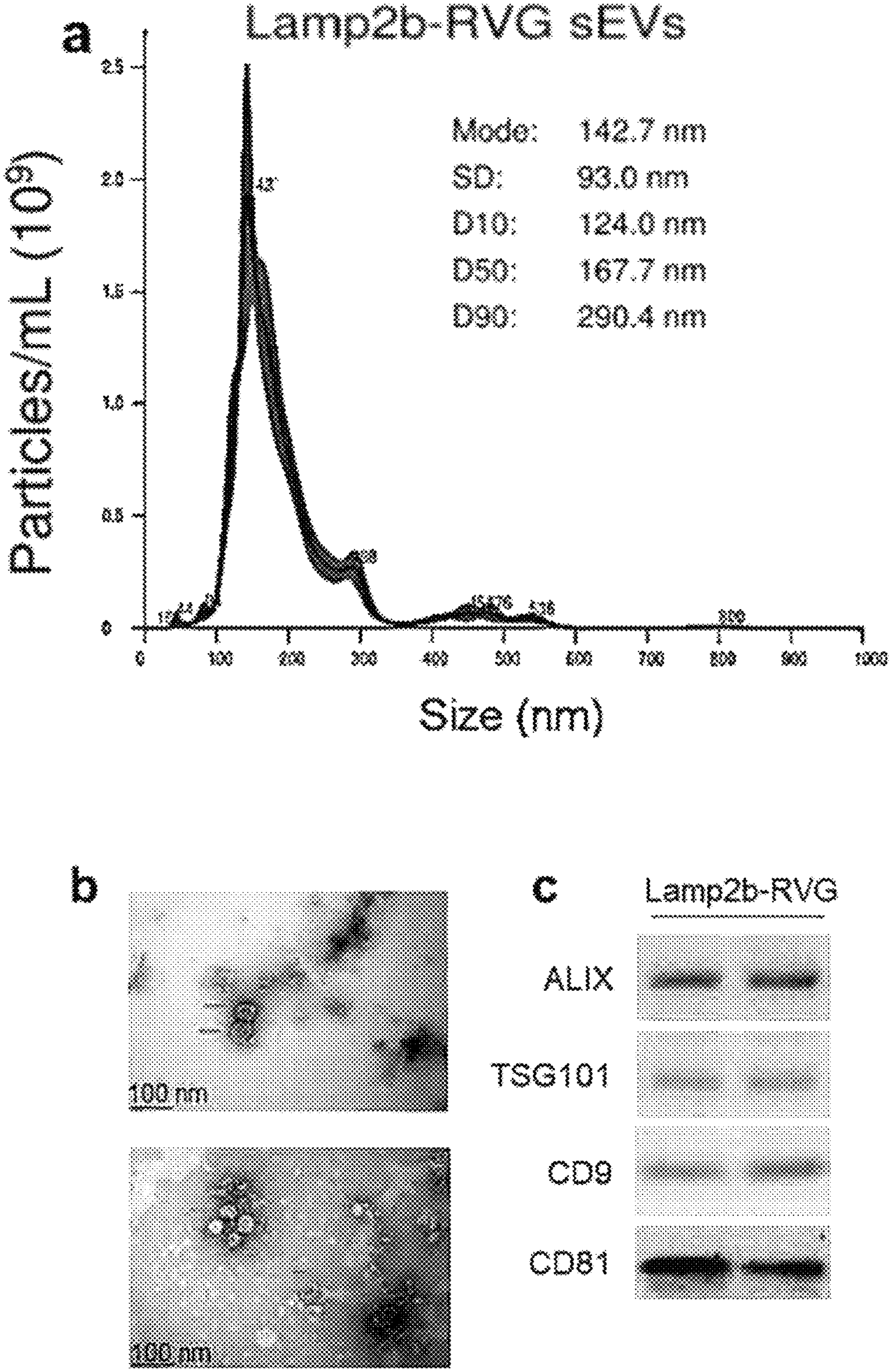
FIG. 1. Generation and characterization of neuronal-targeted dendritic cell-derived sEVs. (a) Example of curve obtained by nanoparticle tracking analysis of a sample of Lamp2b-RVG small extracellular vesicles (sEVs). The graph represents concentration of sEVs (particles/mL) according to the size (nm). (b) Electron-microscopic observation of generated Lamp2b-RVG sEVs showing specific round shape and average size of ~70 nm vesicles. (c) Western blotting using antibodies against ALIX, TSG101, CD9 and CD81 in Lamp2b-RVG sEVs. (d, e) Confocal microscopy pictures of JAWS II cells treated with non-loaded sEVs (Control), siRNA-Texas Red-loaded sEVs (sEVs-siRNA Texas Red) or GFP plasmid loaded sEVs (sEVs-GFP) at 2, 6 and 24 h. (f) Representative MAESTRO images of live mice after 30 min, 2, 4 and 6 h of intravenous injection with DID-labelled native (Control) or DID-labelled Lamp2b-RVG sEVs (Lamp2b-RVG). (g) Ex vivo quantification of DID fluorescence on isolated organs (lung, spleen, liver, heart, and kidneys) 6 h post-injection with DID-labelled native (Control, n=3) or DID-labelled Lamp2b-RVG sEVs (Lamp2b-RVG, n=4). (h) Representative images of mouse brains, black circles delimit hypothalamus, harvested 6 h post-injection of DID-labelled native (Control; n=3 mice/group) and DID-labelled Lamp2b-RVG sEVs (Lamp2b-RVG; n=4 mice/group). (i) Ex vivo quantification of DID fluorescence of mouse brains harvested 6 h post-injection of DID-labelled native (Control, n=3 mice/group) and DID-labelled Lamp2b-RVG sEVs (n=4 mice/group). j) Representative pACCα western blot images of GT1-7 cells treated for 24 h with control (non-loaded) or SF1-AMPKα1-DN loaded sEVs (n=8 samples/group). β-actin was used as control of protein loading. A black line was inserted on the immunoblots when samples were loaded on the same gel, but not side by side. (k) Quantification of pACCα in GT1-7 cells treated for 24 h with control (non-loaded, n=8 samples/group) or SF1-AMPKα1-DN loaded sEVs (n=8 samples/group). Data expressed as mean±SEM. *P<0.05, P<0.01 and *P<0.001 vs. Controls. Statistical significance was assessed by two-sided Student's t-test.
Figure 1:
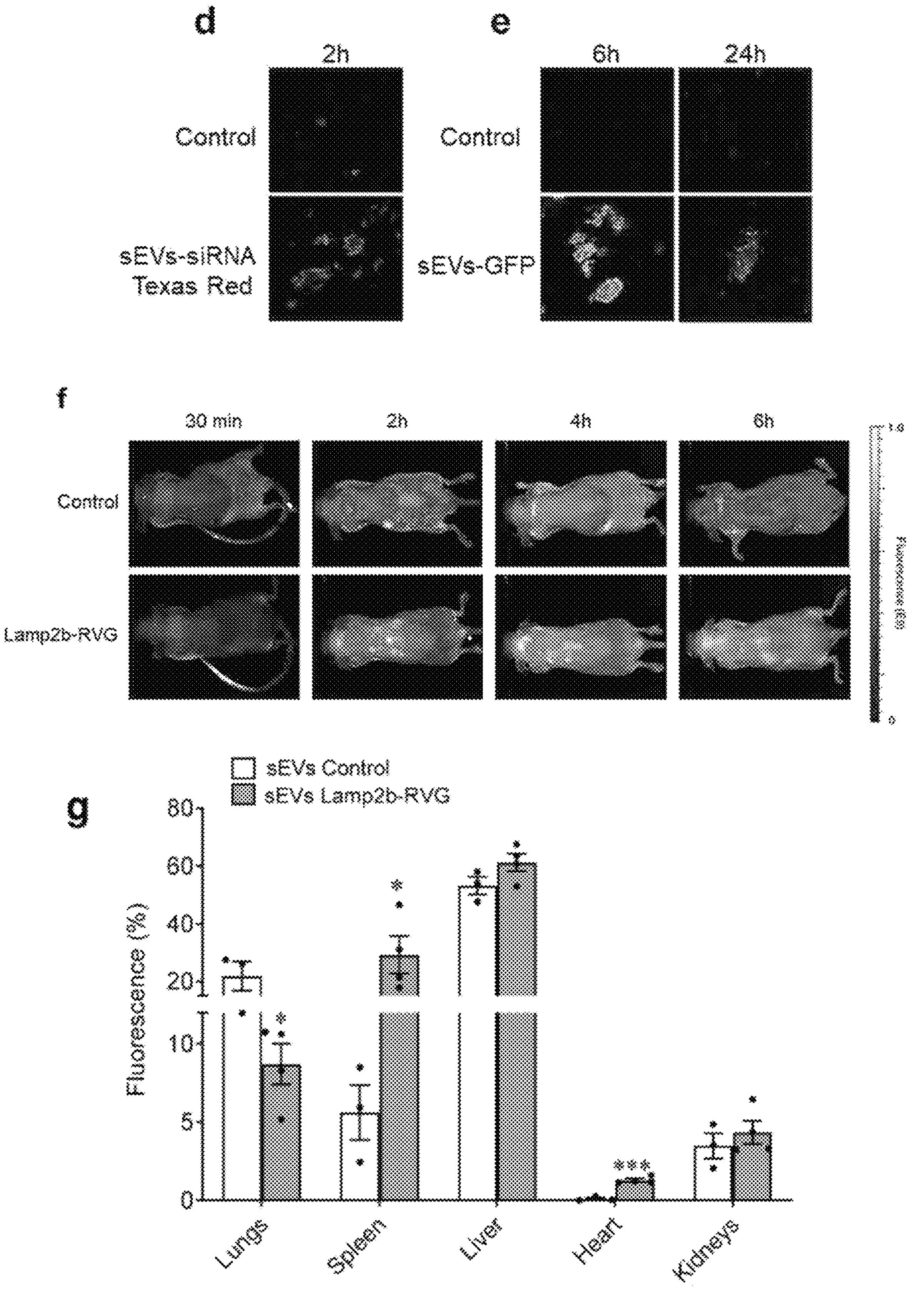
Figure 1:
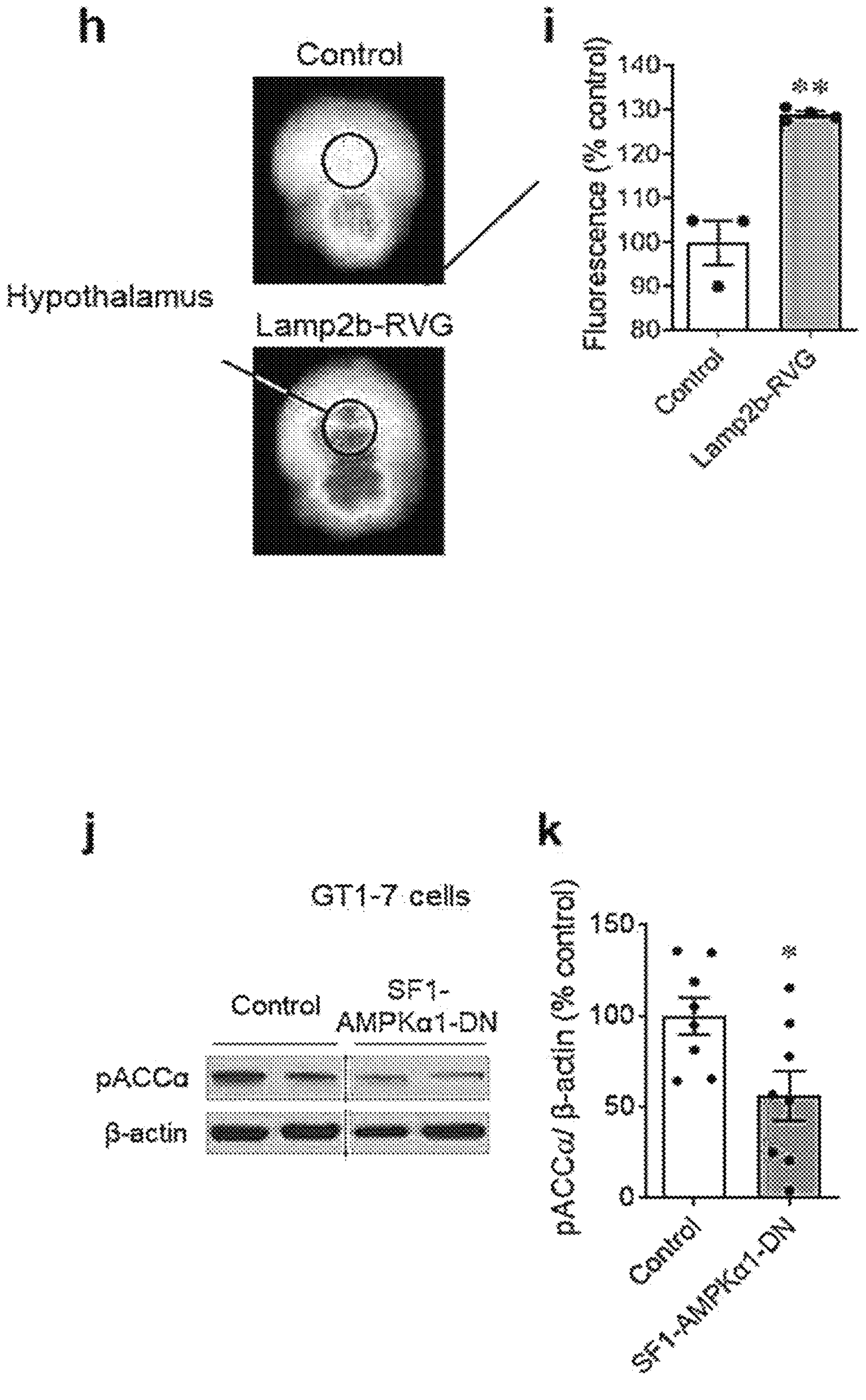
Figure 9:
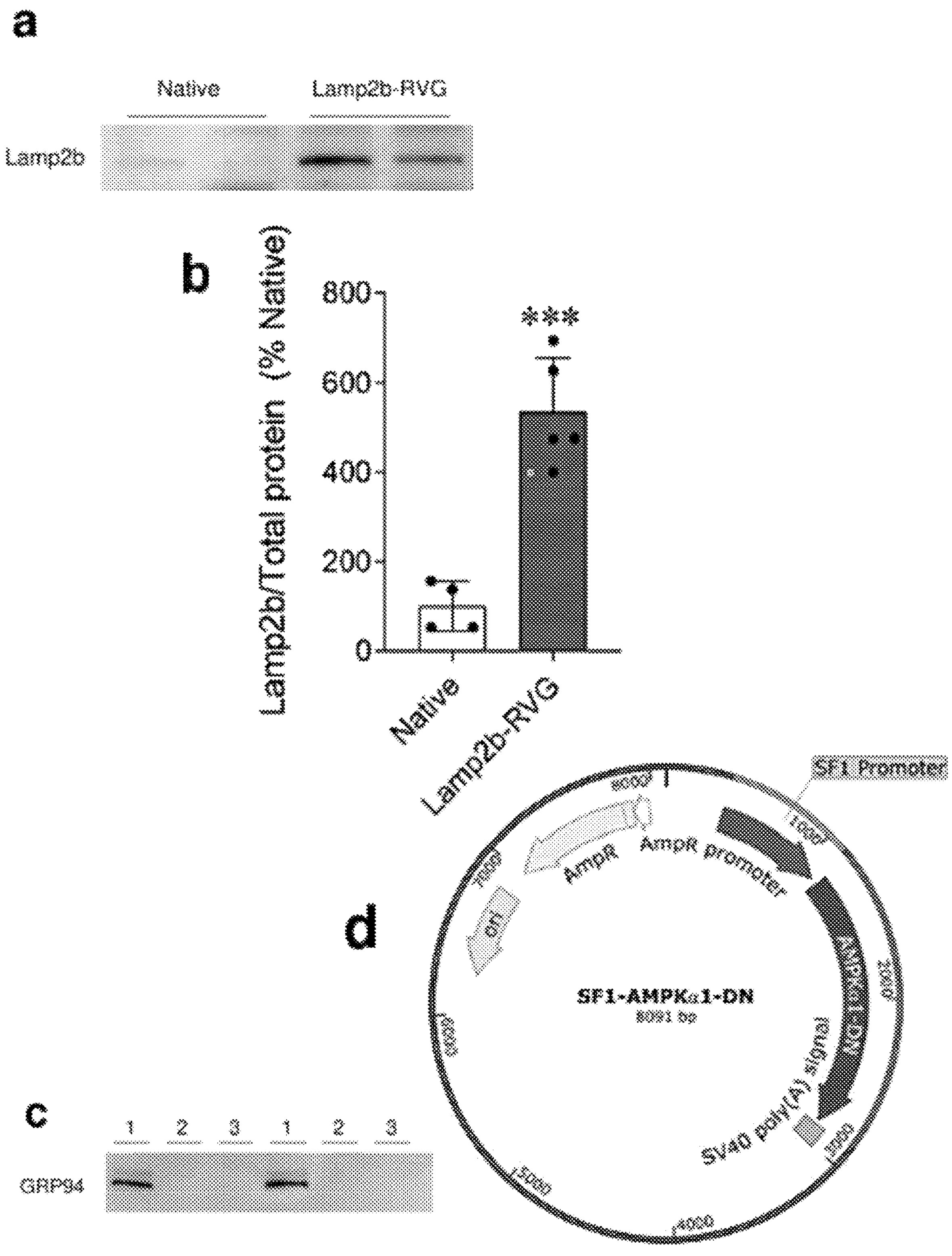
FIG. 9. Characterization of SF1-AMPKα1-DN loaded neuronal-targeted dendritic cell-derived sEVs. (a) Western blotting using antibodies against Lamp2b in native and Lamp2b-RVG sEVs. (b) Quantification of Lamp2b levels in native (n=4 samples/group) and Lamp2b-RVG (n=5 samples/group) sEVs in % of native control. (c) Western blotting using antibodies against GRP94 in Jaws II cells (lane 1), unmodified native sEVs (lane 2) and Lamp2b-RVG sEVs (lane 3). (d) Circular representation of the SF1-AMPKα1-DN encoding plasmid. (e) Example of curve obtained by nanoparticle tracking analysis of a sample of native (left panel) and SF1-AMPKα1-DN loaded Lamp2b-RVG sEVs (right panel). The graph represents concentration of sEVs (particles/mL) according to the size (nm). (f) Electron-microscopic observation of SF1-AMPKα1-DN loaded Lamp2b-RVG sEVs showing specific round shape and average size of −70 nm vesicles. (g) Agarose gel electrophoresis of native (lane 1), Lamp2b-RVG (lane 2), SF1-AMPKα1-DN loaded Lamp2b-RVG sEVs (lane 3) and negative control H2O (lane 4) of AMPK and GAPDH. (h) Agarose gel electrophoresis of SF1-AMPKα1-DN loaded Lamp2b-RVG sEVs treated with DNAse (lane 1), DNAse+Triton X-100 0.2% (lane 2) and Triton X-100 0.2% (lane 3) of AMPK and GAPDH. (i) Quantification of pACCα/ACCα expressed in % of control in primary astrocytes treated for 24 h with native (n=6 samples/group) and Lamp2b-RVG (n=6 samples/group) sEVs. j) Quantification of pACCα/ACCα expressed in % of control in Neuro2A cells treated for 24 h with native (n=6) and Lamp2b-RVG (n=6) sEVs.
Figure 9:
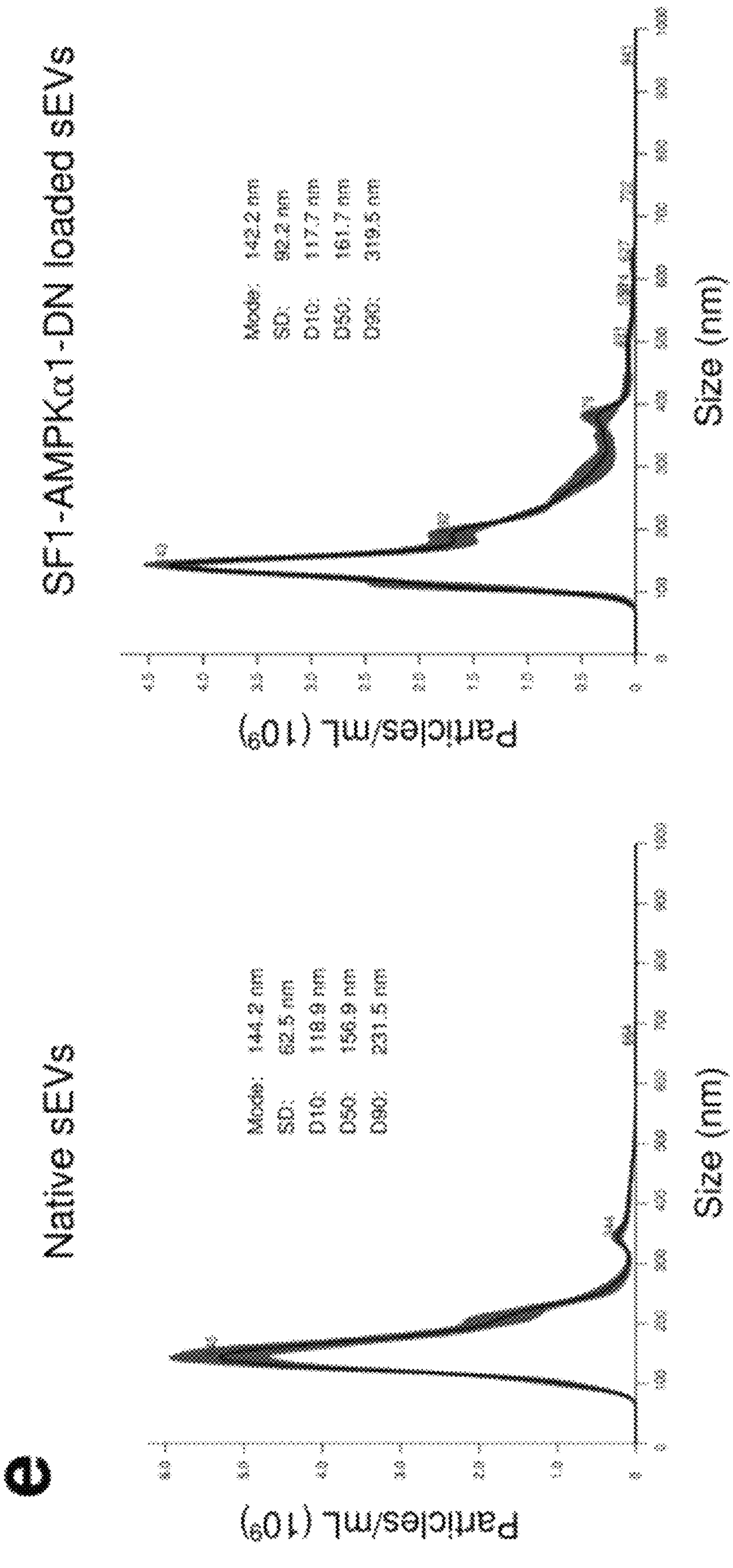
Figure 9:
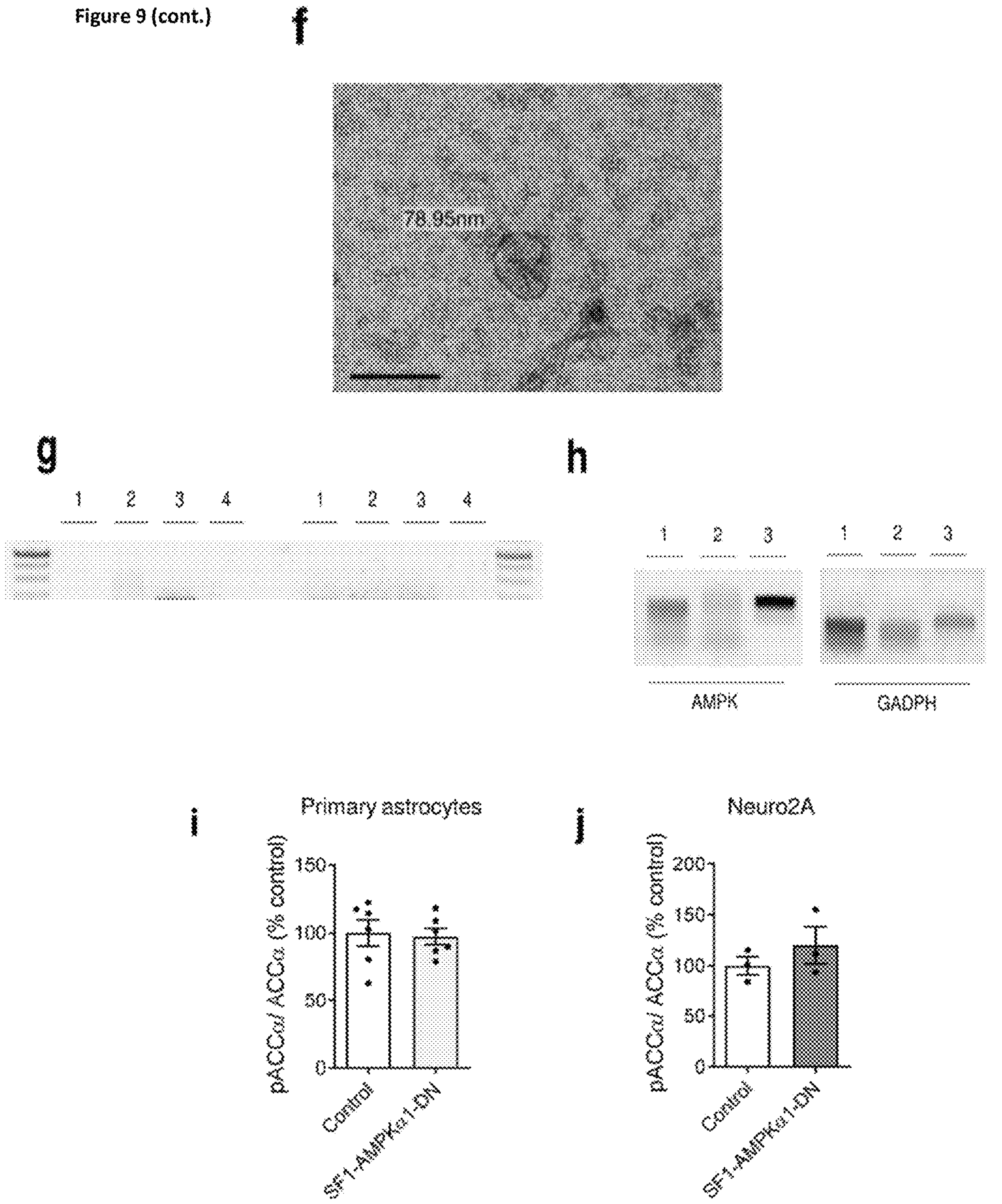

Generation and Characterization of Neuronal-Targeted Dendritic Cell-Derived sEVs As required for any delivery organic system, immunologically inert vesicles had to be designed to limit host immune reaction[27, 28]. Immature dendritic cells were used to generate large quantities of sEVs harbouring low expression of T-cell activators such as major histocompatibility complex II (MHC-II), as well as clusters of differentiation 80 and 86 (CD80 and CD86) 27,28. To confer neuronal targeting capacities to the produced sEVs, immature dendritic cells were genetically modified to transiently express a fusion protein composed of (i) lysosome-associated membrane protein 2b (Lamp2b), a protein highly expressed in sEV membranes 29, fused to (ii) a specific glycoprotein derived from the neurotrophic rabies virus (RVG) that enables the blood brain barrier (BBB) crossing through its binding to the nicotinic acetylcholine receptor (nAChR) 30, as previously reported 28. Three days after the transfection with the Lamp2b-RVG plasmid, the sEVs were isolated, purified and analysed. The neuronal targeted Lamp2b-RVG sEVs displayed higher levels of expression of Lamp2b compared to the native ones (FIG. 9*a-b*) suggesting a good integration of Lamp2b-RVG at the sEV membrane. Interestingly, it was demonstrated that using this strategy, RVG was localized at the outer membrane of the sEVs without affecting their physical properties[28]. In agreement with the literature, the Lamp2b-RVG sEVs had a size distribution between 30 and 150 nm as determined by Nanoparticle Tracking Analysis (NTA, camera level 9, shutter: 607 and gain: 15, FIG. 1*a*). These results were confirmed by electron microscopy analysis (FIG. 1*b*). The size of the sEVs obtained by the 2 different methods (NTA and electron microscopy) is slightly different. This size difference is explained by the fact that the procedure to stain the sEVs for the electron microscopy induce their dehydration, lowering their size 31. The sEVs expressed specific markers such as ALIX, TSG101, CD9 and CD81 (FIG. 1*c*), and lacked GRP94, a marker commonly used to evaluate EV purity (FIG. 9*c*).

The capacity of the sEVs to efficiently deliver nucleic acids was evaluated in vitro using fluorescent nucleic probes, a siRNA labelled with Texas Red and a green fluorescent protein (GFP) encoding plasmid. Once the sEVs were exogenously loaded with the nucleic acids, they were incubated with immature dendritic cells during 2, 6 or 24 h and the respective cell fluorescence was analysed using confocal microscopy. The siRNA-Texas Red-loaded sEVs induced red fluorescence of the immature dendritic cells after 2 h compared to the control conditions (non-loaded sEVs, FIG. 1*d*). In the same way, GFP plasmid-loaded sEVs induced green fluorescence of the immature dendritic target cells after 6 and 24 h compared to the control condition (FIG. 1*e*).

We next evaluated the ability of the Lamp2b-RVG sEVs to cross the BBB following an intravenous injection. The sEVs were labelled with a near-infrared dye, DID, which emits fluorescence when incorporated in lipid structures. To avoid any non-specific residual fluorescence of the DID, the labelled sEVs were washed twice before being injected. DID-labelled native (control) and DID-labelled Lamp2b-RVG sEVs were subsequently injected in the tail vein of nude mice. Anesthetized live mice were imaged using DID-fluorescence spectra (excitation max: 644 nm; emission max: 665 nm) at 30 min, 2, 4 and 6 h using the in vivo fluorescence imaging system MAESTRO. The level of resolution from fluorescent whole mouse imaging (FIG. 1*f*) did not allow us to determine accurately from which tissue the DID-fluorescent signal originated. Thus, the animals were sacrificed at 6 h, the different organs collected, and the fluorescence analysed ex vivo. Interestingly, the 2 populations of sEVs, native (control) and Lamp2b-RVG, mostly distributed to the lungs, the spleen and the liver, with a lower lung targeting for the Lamp2b-RVG population compared to the control one (FIG. 1*g*).

This distribution profile being consistent as these organs are highly vascularized and implicated in detoxification processes. Interestingly, the Lamp2b-RVG sEVs displayed a significantly increased localization in nAChR expressing tissues, such as the heart (FIG. 1*g*) and brain (FIGS. 1*h-i*) compared to the native sEVs control condition.

The percentage of uptake by the brain in relation to the total fluorescence was 2.3±0.3%; when fluorescence was corrected by tissue weight, the percentage of uptake ascended to 5.3±0.7% fluorescence/mg. Moreover, the DID-specific fluorescence in the brain was significantly increased using the Lamp2b-RVG targeting strategy (Control: 100±5.01; Lamp2b-RVG: 129±0.65; $P<0.01$; FIGS. 1*h-i*), confirming its suitability to increase the targeting of the sEVs to the central nervous system (CNS) 28.

Once we had demonstrated that the sEVs could reach the brain, the next step was to limit the specificity of the delivery to the exclusive VMH and specifically to the SF1 cells, which is the unique cell population expressing this factor in the CNS 32,33.

For this, we designed a plasmid encoding an AMPKα1-DN mutant expressed under the control of SF1 promoter (SF1-AMPKα1-DN) (FIG. 9*d*). The purified neuronal-targeted Lamp2b-RVG sEVs were subsequently loaded with SF1-AMPKα1-DN. Interestingly, the loading did not modify either the morphological properties or the size of the sEVs as measured by NTA at camera level 9 (shutter: 607 and gain: 15) and electron microscopy (FIG. 1*a* and FIGS. 9*e-f*). Moreover, the amount of encapsulated SF1-AMPKα1-DN plasmid was assayed with or without lysis of the sEVs with Triton X-100 0.2% (FIG. 9*g-h*) indicating the presence of the SF1-AMPKα1-DN plasmid at the membrane and inside the sEV core.

Then, we evaluated the efficacy of this strategy by assaying the phosphorylated levels of acetyl-CoA carboxylase alpha (pACCα), a main downstream target of AMPK, in the hypothalamic cell line GT1-7, which endogenously express SF1[34] and possess a number of neuronal characteristics 35 making them an excellent model for preliminary AMPK neuronal studies 36,37 The data showed that the levels of phosphorylation of ACCα were significantly decreased when GT1-7 cells were incubated for 24 h with SF1-AMPKα1-DN loaded sEVs, compared to non-loaded control sEVs (FIGS. 1*j-k*). Notably, when other CNS-derived cells not expressing SF1, such as primary astrocytes and Neuro2A cells, were incubated with SF1-AMPKα1-DN loaded sEVs, no changes were found in pACC levels (FIG. 9*i-j*). Altogether, these data indicate that the generated Lamp2b-RVG sEVs loaded with SF1-AMPKα1-DN mutants are (i) homogenous in size and morphology and are able to (ii) deliver nucleic acids, (iii) target the brain following an intravenous injection and (iv) specifically regulate AMPKα1 activity under the control of SF1 promoter in vitro.

Central Treatment with SF1-AMPKα1-DN Loaded sEVs Induced Feeding-Independent Weight Loss in Obese Mice Firstly, we assessed the efficacy of stereotaxic central delivery of SF1-AMPKα1-DN loaded sEVs in the VMH of diet-induced obese (DIO) mice that were fed with a 60% high fat diet (HFD). The results demonstrated that when administrated within this nucleus, SF1-AMPKα1-DN sEVs induced a feeding-independent weight loss for 3 days (FIGS. 2*a-b*). Next, we assayed the levels of pACCα (a surrogate marker of AMPK activity) in microdissected hypothalamic extracts, as previously shown[15-17]. Specificity of the micropunches was validated by measuring the mRNA levels of Sfl (specific marker of the VMH), proopiomelanocortin (Pomc; specific marker of the arcuate nucleus of the hypothalamus, ARC) and hypocretin/orexin (Hcrt; specific marker of the lateral hypothalamic area, LHA), respectively (FIG. 10). Our data showed that SF1-AMPKα1-DN loaded sEVs induced a significant decrease in the phosphorylated levels of ACCα in the VMH, but not in the ARC or the LHA (FIGS. 2*c-d*). This was associated with increased BAT thermogenesis as indicated by the elevated temperature in the interscapular area and enhanced BAT uncoupling protein 1 (UCP1) protein levels (FIGS. 2*e-h*). Overall, these data recapitulate the effects of virogenetic-mediated treatment with AMPKα1-DN isoforms, as well as the phenotype of SF1 AMPK null mice[12-18].

Systemic Treatment with SF1-AMPKα1-DN Loaded sEVs Modulates Hypothalamic Neuronal AMPK Activity Next, we aimed to investigate the ability of systemic administration of SF1-AMPKα1-DN loaded sEVs in modulating AMPK activity in the hypothalamus of DIO mice. Firstly, we evaluated the efficiency of our treatment by assaying the expression of the SF1-AMPKα1-DN transgene in several tissues 24 h after an intravenous injection of the loaded sEVs. The transgene was only detected in VMH samples, but not in any of the other evaluated organs including those expressing SF1 (i.e., adrenal, pituitary and testis), or those not expressing SF1 (i.e., BAT, liver, skeletal muscle, and heart) (FIG. 3*a*). Overall, this data indicated that the expression of AMPKα1-DN transgene is restricted to neuronal cells (given the RVG-dependent tropism[28,30]), including the SF1-expressing neurons of the VMH (given the SF1-driven expression), demonstrating that our strategy was specific. To confirm those results, we assayed the phosphorylation levels of ACCα in several tissues after intravenous injections. SF1-AMPKα1-DN loaded sEVs induced a significant decrease in the levels of phosphorylation of ACCα and AMPK activity in the VMH (FIGS. 3*b-d*). In keeping with this, SF1-AMPKα1-DN sEVs-treated mice showed a significantly reduced number of pACCα Ser79 positive neurons within the VMH compared to the controls, as demonstrated by the colocalization of pACCα and Neurotrace (FIGS. 3*e-f*). We also assessed the presence of pACCα in non-neuronal cells through co-staining of glial fibrillary acidic protein (GFAP, an astrocyte marker) and ionized calcium binding adaptor molecule 1 (Iba1, a microglia marker) in the VMH. However, our analysis did not detect any pACCα colocalization with GFAP or Iba1-expressing cells (FIG. 11*a-b*). To gain more insight in the specificity of our treatment, we analyzed the levels of pACCα-Ser79 in SF1 neurons of the VMH through double immunofluorescence assays. Our data showed that pACC immunoreactivity was significantly decreased in the SF1 neurons of mice treated with SF1-AMPKα1-DN sEVs (FIGS. 3*g-h*), when compared to the negative controls, demonstrating the specificity of the technique (FIG. 11*c*).

Notably, pACCα levels were not decreased in neighbouring hypothalamic nuclei such as the ARC, the dorsomedial (DMH), and the paraventricular (PVH) (FIG. 11*d*).

Overall, this evidence demonstrates that the expression of the SF1-AMPKα1-DN transgene occurs in SF1 neurons within the VMH, but not in other hypothalamic cell populations.

To further confirm the specificity of our treatment with SF1-AMPKα1-DN loaded sEVs, we investigated the pACC levels in other parts of the CNS and peripheral tissues. No changes were found in the phosphorylation levels of ACCα in any other brain areas tested (e.g., cortex, thalamus and cerebellum; FIG. 12*a*) or in peripheral tissues such as liver, adrenal gland, testis, BAT, heart and skeletal muscle (FIG. 12*b*). SF1-AMPKα1-DN loaded sEVs did not induce changes in pACCα level in primary brown adipocytes (FIG. 12*c*). These data also suggest that the potential side effects on blunting AMPK signalling in other tissues, including those that express SF1 such as testis and adrenal gland, are probably negligible. However, the use of an assay that relied on total protein extracts in peripheral tissues, where SF1 cells are scarce (for example, confined to testicular Leydig cells)[32, 33] may not be considered reliable. To overcome this limitation and further assess the possible impact of the treatment on testicular and adrenal function, we analyzed the circulating levels of testosterone and corticosterone (CORT) as well as the mRNA expression of key steroidogenic enzymes in the testis and adrenal gland of mice treated with control and SF1-AMPKα1-DN loaded sEVs. The data showed that treatment with SF1-AMPKα1-DN loaded sEVs did not induce any significant change either in testosterone circulating levels (FIG. 12*d*), or in the mRNA levels of several enzymes involved in testicular steroidogenesis such as steroidogenic acute regulatory protein (STAR), cholesterol side-chain cleavage enzyme (P450ssc) and 17ß-hydroxysteroid dehydrogenase type 3 (17ß-HSD3) (FIG. 12*e*). On the other hand, adrenal function was not impacted by the treatment with SF1-AMPKα1-DN loaded sEVs as no changes in circulating CORT (FIG. 12*f*) or in the mRNA adrenal levels of P450ssc or STAR (FIG. 12*g*) were detected. Similarly, no changes were found either in the circulating levels of luteinizing hormone (LH; FIG. 12*h*) or in the mRNA levels of the LH beta subunit (FIG. 12*i*), which pituitary production is known to be regulated by SF1[38].

Systemic Treatment with SF1-AMPKα1-DN Loaded sEVs Induced Feeding-Independent Weight Loss in Obese Mice To evaluate the efficiency of SF1-AMPKα1-DN loaded sEVs in modulating body weight, we used DIO mice. Notably, to avoid any procedure/surgery involving direct administration into the CNS, mice were injected systemically in the tail vein.

Firstly, we evaluated how long the SF1-AMPKα1-DN transgene was expressed in the VMH SF1 neurons after peripheral treatment with loaded sEVs. Our data showed that AMPKα1-DN transgene can be detected in the VMH for 24 h (FIGS. 3*i-j*). However, and keeping with the experiment involving only central administration (FIG. 2*h*), the increased BAT UCP1 expression can be detected up to 48 h following an intravenous injection (FIG. 12*j*). For these reasons, we selected a strategy based on one injection every three days for 6 days. We found that after a 6-day treatment (injections at day 0 and day 3), the intravenous injections of SF1-AMPKα1-DN loaded sEVs induced a significant and marked feeding-independent weight loss in DIO mice, when compared to control sEVs (FIGS. 4*a-d*), concomitantly with increased EE (FIG. 4*e*). However, respiratory quotient (RQ) and locomotor activity (LA) were not modified (FIGS. 4*f-g*). Of note, sEV-induced weight loss was associated with decreased adiposity, as demonstrated by nuclear magnetic resonance analysis (FIGS. 4*h-k*).

Next, we investigated the long-term effect (4 weeks, administration every 3 days) of sEV treatment in DIO mice. The results showed that when compared to mice treated with control sEVs, which normally increased their body weight, SF1-AMPKα1-DN loaded sEVs-injected DIO mice displayed a marked long-term reduction in their body weight (FIGS. 4*l-n*) with no changes in food intake (FIGS. 4*o-p*). Of note, the effect of sEVs was sustained when the treatment was withdrawn. Indeed, DIO mice treated with SF1-AMPKα1-DN loaded sEVs did not exhibit any catch up in their body weight up until 2 weeks after the injections were ceased (washout), when compared to mice treated with control sEVs (FIGS. 4*l-m*). Overall, these data indicate that the body weight loss induced by SF1-AMPKα1-DN loaded sEVs is not transient and a washout period does not imply a rebound effect enough to catch up the body weight of the control group. The weight-reducing action of sEVs was associated with a trend to decrease circulating leptin levels (FIG. 13*a*) while no changes in growth/differentiation factor 15 were observed (GDF15; FIG. 13*b*).

Assessment of circulating inflammatory markers showed no changes in interleukin-6 (IL-6) levels (FIG. 13*c*) and interferon gamma-induced protein 10 (IP-10) levels (FIG. 13*d*), suggesting that sEVs administration did not induce systemic inflammatory reaction. We also evaluated the effect of SF1-loaded sEVs on circulating metabolic parameters. Our data showed significant decreased non esterified fatty acids (NEFAs) circulating levels in the loaded sEVs-treated group, which would be compatible with the increased BAT thermogenesis (see below), with no changes in total triglycerides or cholesterol (FIGS. 13*e-g*). Finally, to assess the possible adverse effects of our treatment, we analysed the impact of SF1-AMPKα1-DN loaded sEVs on aspartate transaminase (AST) and alanine transaminase (ALT), but none of them were altered (FIG. 13*h-i*), therefore, excluding hepatic effects of sEVs. No changes were found either in key cardiovascular parameters, namely heart rate (FIG. 13*j*) or arterial pressure (systolic, diastolic and mean; FIG. 13*k-m*). If anything, blood pressure tended (although this was no significant) to be lower in the mice treated with SF1-AMPKα1-DN sEVs, which was consistent with the weight loss evoked by this treatment. These data point to lack of cardiovascular side effects of the AMPK-sEVs when given systemically.

Finally, to gain more insight into the time-dependent effect of SF1-AMPKα1-DN loaded sEV treatment, we performed a crossover study. In this new experimental setting, animals were injected in the tail vein following a two-cycle protocol with an intercalated non-treatment period. Therefore, once the functional effect of the first injection was not observed anymore, new injections were performed to evaluate the potency of a new treatment. The data showed that both injection cycles induced the expected feeding-independent body weight loss (FIGS. 4*q-s*).

Figure 5:
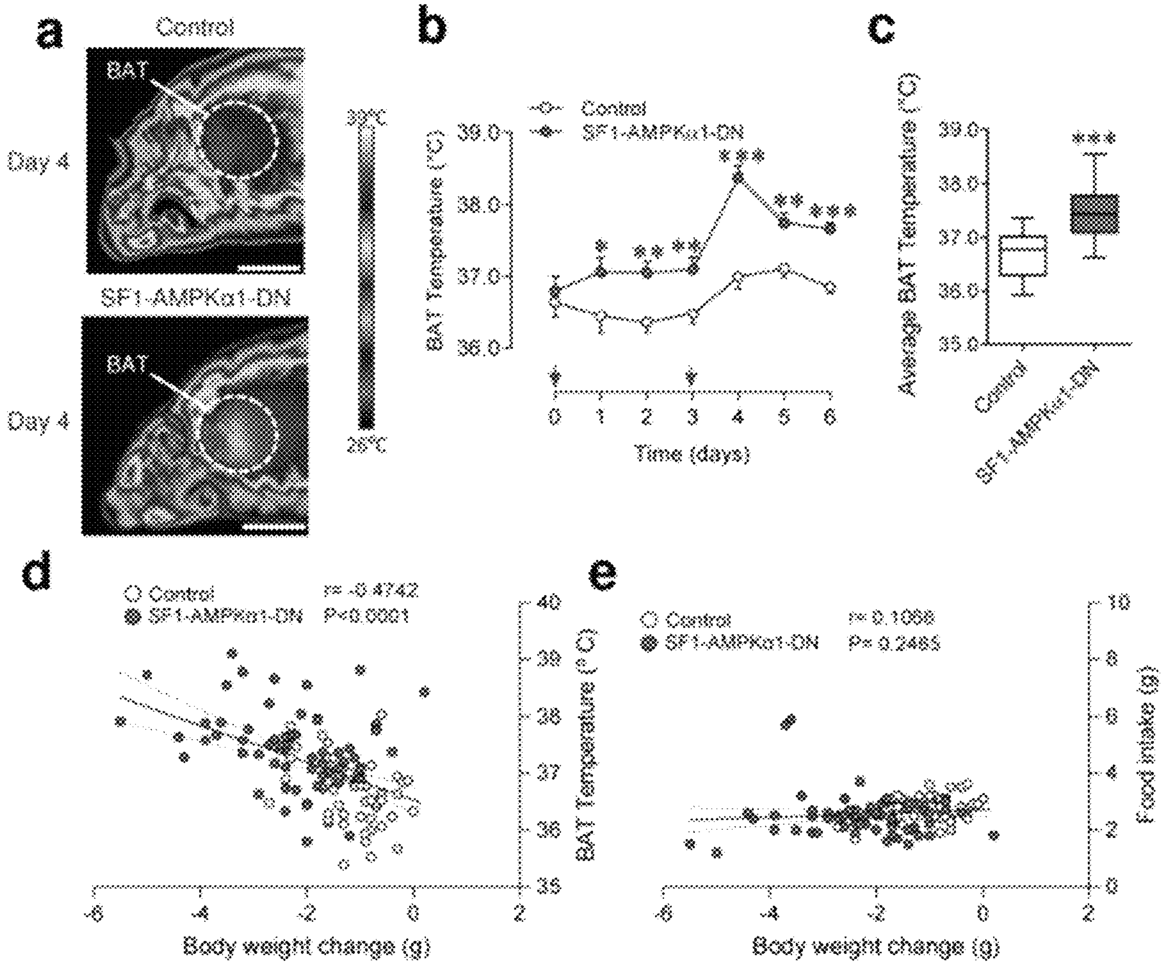
FIG. 5. Effect of systemic treatment with SF1-AMPKα1-DN loaded sEVs on BAT thermogenesis. (a-c) Representative BAT thermographic images (a), daily BAT temperature (b) (n=10 mice/group) and average BAT temperature quantification (c) [n=69-70 mice/group; box plot indicate median (middle line), 25th, 75th percentile (box) and 10th-90th percentiles (whiskers; minima and maxima, respectively)] of mice injected in the tail vein with control (non-loaded) or SF1-AMPKα1-DN loaded sEVs every 3 days for 6 days. Red arrows indicate the injections. (d, e) Correlation analyses between BAT temperature (° C.) (d) and food intake (e) and body weight changes in grams (n=60 individual values per group) of mice injected in the tail vein with control (non-loaded) or SF1-AMPKα1-DN loaded sEVs each 3 days for 6 days. (f-h) Representative BAT thermographic images at day 4, 14 and 23 (f), daily BAT temperature time course (g) and daily BAT temperature histograms (h) of mice after intravenous injection with control (non-loaded, n=8 mice/group) or SF1-AMPKα1-DN loaded sEVs (n=8 mice/group) every 3 days for 6 days, then 2 weeks of washout and again injections every 3 days for 6 days. (i, j) Representative tail base thermographic images (i) and average tail base temperature quantification j) of mice after intravenous injection with control (non-loaded, n=8 mice/group) or SF1-AMPKα1-DN loaded sEVs (n=8 mice/group) every 3 days for 6 days, then 2 weeks of washout and again injections every 3 days for 6 days. Data expressed as mean±SEM. *P<0.05, P<0.01 and *P<0.001 vs. Control. Statistical significance was assessed by two Student's t-test; except for BAT Temp at day 2 and day 23 in the crossover experiment (g) in where one-side Student's t-test was used.
Figure 5:
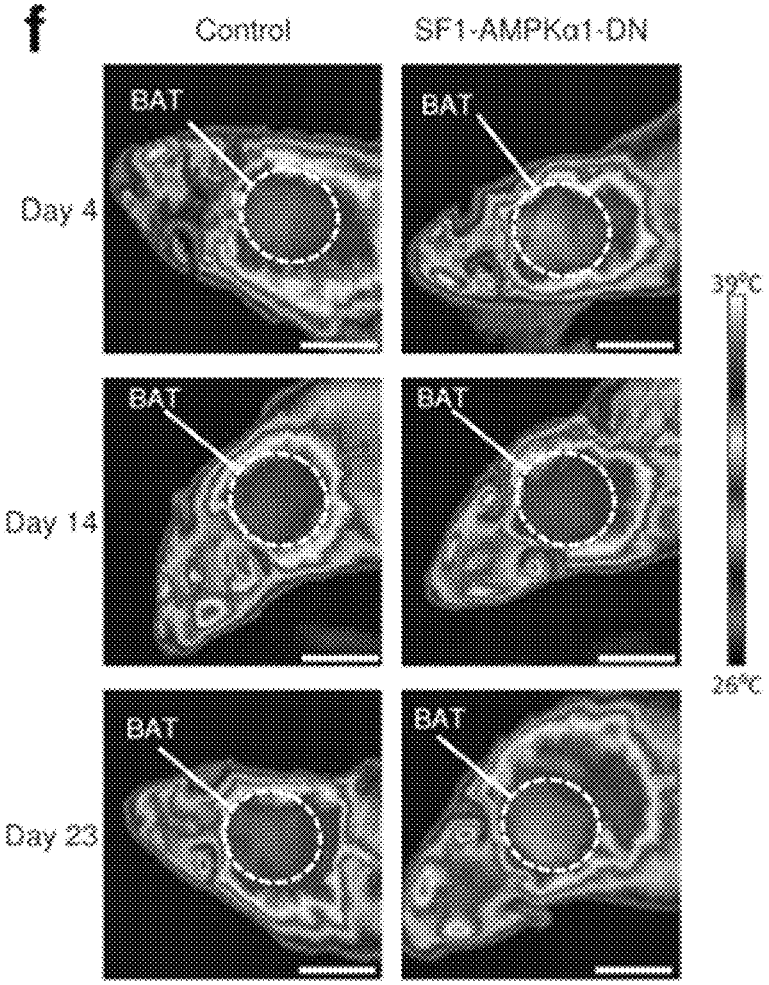
Figure 5:
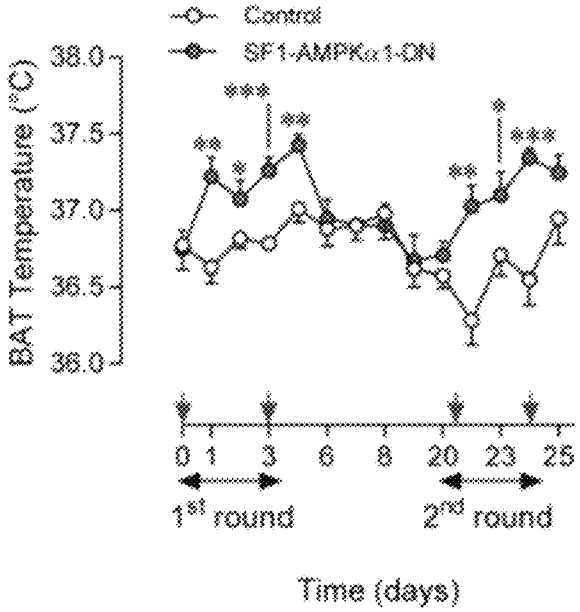
Figure 5:
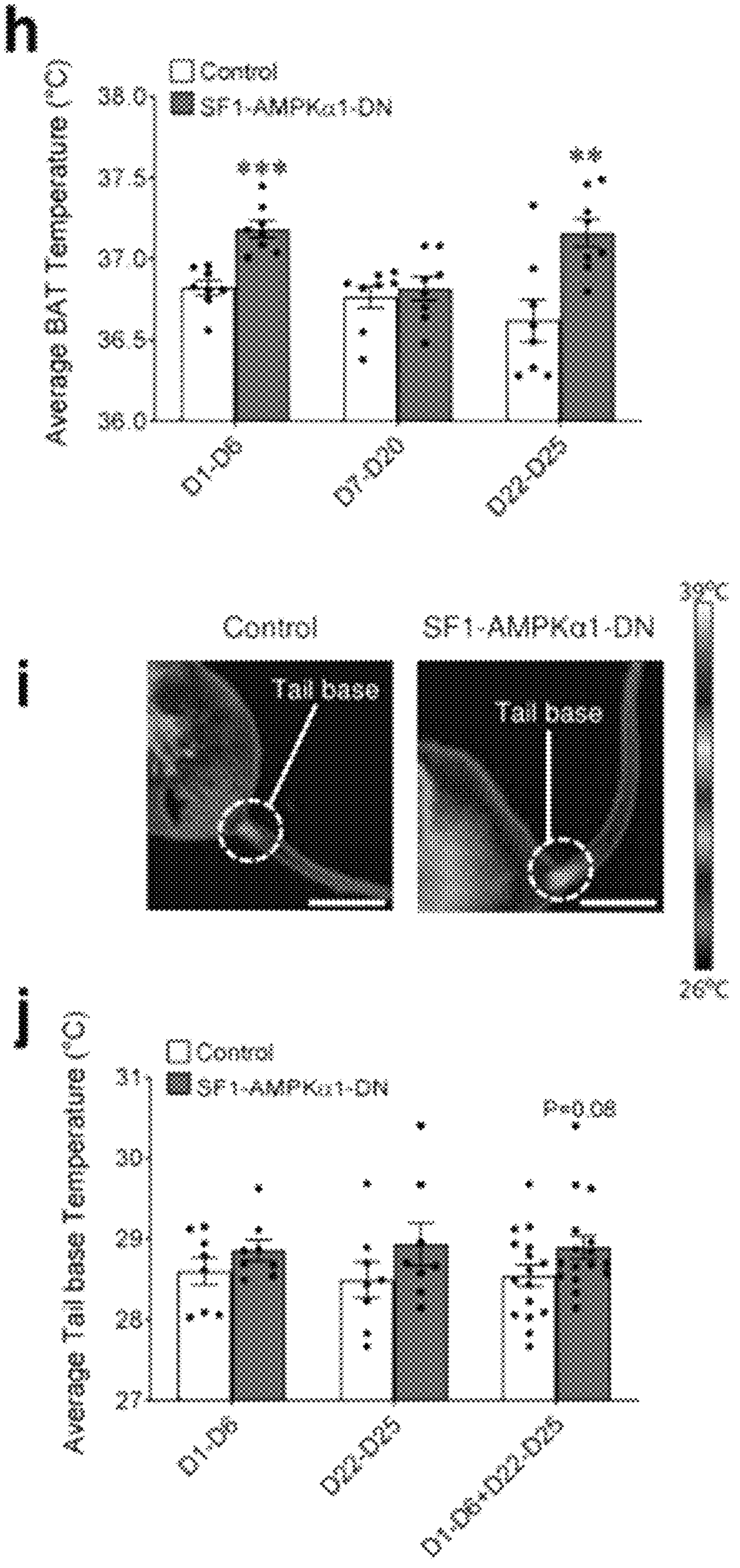

Systemic Treatment with SF1-AMPKα1-DN Loaded sEVs Increased BAT Thermogenesis in Obese Mice Next, we examined whether the feeding-independent weight loss observed in DIO mice treated with SF1-AMPKα1-DN loaded sEVs might be linked to elevated BAT thermogenesis. This was justified by the fact that previous evidence has shown that genetic inhibition or ablation of AMPKα1 in those hypothalamic cells promoted brown fat activity 12-18,23 and by the data of our stereotaxic (FIGS. 2*e-h*) and time-response experiments (FIG. 12*j*). Mice treated with SF1-AMPKα1-DN loaded sEVs exhibited higher BAT temperature beginning at day 1 after injection which lasted for the entire treatment (FIGS. 5*a-c*).

The presented evidence suggested that peripheral treatment with SF1-AMPKα1-DN loaded sEVs induced a BAT thermogenic-, but not feeding-, associated decrease in body weight. Therefore, before performing mechanistic experiments involving regulation of BAT function, we aimed to address the possible correlations between these variables. Our data revealed a highly significant negative correlation between body weight change and BAT temperature ($P<0.0001$): the mice that received the SF1-AMPKα1-DN loaded sEVs being the ones that lost most weight and had higher BAT temperature (FIG. 5*d*). Notably, food intake was similar in both groups and no association was found (FIG. 5*e*). Altogether, this evidence suggested that increased BAT function, leading to increased EE, accounted for the body weight reducing effects of this sEV strategy. To gain further insight into the thermogenic effect of these sEVs targeting hypothalamic AMPK, we analyzed BAT temperature in the crossover experiment (FIGS. 4*q-s*). Notably, when the treatment was discontinued, the SF1-AMPKα1-DN loaded sEVs-induced BAT temperature returned to control/basal values (FIGS. 5*f-h*), indicating that the observed effect was time- and treatment-dependent.

Further, we examined their impact on tail base temperature, a well-known thermoregulatory mechanism in rodents 39. Loaded sEVs induced a slight, but not significant increase in the tail base temperature (FIGS. 5*i-j*), indicating a tendency for heat dissipation by the tail.

Figure 6:
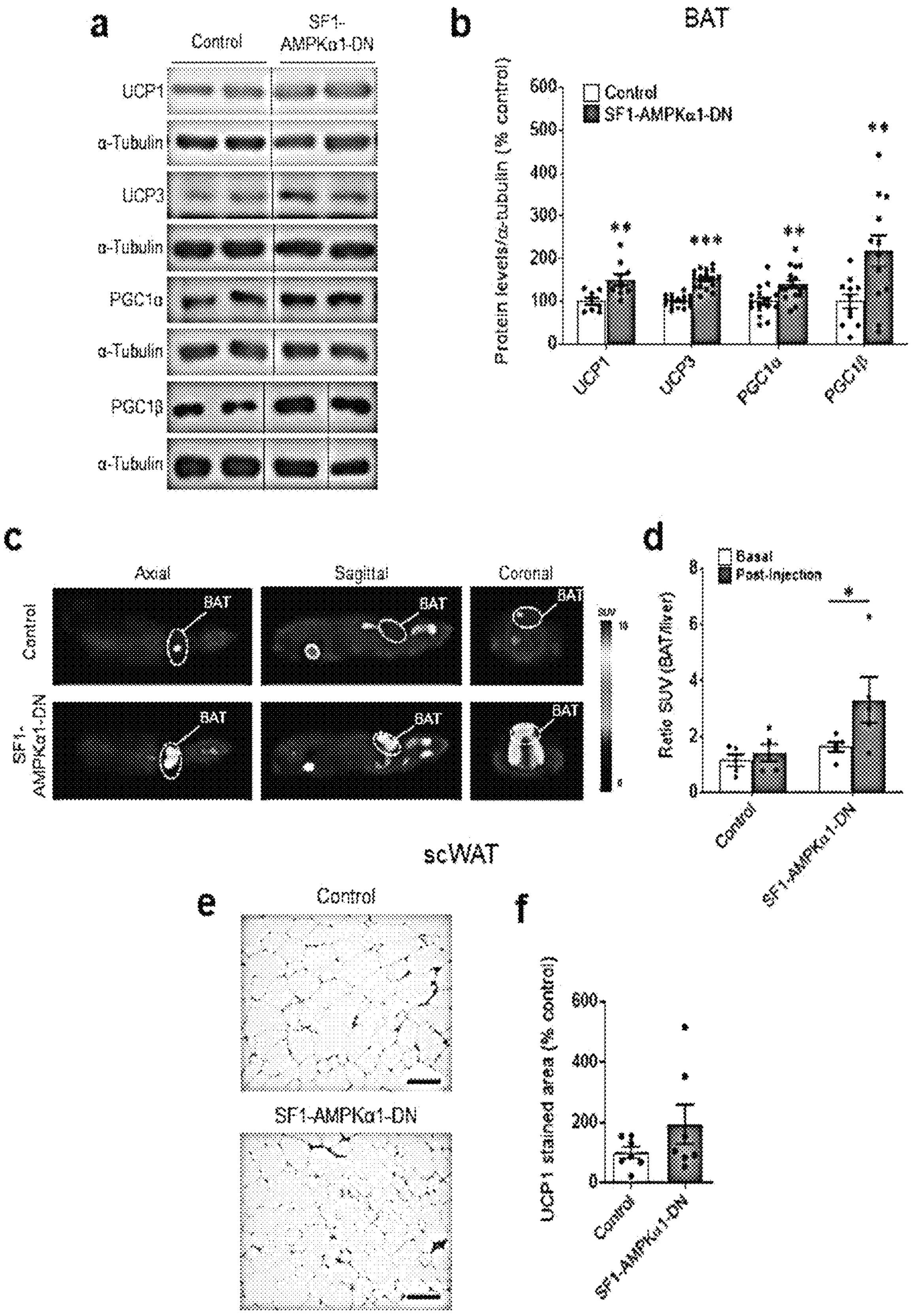
FIG. 6. Effect of systemic treatment with SF1-AMPKα1-DN loaded sEVs on BAT thermogenesis molecular pathways. (a, b) Representative UCP1, UCP3, PGC1a and PGC1β western blot images (a) and quantification of their expression (b) in BAT of mice after intravenous injection with control (non-loaded, n=8-16 mice/group) or SF1-AMPKα1-DN loaded sEVs (n=10-18 mice/group) every 3 days for 6 days. α-tubulin was used as control of protein loading. A black line was inserted on the immunoblots when samples were loaded on the same gel, but not side by side. (c, d) Representative axial, sagittal and coronal PET-CT scan images showing BAT (c) and the ratio of the standardized uptake value (SUV) BAT/liver (d) at the basal level and after injection with control (non-loaded, n=5 mice/group) or SF1-AMPKα1-DN loaded sEVs (n=5 mice/group). (e, f) Representative scWAT immunohistochemistry with anti-UCP1 antibody showing UCP1 staining (e) and quantification (f) of UCP1 stained area in scWAT from mice after injection with control (non-loaded, n=7 mice/group) or SF1-AMPKα1-DN loaded sEVs (n=7 mice/group). Scale bars represent 100 μm. Data expressed as mean±SEM. *P<0.05, P<0.01 and *P<0.001 vs. Control. Statistical significance was assessed by two-sided Student's t-test.

Systemic Treatment with SF1-AMPKα1-DN Loaded sEVs Induced BAT Thermogenic Program and Glucose Uptake The BAT of SF1-AMPKα1-DN loaded sEV-treated DIO mice displayed increased protein levels of key thermogenic markers, such as UCP1, uncoupling protein 3 (UCP3) and peroxisome proliferator-activated receptor gamma coactivator 1 α and β (PGC1α and PGC1β) (FIGS. 6*a-b* for 6 days and FIG. 14*a* for 28 days). In keeping with these data, injections of SF1-AMPKα1-DN loaded sEVs induced a higher BAT 18F-FDG uptake when compared to liver (used as a control tissue) (FIGS. 6*c-d*) indicating a higher BAT activation. Interestingly, the injection of SF1-AMPKα1-DN loaded sEVs was also associated with a non-significant trend to increase the browning of subcutaneous white adipose tissue (scWAT), as suggested by slightly increased UCP1 staining (FIGS. 6*e-f*).

Overall, this evidence indicates that the systemic administration of SF1-AMPKα1-DN loaded sEVs targeting hypothalamic SF1 neurons induces changes in BAT activity. Notably, this action is likely not associated to an unspecific action of sEVs on brown adipocytes (where SF1 is not expressed) for two main reasons: (i) it has been recently reported that the inhibition of BAT AMPKα1 caused impairment rather than activation of this tissue 40 and (ii) importantly, no changes in AMPK signalling were found in BAT after sEVs treatment either in vivo (FIG. 12*b*) or when sEVs were given to primary BAT adipocytes in vitro (FIG. 12*c*), excluding the existence of confounding unspecific actions. Moreover, no changes were found in the skeletal muscle thermogenic program (FIG. 14*b*), indicating that the increase in EE observed upon systemic administration of sEVs is driven by BAT and not muscular thermogenesis.

Figure 7:
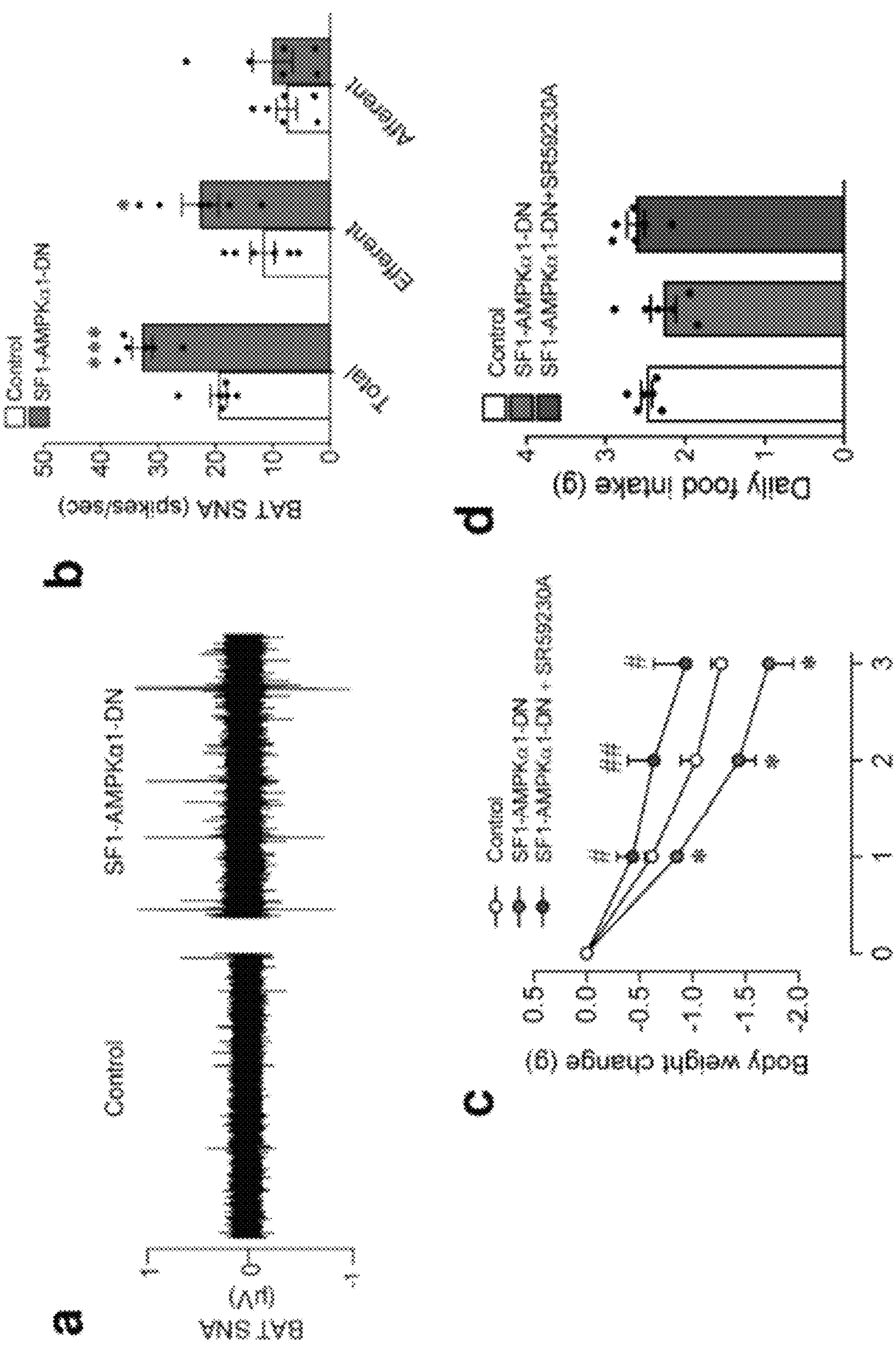
FIG. 7. Effect of adrenergic blockage on the systemic treatment with SF1-AMPKα1-DN loaded sEVs. (a, b) Representative BAT SNA tracings (a) and its quantification (b) (total, efferent and afferent signals) in spikes/sec of DIO mice injected in the tail vein with control (non-loaded; n=6 mice/group) or SF1-AMPKα1-DN (n=6 mice/group) sEVs for 24 h. (c-f) Body weight changes (in grams, c) daily food intake (in grams, d), representative BAT thermographic images (e) and average BAT temperature quantification (f) of mice injected with control (non-loaded; n=6 mice/group), SF1-AMPKα1-DN loaded sEVs alone (n=6 mice/group) or in presence of the specific β3-AR antagonist, SR59230A (n=6 mice/group). (g, h) Representative UCP1 western blot images (g) and quantification of its expression (h) in BAT of mice after intravenous injection with control (non-loaded; n=6 mice/group), SF1-AMPKα1-DN loaded sEVs alone or in presence of the specific β3-AR antagonist, SR59230A (n=6 mice/group). α-tubulin was used as control of protein loading. A black line was inserted on the immunoblots when samples were loaded on the same gel, but not side by side. Data expressed as mean±SEM. *P<0.05, P<0.01 and *P<0.001 vs. Control; #P<0.05 and ##P<0.01 SF1-AMPKα1-DN vs.SF1-AMPKα1-DN+SR59230A. Statistical significance was assessed by two-sided ANOVA.
Figure 7:
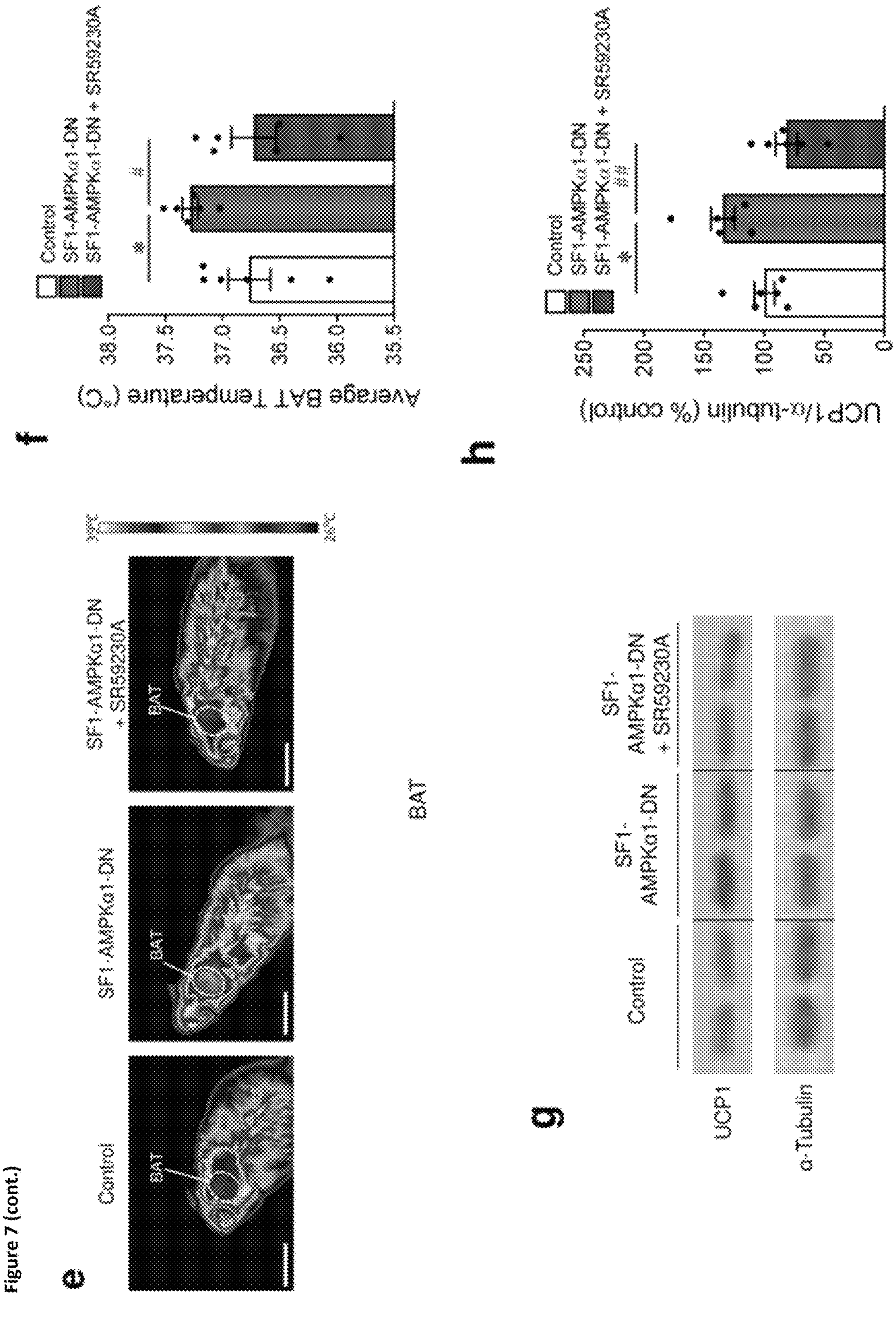

Systemic Treatment with SF1-AMPKα1-DN Loaded sEVs Induced BAT Thermogenesis and Weight Loss Through Activation of the SNS BAT thermogenesis is mainly controlled by the SNS via β3 adrenoreceptors (β3-AR) 41-43. Thus, we investigated whether the regulation of BAT following systemic injections of sEVs targeting AMPKα1 in VMH-SF1 neurons was mediated by the SNS. SF1-AMPKα1-DN loaded sEVs elevated total BAT sympathetic nerve traffic recorded directly by microneurography (FIGS. 7*a-b*). Transection of the BAT nerve distal to the recording site allowed measurement of efferent sympathetic activity. Mice treated with SF1-AMPKα1-DN loaded sEVs displayed significantly elevated efferent BAT sympathetic nerve activity (SNA) relative to controls. However, the calculated afferent BAT nerve activity was not different between the 2 groups. These data demonstrate that SF1-AMPKα1-DN loaded sEVs stimulated efferent rather than afferent sympathetic outflow, which is consistent with a centrally mediated effect of the treatment. In keeping with SNA data, pharmacological inhibition of β3-AR by subcutaneous administrations of the specific β3-AR antagonist, SR59230A[12,13,15-18,44] prevented the decrease in body weight evoked by peripheral intravenous injection of SF1-AMPKα1-DN loaded sEVs without interfering with feeding (FIGS. 7*c-d*).

Consistent with the increased weight gain after the β3-AR blockade, the treatment with SR59230A abrogated the increase in BAT temperature (FIGS. 7*e-f*) and UCP1 protein levels (FIGS. 7*g-h*). Of note, when given alone, SR59230A did not promote any changes in any of the analysed parameters (control+vehicle vs. control+SR59230A: (i) body weight: −1.27±0.09 vs. −1.30±0.42, non-significant; (ii) food intake: 2.49±0.07 vs. 2.58±0.17, non-significant; (iii) BAT temperature: 36.8±0.18 vs. 36.7±0.07, non-significant; (iv) UCP1 BAT: 100±8.2 vs. 84.1±8.3, non-significant). Overall, this evidence indicates that the systemic injection of SF1-AMPKα1-DN loaded sEVs promotes weight loss, independently of feeding, acting on SF1 neurons of the VMH, leading to increased BAT thermogenesis through the SNS via β3-AR activation. Notably, the fact that, as shown, no changes were found in key cardiovascular parameters, (FIGS. 13*j-m*) suggested that the sympathetic stimulation exerted by the sEVs was specific for BAT.

Figure 8:
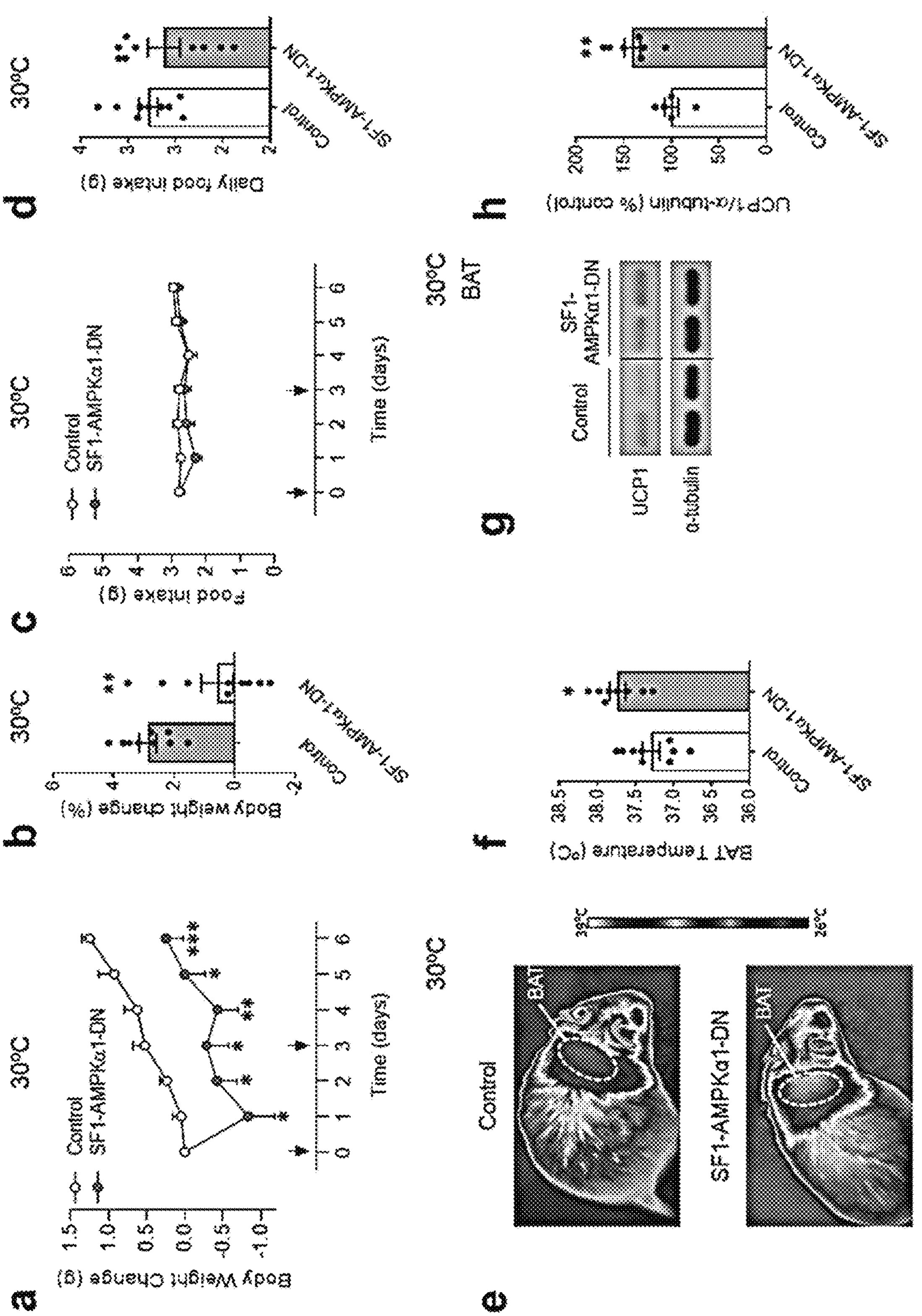
FIG. 8. Effect of systemic treatment with SF1-AMPKα1-DN loaded sEVs on energy balance in thermoneutral conditions and UCP1 knockout mice. (a, b) Body weight change expressed in grams (a) and in percentage (b) of mice after intravenous injection with control (non-loaded, n=9 mice/group) or SF1-AMPKα1-DN loaded sEVs (n=9 mice/group) every 3 days for 6 days placed under thermoneutral conditions (30° C.). (c, d) Food intake (c) and daily food intake (d) of mice after intravenous injection with control (non-loaded, n=9 mice/group) or SF1-AMPKα1-DN loaded sEVs (n=9 mice/group) every 3 days for 6 days placed under thermoneutral conditions. (e, f) Representative BAT thermographic images (e) and BAT temperature interscapular temperature quantification (f) of mice after intravenous injection with control (non-loaded, n=9 mice/group) or SF1-AMPKα1-DN loaded sEVs (n=9 mice/group) every 3 days for 6 days, placed under thermoneutral conditions. (g, h) Representative UCP1 western blot images (g) and quantification of UCP1 expression (h) in BAT of mice after intravenous injection with control (non-loaded, n=5 mice/group) or SF1-AMPKα1-DN loaded sEVs (n=7 mice/group) every 3 days for 6 days. α-tubulin was used as control of protein loading. A black line was inserted on the immunoblots when samples were loaded on the same gel, but not side by side. (i, j) Body weight change expressed in grams of wild type (ucp1+/+, i, n=7 mice/group) and ucp1 null mice (ucp1 −/−, j, n=10 mice/group) after a single intravenous injection with control (non-loaded) or SF1-AMPKα1-DN loaded sEVs. Red arrows indicate the injections. (k, 1) Daily food intake of wild type (k, n=7 mice/group) and ucp1 null mice (1, n=10 mice/group) after a single intravenous injection with control (non-loaded) or SF1-AMPKα1-DN loaded sEVs. (m-p) Representative BAT thermographic images (m, o) and BAT temperature interscapular temperature quantification (n, p) of wild type (m, n, n=7 mice/group) and ucp1 null mice (o, p, n=10 mice/group) after a single intravenous injection with control (non-loaded) or SF1-AMPKα1-DN loaded sEVs. Data expressed as mean±SEM. *P<0.05, P<0.01 and *P<0.001 vs. Control. Statistical significance was assessed by two-sided Student's t-test.
Figure 8:
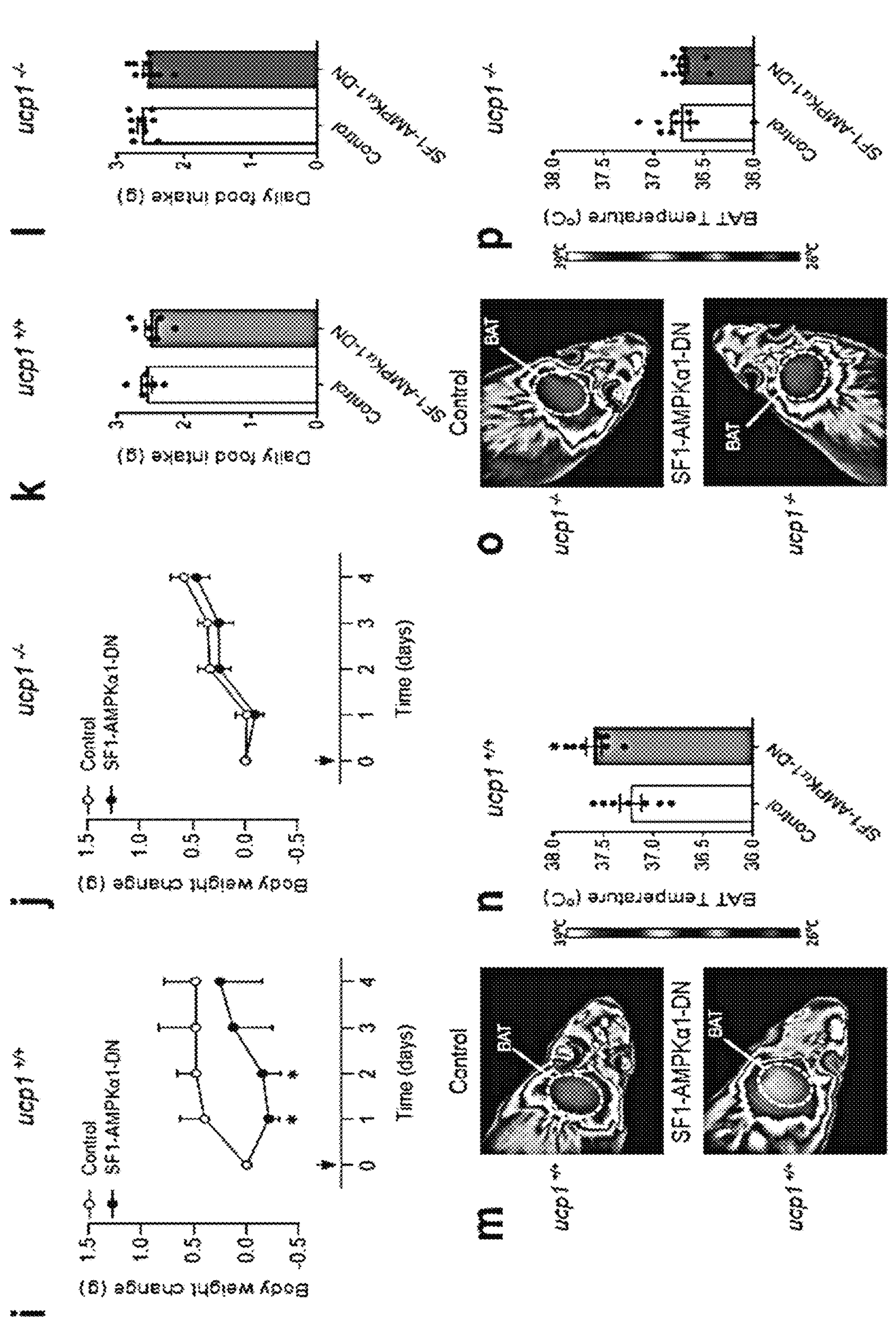

Systemic Treatment with SF1-AMPKα1-DN Loaded sEVs Induced BAT Thermogenesis and Weight Loss in Thermoneutral Conditions We aimed to investigate whether the effect of SF1-AMPKα1-DN loaded sEVs was dependent on the ambient temperature since in a non-thermoneutral environment (22-23° C. as mice are housed) the basal activation of BAT[41, 45] could mask the effects of sEVs. However, the data showed that treatment with SF1-AMPKα1-DN loaded sEVs in DIO mice housed in thermoneutral conditions (30° C.) elicited a marked body weight reduction (FIGS. 8*a-b*), independently of feeding (FIGS. 8*c-d*), and associated with increased BAT thermogenesis (FIGS. 8*e-f*) and BAT UCP1 protein content (FIGS. 8*g-h*). Overall, this evidence demonstrates that SF1-AMPKα1-DN loaded sEVs modulate energy balance and body weight by targeting BAT thermogenesis.

UCP1 is Essential for the Thermogenic and Weight Reducing Effects Evoked by Systemic SF1-AMPKα1-DN Loaded sEVs Finally, we investigated whether the effect of SF1-AMPKα1-DN sEVs on BAT thermogenesis and body weight was dependent on UCP1 expression. While SF1-AMPKα1-DN sEVs induced a feeding-independent but thermogenesis-dependent body weight decrease in wildtype mice (FIGS. 8*i*, 8*k*, 8*m* and 8*n*), this effect was totally absent in ucp1 null mice (FIGS. 8*j*, 81, 80 and 8*p*). Overall, these data demonstrate that UCP1 plays an essential role in mediating the central effects of SF1-AMPKα1-DN sEVs on thermogenesis and energy balance, and simultaneously confirm that the contributions from other peripheral tissues such as muscle are negligible.

DISCUSSION

The development of strategies to hinder the current obesity pandemic has been hampered mainly due to: (i) the intrinsic redundancy of the homeostatic mechanisms modulating body weight, (ii) the resilience to homeostatic perturbations, as a result of counterregulatory responses (i.e. decreased feeding leads to reduced EE), (iii) the limited specificity of most drugs so far available and (iv) adverse side effects[1-5]. Thus, it would be interesting to generate new genetic strategies/resources that would permit a more precise targeting, and therefore higher specificity.

Owing to their composition, sEVs can be used as shuttles of drugs and, thus, to carry molecules towards specific cells[19-22], therefore being exploited for prognosis, biomarkers and innovative therapies[19-22,24-26]. In fact, their properties, such as biocompatibility and low immunogenicity, make them ideal for reaching the CNS[27,28]. To target the central mechanism modulating energy balance, the crossing of the BBB is a major challenge in delivering agents of interest. To circumvent this limitation, engineered sEVs expressing the RVG peptide fused to Lamp2b at their surface have been developed, allowing specific neuronal targeting[28]; however, without being specific of one neuronal population of any given brain region. We took advantage of this approach using sEVs as cargos of a DNA plasmid of interest in an obesity-driven context. Therefore, in this study, we developed sEVs as delivery tools for targeting a central and canonical pathway modulating energy balance, namely hypothalamic AMPK[3,8,11], specifically in SF1 neurons of the VMH.

Notably, AMPK actions exhibit a high anatomic and isoform-dependent specificity: while anorexia is elicited by the selective ablation of the AMPKα2 isoform in agouti-related protein (AgRP) neurons of the hypothalamic arcuate nucleus (ARC)[46], the inhibition of AMPKα1 activity in SF1 neurons of the VMH increases energy expenditure by stimulating SNS-driven BAT thermogenesis[17,18] Of note, mice with selective ablation of AMPKα1 in SF1 neurons are resistant to DIO 18, which suggests that targeting this isoform in that hypothalamic population might be an interesting target against obesity. However, the implementation of this strategy required a high level of hypothalamic specificity as any side effect related to peripheral inhibition of AMPK would have the opposite effect, worsening insulin resistance and diabetes[3,47,48] thus raising the importance of the specificity and safety of the treatment. Therefore, we developed sEVs exogenously loaded with a plasmid encoding for an AMPKα1-DN mutant under the control of SF1 promoter. Notably, to circumvent any central/brain manipulation, and to be in a condition that would be acceptable for a potential therapeutically use, these sEVs were peripherally administered in the tail vein. Remarkably, the data showed that SF1-AMPKα1-DN loaded sEVs promoted a marked feeding-independent weight reducing effect due to increased SNS-mediated UCP1-dependent BAT thermogenesis (as demonstrated by the lack of effect in ucp1 null mice) and not associated with either systemic inflammatory responses or hepatic and cardiovascular side effects. Notably, the fact that the action occurs in the absence of appetite compensatory changes in the SF1-AMPKα1-DN loaded sEVs injected mice has translational relevance because it excludes undesired rebound effects, which typically characterize dietary interventions[5], as demonstrated also by our long-term and crossover treatments.

Remarkably, despite reaching peripheral tissues, SF1-AMPKα1-DN loaded sEVs only modulated AMPK signalling in the VMH, and specifically in SF1 neurons, as demonstrated by our colocalization analyses. This is due to (i) the RVG-mediated tropism for neurons 28 and (ii) the SF1-driven expression of the AMPKα1-DN transgene. Of note, no detectable changes in AMPK activity were found in (i) other hypothalamic neighbouring nuclei, (ii) peripheral SF1-expressing tissues, such as the testis, the adrenal gland and the pituitary, and (iii) peripheral non-expressing SF1 tissues, such as the liver, BAT, heart and skeletal muscle. Overall, these data indicate that the systemic treatment with SF1-AMPKα1-DN loaded sEVs that we have developed was able to induce weight loss by specifically inhibiting AMPKα1 function in SF1 neurons of the VMH. This demonstrates that hypothalamic networks can be selectively targeted by peripherally conveyed agents which opens a new therapeutic possibility for obesity and other neurological disorders. To reinforce this idea, our data also showed lack of hepatic and cardiovascular side effects of the AMPK-sEVs when given systemically. This indicates that targeting of hypothalamic AMPK could bypass some of the secondary effects associated to treatments acting peripheral mechanism regulating energy balance and metabolism[5].

Strategies for the development of successful treatments against obesity have been mainly focused on peripheral approaches, given the intrinsic complexity of targeting the brain. However, the growing knowledge on the hypothalamic mechanisms controlling energy homeostasis has made evident that the specific modulation of neural circuits in discrete areas may offer new and more effective targets for drug development. Interestingly, many of the key players in energy balance that were the basis for the development of new treatments of obesity (leptin, ghrelin, glucagon-like peptide-1 agonists, glucagon, etc.)[1-6] are likely to act through hypothalamic AMPK[3].

However, targeting specific neurons in the CNS was considered a daunting task. Here, we provide evidence about the capacity of sEVs to be used as natural bio-carriers as an alternative to more traditional delivery systems in the treatment of obesity, limiting inflammatory responses and enhancing a highly selective cellular action, namely AMPKα1 in SF1 neurons in the VMH. Thus, sEVs harbouring genetic tools open a new way in the rational design of new strategies for the treatment of obesity and associated comorbidities and perhaps other neurological diseases.

Example 2

Genetic obesity falls in two categories: monogenic obesity, which is inherited in a Mendelian pattern, is typically rare, early-onset and severe; and polygenic obesity, which is the result of hundreds of polymorphisms that each have a small effect. In the case of monogenetic obesity, the therapeutic options are scarce. For example, if the mutation involves the lack of ligand, for example a hormone, (leading to a hypo-hormonal syndrome) one possibility could be a replacement therapy. That strategy has given different degrees of efficiency, depending on the factor. However, when the mutation occurs on a receptor, such as leptin receptor (LEPR), or melanocortin 4 receptor (MC4R), the therapeutic options are more limited, and even bariatric surgery may fail.

Hypothalamic AMP-activated protein kinase (AMPK) is a canonical regulator of energy balance and metabolism at the whole-body level. AMPK is a key downstream factor for both leptin's anorectic and brown adipose tissue (BAT) thermogenic actions. We have used small extracellular vesicles (exosomes) as cargos of DNA sequences, to inhibit hypothalamic AMPKα1 (using a dominant negative mutant, AMPKα1-DN) specifically in steroidogenic factor 1 (SF1) neurons of the ventromedial nucleus of the hypothalamus (VMH), a key population regulating BAT thermogenic activity. Remarkably, when diet-induced obese (DIO) mice were systemically (in the tail vein) treated with SF1-AMPKα1-DN sEVs, they displayed a marked feeding-independent weigh loss associated with sympathetic nerve activation and increased uncoupling protein 1 (UCP1)-dependent thermogenesis in BAT. Importantly, no metabolic, endocrine, or cardiovascular inflammatory reactions or other adverse effects were developed.

The aim of this study has been to use sEVs harbouring SF1-AMPKα1-DN in db/db mice to address whether: i) our strategy is valid for the treatment of genetic forms of obesity and ii) targeting central mechanism modulating BAT thermogenesis may offer a new therapeutic option for the treatment of LEPR-deficiency.

1. MATERIALS AND METHODS

1.1. Animals

Male null LEPR (db/db) and wildtype (WT) littermate mice (C57/BL/6J; 8 weeks-old; Janvier Labs) were used for the experiments. They were allowed free access to water and standard laboratory diet (Scientific-Animal-Food-Engineering). Seven to 8 mice/group were used. The experiments were performed in agreement with the International Law on Animal Experimentation and were approved by the USC Ethical Committee (15012/2020/010).

1.2 Generation, Validation, and Treatment with sEVs

To confer neuronal targeting capacities to sEVs, and to limit host immune reactions, we used immature dendritic cells which were genetically modified to express a fusion protein of lysosome-associated membrane protein 2b (Lamp2b, a protein highly expressed in sEVs membranes) fused to a specific glycoprotein derived from the neurotrophic rabies virus (RVG), which enables the blood-brain-barrier (BBB) crossing via its binding to the nicotinic acetylcholine receptor (nAChR), as shown in the previous example. sEVs were deeply characterized, as showed using electron microscopy, nanoparticle tracking analysis (NTA) membrane protein markers, as previously demonstrated {Milbank, 2021 #56494}. The sEVs were loaded with a plasmid encoding AMPKα1-DN mutant expressed under the control of SF1 promoter (SF1-AMPKα1-DN), to limit their actions to SF1 cells in the VMH. One hundred μg of non-loaded or SF1-AMPKα1-DN loaded sEVs were injected in the tail vein of the mice every 3 days for 2 weeks, as shown {Milbank, 2021 #56494}. Body weight and food intake were daily measured.

1.3. Animal Measurements

BAT temperature (B335: Compact-Infrared-Thermal-Imaging-Camera; FLIR;), and nuclear magnetic resonance (NRM; Whole Body Composition Analyzer; EchoMRI) were performed as described above.

1.4 Analytical Methods

Serum triglyceride levels, VMH acetyl-CoA carboxylase (pACCα/ACCα) and BAT UCP1 western blotting, as well as BAT and white adipose tissue (WAT) UCP1 immunostaining were performed as described using the same kits (Spinreact), antibodies [(pACCα-$Ser^{79}$ and ACCα (Cell Signaling); UCP1 (Abcam); β-actin, α-tubulin (Sigma-Aldrich), and reagents as described above. In the western blot images, all samples were loaded in the same gel, although a black line was inserted when samples were not loaded side by side.

1.5 Statistical Analysis

Data are expressed as MEAN±SEM. Statistical significance was determined by Mixed effect analysis (for time course treatments) or unpaired Student's t-test; $P<0.05$ was significant.

2. RESULTS 2.1. Systemic SF1-AMPKα1-DN sEVs Induce Weight Loss in db/db Mice

Intravenous injection of SF1-AMPKα1-DN sEVs promoted a significant feeding-independent weight loss in wildtype (FIGS. 15A, C, E and F) and db/db mice (FIGS. 15B, D, G and H), associated with decreased adiposity in db/db mice (FIGS. 15I and 15K) and serum triglyceride levels (FIGS. 15J and 15L).

2.2. Systemic SF1-AMPKα1-DN sEVs Increased Thermogenesis and Browning

Inhibition of AMPKα1 in SF1 neurons of the VMH is a canonical mechanism increasing sympathetic tone on BAT, leading to thermogenesis, increased energy expenditure and weight loss. Our data showed that intravenous injection of SF1-AMPKα1-DN sEVs decreased pACCα levels in the VMH of both mouse models (FIGS. 16A and B), demonstrating the efficacy of our treatment in inhibiting AMPK activity in this hypothalamic nucleus.

Next, we evaluated the effect of the sEV-mediated treatment on thermogenic mechanisms. Our results showed that both wildtype and db/db mice intravenously treated with SF1-AMPKα1-DN sEVs exhibited increased BAT temperature (FIGS. 16C-D), because of increased UCP1 protein levels (FIGS. 16E-F) and immunoreactivity (FIG. 16G-H). Finally, our results also demonstrated that db/db mice (but not wildtypes) displayed higher UCP1 immunoreactivity in subcutaneous WAT (sWAT), being indicative of browning (FIGS. 16I-J). Overall, this evidence demonstrated that SF1-AMPKα1-DN sEV-induced weight loss in LEPR-deficient mice (and their wildtypes) was associated to increased BAT thermogenesis and WAT browning.

3. CONCLUSIONS

Many of the current treatments against genetic forms of obesity are mechanistically grounded on replacement therapies. Such approaches are based on the use of agonists that substitutes the lack of a ligand binding to a key receptor. The search of new strategies against obesity-induced LEPR-deficiency is still an unmet clinical need. Many of these patients failed to achieve the desire therapeutic response even when treated with the new MC4R agonists.

Hypothalamic AMPK acts downstream LEPR to modulate both feeding and BAT thermogenesis. Moreover, we have shown that central targeting of AMPKα1 using a sEV-based strategy is a suitable approach against DIO in preclinical models, by specifically modulating BAT thermogenesis.

With this in mind, we evaluated the efficacy of SF1-AMPKα1-DN sEVs in db/db mice, a model of complete leptin resistance because of LEPR-deficiency. Our results demonstrated that intravenous injections of SF1-AMPKα1-DN sEVs inhibited AMPK activity in the VMH, leading to BAT thermogenesis and weight loss in wildtype and db/db mice, in which WAT browning was also increased. Notably, SF1-AMPKα1-DN sEV-induced weight loss was totally feeding-independent; this suggests that the combination of our approach with other strategies targeting appetite, such as setmelanotide or even with sEVs against AMPK in other hypothalamic cell populations regulating homeostatic and/or hedonic food intake could allow to achieve a more significant ponderal losses. This would permit a more integral treatment against LEPR deficiency, and by extension any leptin-resistant state, by targeting both sides of the energy balance equation.

Our data thus reveals for the first time that sEV-mediated targeting of hypothalamic AMPK could be a suitable approach against this form of genetic obesity, by stimulating brown fat thermogenesis and WAT browning.

REFERENCES

1. Clemmensen, C., Muller, T. D., Finan, B., Tschop, M. H. & DiMarchi, R. Current and Emerging Treatment Options in Diabetes Care. *Handb. Exp. Pharmacol* 233, 437-459 (2016).
2. Tschop, M. H., et al. Unimolecular Polypharmacy for Treatment of Diabetes and Obesity. *Cell Metab* 24, 51-62 (2016).
3. López, M., Nogueiras, R., Tena-Sempere, M. & Dieguez, C. Hypothalamic AMPK: a canonical regulator of whole-body energy balance. *Nat. Rev. Endocrinol* 12, 421-432 (2016).
4. Cui, H., López, M. & Rahmouni, K. The cellular and molecular bases of leptin and ghrelin resistance in obesity. *Nat. Rev. Endocrinol* 13, 338-351 (2017).
5. Muller, T. D., Clemmensen, C., Finan, B., Dimarchi, R. D. & Tschop, M. H. Anti-Obesity Therapy: from Rainbow Pills to Polyagonists. *Pharmacol. Rev* 70, 712-746 (2018).
6. Dragano, N. R. V., Ferno, J., Dieguez, C., Lopez, M. & Milbank, E. Recent Updates on Obesity Treatments: Available Drugs and Future Directions. *Neuroscience* (2020).

7. Kahn, B. B., Alquier, T., Carling, D. & Hardie, D. G. AMP-activated protein kinase: Ancient energy gauge provides clues to modern understanding of metabolism. *Cell Metab* 1, 15-25 (2005).
8. Schneeberger, M. & Claret, M. Recent Insights into the Role of Hypothalamic AMPK Signaling Cascade upon Metabolic Control. *Front Neurosci* 6, 185 (2012).
9. Hardie, D. G., Schaffer, B. E. & Brunet, A. AMPK: An Energy-Sensing Pathway with Multiple Inputs and Outputs. *Trends Cell Biol* (2015).
10. Carling, D. AMPK signalling in health and disease. *Curr. Opin. Cell Biol* 45, 31-37 (2017).
11. Lopez, M. AMPK Wars: the VMH Strikes Back, Return of the PVH. *Trends Endocrinol. Metab* 29, 135-137 (2018).
12. López, M., et al. Hypothalamic AMPK and fatty acid metabolism mediate thyroid regulation of energy balance. *Nat. Med* 16, 1001-1008 (2010).
13. Martínez de Morentin, P. B., et al. Nicotine induces negative energy balance through hypothalamic AMP-activated protein kinase. *Diabetes* 61, 807-817 (2012).
14. Whittle, A. J., et al. Bmp8b increases brown adipose tissue thermogenesis through both central and peripheral actions. *Cell* 149, 871-885 (2012).
15. Martínez de Morentin, P. B., et al. Estradiol regulates brown adipose tissue thermogenesis via hypothalamic AMPK. *Cell Metab* 20, 41-53 (2014).
16. Martins, L., et al. A Functional Link between AMPK and Orexin Mediates the Effect of BMP8B on Energy Balance. *Cell Rep* 16, 2231-2242 (2016).
17. Martínez-Sánchez, N., et al. Hypothalamic AMPK-ER stress-JNK1 axis mediates the central actions of thyroid hormones on energy balance. *Cell Metab* 26, 212-229 (2017).
18. Seoane-Collazo, P., et al. SF1-Specific AMPKalpha1 Deletion Protects Against Diet-Induced Obesity. *Diabetes* 67, 2213-2226 (2018).
19. Buzas, E. I., Gyorgy, B., Nagy, G., Falus, A. & Gay, S. Emerging role of extracellular vesicles in inflammatory diseases. *Nat. Rev. Rheumatol* 10, 356-364 (2014).
20. Milbank, E., Martinez, M. C. & Andriantsitohaina, R. Extracellular vesicles: Pharmacological modulators of the peripheral and central signals governing obesity. *Pharmacol. Ther* 157, 65-83 (2016).
21. Martinez, M. C. & Andriantsitohaina, R. Extracellular Vesicles in Metabolic Syndrome. *Circ. Res* 120, 1674-1686 (2017).
22. Malloci, M., et al. *Extracellular Vesicles: Mechanisms in Human Health and Disease. Antioxid. Redox. Signal* 30, 813-856 (2019).
23. López, M., et al. Hypothalamic fatty acid metabolism mediates the orexigenic action of ghrelin. *Cell Metab* 7, 389-399 (2008).
24. Tang, K., et al. Delivery of chemotherapeutic drugs in tumour cell-derived microparticles. *Nat. Commun* 3, 1282 (2012).
25. Dalli, J., et al. Microparticle alpha-2-macroglobulin enhances pro-resolving responses and promotes survival in sepsis. *EMBO Mol. Med* 6, 27-42 (2014).
26. Kamerkar, S., et al. Exosomes facilitate therapeutic targeting of oncogenic KRAS in pancreatic cancer. *Nature* 546, 498-503 (2017).
27. Quah, B. J. & O'Neill, H. C. The immunogenicity of dendritic cell-derived exosomes. *Blood Cells Mol. Dis* 35, 94-110 (2005).
28. Alvarez-Erviti, L., et al. Delivery of siRNA to the mouse brain by systemic injection of targeted exosomes. *Nat. Biotechnol* 29, 341-345 (2011).
29. Colombo, M., Raposo, G. & Thery, C. Biogenesis, secretion, and intercellular interactions of exosomes and other extracellular vesicles. *Annu. Rev. Cell Dev. Biol* 30, 255-289 (2014).
30. Kumar, P., et al. Transvascular delivery of small interfering RNA to the central nervous system. *Nature* 448, 39-43 (2007).
31. Domingos, R. F., et al. Characterizing manufactured nanoparticles in the environment: multimethod determination of particle sizes. *Environ Sci Technol* 43, 7277-7284 (2009).
32. Parker, K. L. & Schimmer, B. P. Steroidogenic factor 1: a key determinant of endocrine development and function. *Endocr. Rev* 18, 361-377 (1997).
33. Choi, Y. H., Fujikawa, T., Lee, J., Reuter, A. & Kim, K. W. Revisiting the Ventral Medial Nucleus of the Hypothalamus: The Roles of SF-1 Neurons in Energy Homeostasis. *Front Neurosci* 7, 71 (2013).
34. Corley, D. R., Li, X., Lei, Z. M. & Rao, C. V. Potential regulation of GnRH gene by a steroidogenic factor-1-like protein. *Mol. Hum. Reprod* 6, 671-676 (2000).
35. Mellon, P. L., et al. Immortalization of hypothalamic GnRH neurons by genetically targeted tumorigenesis. *Neuron* 5, 1-10 (1990).
36. Coyral-Castel, S., et al. The effect of AMP-activated kinase activation on gonadotrophin-releasing hormone secretion in GT1-7 cells and its potential role in hypothalamic regulation of the oestrous cyclicity in rats. *J. Neuroendocrinol* 20, 335-346 (2008).
37. Beall, C., et al. Mouse hypothalamic GT1-7 cells demonstrate AMPK-dependent intrinsic glucose-sensing behaviour. *Diabetologia* 55, 2432-2444 (2012).
38. Schimmer, B. P. & White, P. C. Minireview: steroidogenic factor 1: its roles in differentiation, development, and disease. *Mol. Endocrinol* 24, 1322-1337 (2010).
39. Warner, A., et al. Inappropriate heat dissipation ignites brown fat thermogenesis in mice with a mutant thyroid hormone receptor alpha1. *Proc. Natl. Acad. Sci. U. S. A* 110, 16241-16246 (2013).
40. Yang, Q., et al. AMPK/alpha-Ketoglutarate Axis Dynamically Mediates DNA Demethylation in the Prdm16 Promoter and Brown Adipogenesis. *Cell Metab* 24, 542-554 (2016).
41. Cannon, B. & Nedergaard, J. Brown adipose tissue: function and physiological significance. *Physiol Rev* 84, 277-359 (2004).
42. Morrison, S. F., Madden, C. J. & Tupone, D. Central neural regulation of brown adipose tissue thermogenesis and energy expenditure. *Cell Metab* 19, 741-756 (2014).
43. Contreras, C., et al. The brain and brown fat. *Ann. Med* 47, 150-168 (2015).
44. Gonzalez-Garcia, I., et al. Estradiol Regulates Energy Balance by Ameliorating Hypothalamic Ceramide-Induced ER Stress. *Cell Rep* 25, 413-423 (2018).
45. Alvarez-Crespo, M., et al. Essential role of UCP1 modulating the central effects of thyroid hormones on energy balance. *Mol. Metab* 5, 271-282 (2016).
46. Claret, M., et al. AMPK is essential for energy homeostasis regulation and glucose sensing by POMC and AgRP neurons. *J. Clin. Invest* 117, 2325-2336 (2007).

47. Foretz, M., Guigas, B., Bertrand, L., Pollak, M. & Viollet, B. Metformin: from mechanisms of action to therapies. *Cell Metab* 20, 953-966 (2014).

48. Foretz, M. & Viollet, B. Therapy: Metformin takes a new route to clinical efficacy. *Nat. Rev. Endocrinol* 11, 390-392 (2015).

49. Campderros, L., et al. Brown Adipocytes Secrete GDF15 in Response to Thermogenic Activation. *Obesity* (Silver Spring) 27, 1606-1616 (2019).

50. Johann, K., et al. Thyroid-Hormone-Induced Browning of White Adipose Tissue Does Not Contribute to Thermogenesis and Glucose Consumption. *Cell Rep* 27, 3385-3400e3383 (2019).

51. Seoane-Collazo, P., et al. Central nicotine induces browning through hypothalamic kappa opioid receptor. *Nat. Commun* 10, 4037 (2019).

52. Johnson, D. H., Flask, C. A., Ernsberger, P. R., Wong, W. C. & Wilson, D. L.

Reproducible MRI measurement of adipose tissue volumes in genetic and dietary rodent obesity models. *J Magn Reson Imaging* 28, 915-927 (2008).

53. Hu, H. H., Chen, J. & Shen, W. Segmentation and quantification of adipose tissue by magnetic resonance imaging. *MAGMA* 29, 259-276 (2016).

54. Hong, C. W., Fazeli Dehkordy, S., Hooker, J. C., Hamilton, G. & Sirlin, C. B. Fat Quantification in the Abdomen. *Top Magn Reson Imaging* 26, 221-227 (2017).

55. Contreras, C. & Lopez, M. Ceramide sensing in the hippocampus: The lipostatic theory and Ockham's razor. *Mol. Metab* 3, 90-91 (2014).

56. Heras, V., et al. Central Ceramide Signaling Mediates Obesity-Induced Precocious Puberty. *Cell Metab* 32, 951-966e958 (2020).

57. Vazquez, M. J., et al. SIRT1 mediates obesity- and nutrient-dependent perturbation of pubertal timing by epigenetically controlling Kiss1 expression. *Nat. Commun* 9, 4194 (2018).

58. Sanchez-Garrido, M. A., et al. Intergenerational Influence of Paternal Obesity on Metabolic and Reproductive Health Parameters of the Offspring: Male-Preferential Impact and Involvement of Kiss1-Mediated Pathways. *Endocrinology* 159, 1005-1018 (2018).

59. Zadra, G., et al. A novel direct activator of AMPK inhibits prostate cancer growth by blocking lipogenesis. *EMBO Mol Med* 6, 519-538 (2014).

60. Tang, Y. C., Williams, B. R., Siegel, J. J. & Amon, A. Identification of aneuploidy-selective antiproliferation compounds. *Cell* 144, 499-512 (2011).

The invention claimed is:

1. A population of small extracellular vesicles (sEVs) comprising at least one polynucleotide encoding a dominant negative AMP-activated protein kinase alpha 1 (AMPKα1-DN) mutant protein, wherein the amino acid sequence of the AMPKα1-DN mutant protein consists of SEQ ID NO: 1, wherein said AMPKα1-DN mutant protein is operably linked and under the control of a steroidogenic factor 1 (SF1) promoter that has at least 98% sequence identity with SEQ ID NO: 3, and wherein the sEVs are engineered to express in their outer membrane at least one fusion protein comprising a neurotrophic rabies virus (RVG) peptide fused to lysosome-associated membrane protein 2b.

2. The population of sEVs according to claim 1, wherein the amino acid sequence of the SF1 promoter consists of SEQ ID NO: 3.

3. The population of sEVs according to claim 1, wherein the fusion protein comprising the RVG peptide fused to lysosome-associated membrane protein 2b comprises SEQ ID NO: 5, or a sequence with at least 90% sequence identity to SEQ ID NO: 5.

4. A method for treating or preventing obesity in a subject in need thereof, comprising administering the population of sEVs according to claim 1 to the subject.

5. The method according to claim 4, wherein the obesity is leptin receptor (LEPR) deficiency-induced obesity.

6. The method of claim 4, wherein the method ameliorates or reduces a rebound effect after the administration is ceased.

7. The method according to claim 6, wherein said amelioration or reduction of the rebound effect is measured at least 5 days after the administration is ceased.

8. The method according to claim 4, wherein the administration of said sEVs is systemic.

9. A method for treatment of obesity, comprising systemically administering to a subject in need thereof a population of small extracellular vesicles (sEVs) capable of significantly decreasing the activation levels of AMP-activated protein kinase (AMPK) in SF1 expressing neurons located in the ventromedial nucleus of the hypothalamus (VMH) in comparison to the activation levels of AMPK in untreated SF1 expressing cells, without said decrease being significantly reduced in other SF1 expressing tissues selected from the group consisting of adrenal glands, testicles, and pituitary gland;

wherein said population of sEVs comprises at least one polynucleotide encoding a dominant negative AMP-activated protein kinase alpha 1 (AMPKα1-DN) mutant protein, wherein the amino acid sequence of the AMPKα1-DN mutant protein consists of SEQ ID NO: 1, wherein said AMPKα1-DN mutant protein is operably linked and under the control of a steroidogenic factor 1 (SF1) promoter that has at least 98% sequence identity with SEQ ID NO: 3, and wherein the sEVs are engineered to express in their outer membrane at least one fusion protein comprising a neurotrophic rabies virus (RVG) peptide fused to lysosome-associated membrane protein 2b.

10. The method according to claim 9, wherein the amino acid sequence of the SF1 promoter consists of SEQ ID NO: 3.

11. The method according to claim 9, wherein the nucleotide sequence of the AMPKα1-DN mutant protein consists of SEQ ID NO: 2.

12. The method according to claim 9, wherein the fusion protein comprising the RVG peptide fused to lysosome-associated membrane protein 2b comprises SEQ ID NO: 5, or a sequence with at least 90% sequence identity to SEQ ID NO: 5.

13. The method according to claim 9, wherein the treatment comprises reverting or ameliorating obesity.

14. The method according to claim 9, wherein the systemically administering comprises administering via an intravascular route.

15. The population according to claim 1, wherein the sEVs have a size distribution of between 30 and 150 nm.

16. The population according to claim 15, wherein the sEVs further comprise one or more specific markers selected from the groups consisting of ALIX, TSG101, CD9 and CD81, and any combination thereof.

17. The population according to claim 16, wherein the sEVs lack GRP94 marker.

18. The population according to claim 16, wherein the sEVs are produced or obtained from immature antigen presenting cells comprising a statistically significant reduced expression of at least one T-cell activator molecule in comparison to the expression of said T-cell activator molecule in a mature antigen presenting cell.

19. The population according to any of claims 18, wherein the antigen presenting cell is a dendritic cell, and wherein the at least one T-cell activator molecule is one or more T cell-activator molecule selected from the group consisting of major histocompatibility complex II (MHC-II), cluster of differentiation 80 (CD80) and cluster of differentiation 86 (CD86), and a combination thereof.

20. The population according to claim 15, wherein the sEVs are exosomes.

* * * * *